United States Patent
Walker et al.

(10) Patent No.: US 6,777,440 B2
(45) Date of Patent: Aug. 17, 2004

(54) HIV INTEGRASE INHIBITORS

(75) Inventors: Michael A. Walker, Durham, CT (US);
Jacques Banville, St. Hubert (CA);
Roger Remillard, Napierville (CA);
Serge Plamondon, Ste-Catherine (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 26 days.

(21) Appl. No.: 10/313,058

(22) Filed: Dec. 6, 2002

(65) Prior Publication Data

US 2003/0176495 A1 Sep. 18, 2003

Related U.S. Application Data

(60) Provisional application No. 60/339,674, filed on Dec. 12, 2001.

(51) Int. Cl.[7] .................... A61K 31/335; A61K 31/275; A61K 31/195; C07D 317/00; C07C 51/16; C07C 229/00

(52) U.S. Cl. .................... 514/467; 514/482; 514/563; 549/296; 562/422; 562/444; 562/448

(58) Field of Search ................... lp;1p514/467, 514/ 482, 563; 549/296; 562/422, 444, 448

(56) References Cited

PUBLICATIONS

Carpenter, Charles C. J., et al., "Antiretroviral Therapy in Adults", JAMA, 283 (3), p. 381 (2000).
Neamati, Nouri, et al., "Design and Discovery of HIV–1 Integrase Inhibitors", *Drug Disc. Today*, 2 (11), p. 487–498 (1997).
Palella, Frank J., et al., "Declining Morbidity and Mortality Among Patients with Advanced Human Immunodeficiency Virus Infection", *N. Engl. J. Med.*, 338 (13), p. 853 (1998).

*Primary Examiner*—Johann Richter
*Assistant Examiner*—Paul A. Zucker
(74) *Attorney, Agent, or Firm*—Warren K. Volles; James R. Epperson

(57) ABSTRACT

The present invention relates to the inhibition of HIV integrase, and to the treatment of AIDS or ARC by administering compounds of the following formula, or a tautomer of said compound, or a pharmaceutically acceptable salt, solvate or prodrug thereof:

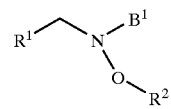

I wherein $R^1$, $R^2$ and $B^1$ are as defined herein.

19 Claims, No Drawings

HIV INTEGRASE INHIBITORS

CROSS-REFERENCE TO RELATED APPLICATIONS

This application claims the benefit of U.S. provisional application U.S. Ser. No. 60/339,674, filed Dec. 12, 2001.

BACKGROUND

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavaridine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C. J.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schecter, M.; Schoolery, R. T.; Thompson, M. A.; Vella, S.; Yeni, P. G.; Volberding, P. A. *JAMA* 2000, 283, 381). Clearly there is a need for new antiviral agents, preferably targeting other viral enzymes to reduce the rate of resistance and suppress viral replication even further.

HIV expresses three enzymes, reverse transcriptase, an aspartyl protease and integrase, all of which are potential antiviral targets for the development of drugs for the treatment of AIDS. However, integrase stands out as being the only viral enzyme not targeted by current therapy. The integrase enzyme is responsible for insertion of the viral cDNA into the host cell genome, which is a critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious. Therefore, an inhibitor of integrase would be useful as a therapy for AIDS and HIV infection.

A number of inhibitors of the enzyme have been reported. These include, nucleotide-based inhibitors, known DNA binders, catechols and hydrazide containing derivatives (Neamati, N.; Sunder, S.; Pommier, Y., *Drug Disc. Today*, 1997, 2, 487). However, no clinically active compound has resulted from these leads. Thus, what is needed is a clinically effective inhibitor of the HIV integrase enzyme.

SUMMARY OF THE INVENTION

The present invention relates to compounds of Formula I, or pharmaceutically acceptable salts or solvates thereof.

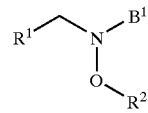

Formula I

In Formula I, $R^1$ is

-aryl,

—$C_1$–$C_6$ alkyl-aryl,

—$C_1$–$C_6$ alkyl-S(O)$_n$-aryl,

—$C_1$–$C_5$ alkyl-O-aryl; or wherein $R^1$ is unsubstituted or substituted with 1–3 $R^3$;

Each $R^3$ is independently selected from

—H,

-halo,

—CN,

—$C_1$–$C_6$ alkyl,

—$C_3$–$C_6$ cycloalkyl

—$OR^4$,

—$C_1$–$C_{10}$ alkyl-O—$R^4$,

—$CO_2R^5$,

—$C_1$–$C_{10}$ alkyl-$CO_2R^5$,

—$N(R^6)(R^7)$,

—$C_1$–$C_{10}$ alkyl-$N(R^6)(R^7)$,

—$CON(R^6)(R^7)$,

—$C_1$–$C_{10}$ alkyl-$CON(R^6)(R^7)$

—$S(O)_nR^8$,

—$C_1$–$C_{10}$ alkyl-$S(O)_nR^8$

—$S(O)_nN(R^9)(R^{10})$,

—$C_1$–$C_{10}$ alkyl-$S(O)_nN(R^9)(R^{10})$,

-aryl,

—O-aryl,

-heteroaryl,

—O-heteroaryl,

—$C_1$–$C_6$ alkyl-aryl,

—$C_1$–$C_6$ alkyl-heteroaryl,
—C(O)-heterocyclic radical,
—$C_1$–$C_{10}$ alkyl-C(O)-heterocyclic radical, or
—$C_1$–$C_6$ haloakyl;
$R^2$ is
—H,
—$C_1$–$C_{10}$ alkyl,
—$C_3$–$C_6$ cycloakyl,
—$C_1$–$C_{10}$ haloalkyl,
-aryl,
-heteroaryl,
—$C_1$–$C_6$ alkyl-aryl,
—$C_1$–$C_5$ alkyl-O-aryl,
—$C_1$–$C_6$ alkyl-heteroaryl,
—$C_1$–$C_5$ alkyl-O-heteroaryl,
—$C_1$–$C_{10}$ alkyl-$OR^4$,
—$C_1$–$C_{10}$ alkyl-$CO_2R^5$,
—$C_1$–$C_{10}$ alkyl-$N(R^6)(R^7)$,
—$C_1$–$C_{10}$ alkyl-$CON(R^6)(R^7)$,
—$C_1$–$C_{10}$ alkyl-$S(O)_nR^8$,
—$C_1$–$C_{10}$ alkyl-$S(O)_nN(R^9)(R^{10})$, or
—$C_1$–$C_{10}$ alkyl-C(O)-heterocyclic radical;
Each $R^4$ is independently selected from
—H,
—$C_1$–$C_6$ alkyl,
—$C_3$–$C_6$ cycloalkyl,
—$C_1$–$C_9$ alkyl-$CO_2R^5$,
—$C_1$–$C_9$ alkyl-$N(R^6)(R^7)$,
—$C_1$–$C_9$ alkyl-$CON(R^6)(R^7)$,
—$C_1$–$C_9$ alkyl-$S(O)_nR^8$, or
—$C_1$–$C_9$ alkyl-$S(O)_nN(R^9)(R^{10})$;
Each $R^5$ is independently selected from
—H,
—$C_1$–$C_6$ alkyl,
—$C_3$–$C_6$ cycloalkyl, or
—$C_1$–$C_6$ alkyl-aryl;
Each $R^6$ is independently selected from
—H,
—$C_1$–$C_6$ alkyl,
-aryl,
-heteroaryl,
—$C_1$–$C_6$ alkyl-aryl,
—$C_1$–$C_6$ alkyl-heteroaryl,
—C(O)—$C_1$–$C_6$ alkyl,
—C(O)-aryl,
—C(O)—$C_1$–$C_6$ alkyl-aryl,
—C(O)-heteroaryl,
—C(O)—$C_1$–$C_6$ alkyl-heteroaryl,
—$C(NH)NH_2$,
—$S(O)_n$—$R^8$, or
—$C_1$–$C_6$ alkyl-$CO_2R^5$;
Each $R^7$ is independently selected from
—H,
—$C_1$–$C_6$ alkyl,
-aryl, or
-heteroaryl;

Each $R^8$ is independently selected from
—$C_1$–$C_6$ alkyl,
-aryl, or
-heteroaryl;
Each $R^9$ is independently selected from
—H,
—$C_1$–$C_6$ alkyl,
—$C_1$–$C_6$ alkyl-aryl,
—$C_1$–$C_6$ alkyl-heteroaryl,
—C(O)—$C_1$–$C_6$ alkyl,
—C(O)-aryl,
—C(O)—$C_1$–$C_6$ alkyl-aryl,
—C(O)-heteroaryl,
—C(O)—$C_1$–$C_6$ alkyl-heteroaryl,
-aryl, or
-heteroaryl;
Each $R^{10}$ is independently selected from
—H,
—$C_1$–$C_6$ alkyl,
—$C_1$–$C_6$ alkyl-aryl,
—$C_1$–$C_6$ alkyl-heteroaryl,
-aryl, or
-heteroaryl;
$R^{11}$ is
—H,
-aryl,
-heteroaryl,
—$C_3$–$C_6$ cycloalkyl,
—$C_1$–$C_6$ alkyl,
—$C_1$–$C_6$ alkyl-aryl,
—$C_1$–$C_6$ alkyl-heteroaryl,
—$C_1$–$C_6$ alkyl-$CO_2R^5$, or
—$C_1$–$C_6$ alkyl-$N(R^6)(R^7)$;
$R^{12}$ is
—H,
—$C_1$–$C_6$ alkyl,
-aryl, or
-heteroaryl;
$R^{13}$ is
—H,
—$C_1$–$C_6$ alkyl,
-aryl, or
-heteroaryl;
$B^1$ is selected from the group consisting of

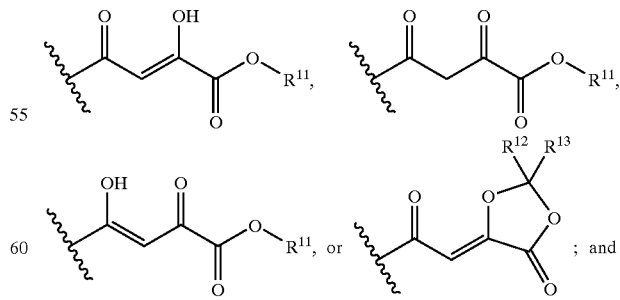

n is 0, 1 or 2.

The present invention also relates to a method of inhibiting HIV integrase by administering to a patient an effective amount of a compound of Structural Formula Ia, or a pharmaceutically acceptable salt, solvate or prodrug thereof.

Formula Ia

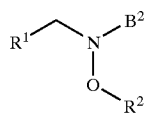

In Formula Ia, $R^1$, $R^2$, $R^3$, $R^4$, $R^5$, $R^6$, $R^7$, $R^8$, $R^9$ and $R^{10}$ are as defined for Formula I, whereas $B^2$ is

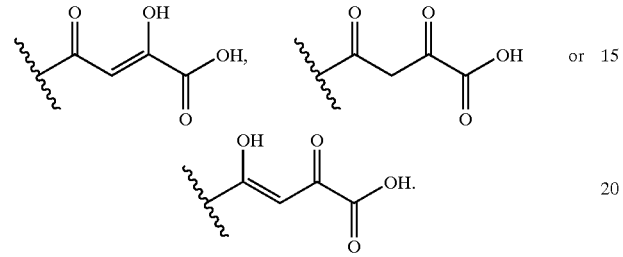

The present invention further relates to a method of treating patients infected by the HIV virus, or of treating AIDS or ARC, by administering to the patient an effective amount of a compound of Structural Formula Ia, or a pharmaceutically acceptable salt, solvate or prodrug thereof.

Another embodiment includes a pharmaceutical composition, useful for inhibiting HIV integrase, or for treating patients infected with the HIV virus, or suffering from AIDS or ARC, which comprises a therapeutically effective amount of one or more of the compounds of Formula Ia, including pharmaceutically acceptable salts, solvates or prodrugs thereof, and a pharmaceutically acceptable carrier.

DETAILED DESCRIPTION OF THE INVENTION

In the present invention, unless otherwise specified the following definitions apply.

The numbers in the subscript after the symbol "C" define the number of carbon atoms a particular group can contain. For example, "$C_1$–$C_6$" means a substituent containing from one to six carbon atoms.

As used herein, the term "alkyl" means a saturated, straight chain or branched monovalent hydrocarbon radical having the stated number of carbon atoms. Examples of such alkyl radicals include methyl, ethyl, n-propyl, isopropyl, n-butyl, isobutyl, sec-butyl, t-butyl and, where indicated, higher homologs and isomers such as n-pentyl, n-hexyl, 2-methylpentyl and the like. Haloalkyl refers to an alkyl radical that is substituted with one or more halo radicals, such as trifluoromethyl.

As used herein, the term "cycloalkyl" means a non-aromatic 3–6 membered ring. Examples include, cyclopropyl, cyclobutyl, cyclopentyl and cyclohexyl.

Halo means chloro, bromo, iodo or fluoro.

"Aryl" means an aromatic hydrocarbon having from six to fourteen carbon atoms; examples include phenyl and napthyl, indenyl, azulenyl, fluorenyl and anthracenyl.

The term "heterocyclic radical" refers to radicals derived from monocyclic saturated heterocyclic nuclei having 3–6 atoms containing 1–3 heteroatoms selected from nitrogen, oxygen or sulfur. Heterocyclic radicals include, for example, piperidinyl, piperazinyl, pyrrolidinyl and morpholinyl.

"Heteroaryl" means a five- or six-membered aromatic ring containing at least one and up to four non-carbon atoms selected from oxygen, sulfur and nitrogen. Examples of heteroaryl include 2-furyl, 3-furyl, 2-pyridyl, 3-pyridyl, 4-pyridyl, pyrazinyl, 2-thienyl, 3-thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, 1,3,5-triazinyl and 1,3,5-trithianyl.

In a preferred embodiment, compounds of the present invention that are useful for treating AIDS have the structure of Formula II.

Formula II

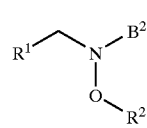

In Formula II, $R^1$, $R^2$, $R^3$, $R^4$, $R^5$, $R^6$, $R^7$, $R^8$, $R^9$ and $R^{10}$ are as defined for Formula I, while $B^2$ is defined as in Formula Ia.

In yet another embodiment of the present invention, compounds having the structure of Formula III, as follows, are preferred chemical intermediates from which compounds, or pharmaceutically acceptable salts, solvates or prodrugs, useful for the treatment of AIDS are formed. Even more preferentially, the compounds of Formula III are useful, themselves, as prodrugs and can be administered as a prodrug to a patient as a compound or in pharmaceutical formulation.

Formula III

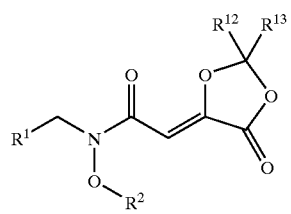

In Formula III, $R^1$, $R^2$, $R^3$, $R^4$, $R^5$, $R^6$, $R^7$, $R^8$, $R^9$, $R^{10}$, $R^{12}$ and $R^{13}$ are as defined for Formula I.

In a more preferred embodiment, compounds of the present invention have the structure of Formula IV, shown below Formula IV

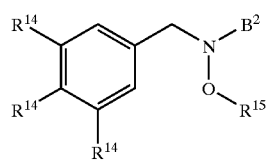

wherein:

Each $R^{14}$ is independently selected from
—CN,
—H, or
-halo;

$R^{15}$ is
—$CH_2C(O)N(CH_3)_2$ or
—$C_1$–$C_2$ alkyl; and $B^2$ is as defined for Formula Ia.

By virtue of its acidic moiety, where applicable, a compound of Formula I forms salts by the addition of a pharmaceutically acceptable base. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino aids such as lysine, arginine and N-methylglutamine. These salts may be prepared by methods known to those skilled in the art.

Salts of an amine group may also comprise quaternary ammonium salts in which the amino nitrogen carries a suitable organic group such as an alkyl, alkenyl, alkynyl or arylalkyl moiety.

Compounds of Formula I, which are substituted with a basic group, may exist as salts formed through acid addition. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Certain compounds of Formula I, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

This invention also encompasses pharmaceutically acceptable prodrugs of the compounds of Formula I. Prodrugs are derivatives of the compounds of the invention which have chemically or metabolically cleavable groups and become, by solvolysis or under physiological conditions, the compounds of the invention which are pharmaceutically active in vivo. A prodrug of a compound of Structural Formula I may be formed in a conventional manner with a functional group of the compounds such as with an amino, hydroxy or carboxy group. The prodrug derivative form often offers advantages of solubility, tissue compatibility, or delayed release in a mammalian organism (see, Bundgaard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or (alkoxycarbonyl)oxy)alkyl esters. Examples of prodrugs of compounds of the present invention include the compounds 1-A, 2-A, 3-C, 4-B, 5-B, 6-C, 7-C, 8-C, 9-C, 10-A, 11-C, 12-C, 13-C, 14-C, 15-C, 16-C, 17-C, 18-C, 19-C, 20-C, 21-C, 22-A, 22-B, 23-C, 25-C, 26-C, 27-C, 28-C, 29, 30-C, 31-C, 32-D, 32-E, 33, 34-C, 35-C, 36, 37-D, 38–61.

In addition, a compound of Structural Formula I, or a salt, solvate or prodrug thereof, may exhibit polymorphism. The present invention also encompasses any such polymorphic form.

Certain compounds of Structural Formula I may contain one or more chiral centers and exist in different optically active forms. When compounds of Structural Formula I contain one chiral center, the compounds exist in two enantiomeric forms. The present invention includes both enantiomers and mixtures of enantiomers such as racemic mixtures. The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of Structural Formula I may also exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

The compounds of this invention can also exist as tautomers; therefore the present invention also includes all tautomeric forms.

The compounds of Formula Ia are useful in the inhibition of HIV integrase, the prevention or treatment of infection by the human immunodeficiency virus and the treatment of consequent pathological conditions such as AIDS or ARC. The treatment involves administering to a patient, in need of such treatment, a compound of Formula Ia, or a pharmaceutically acceptable salt, solvate or prodrug thereof, or a pharmaceutical composition comprising a pharmaceutical carrier and a therapeutically effective amount of a compound of the present invention, or a pharmaceutically acceptable salt, solvate or prodrug therefor.

It will be appreciated by those skilled in the art that reference herein to treatment extends to prophylaxis as well as the treatment of established infections or symptoms. This includes initiating treatment pre- and post-exposure to the virus. In addition, the present invention can be administered in conjunction with other anti-HIV agents (HIV protease inhibitors, nucleoside reverse transcriptase inhibitors, non-nucleoside reverse transcriptase inhibitors, and HIV-entry inhibitors), immunomodulators, antiinfectives and/or vaccines.

The compounds of the present invention are also useful in the preparation and execution of screening assays for antiviral compounds. Further, the compounds of the present invention are useful in establishing or determining the binding site of other antiviral compounds to HIV integrase, for example, by competitive inhibition.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

This invention also provides a pharmaceutical composition for use in the above described therapeutic method. A pharmaceutical composition of the present invention comprises an effective amount of a compound of Formula I in association with a pharmaceutically acceptable carrier, excipient or diluent.

The active ingredient in such formulations comprises from 0.1 percent to 99.9 percent by weight of the formulation. By "pharmaceutically acceptable" it is meant that the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixers, suspensions, emulsions, solutions, syrups, aerosols, (as a solid or in a liquid medium), soft and hard gelatin capsules, suppositories, sterile injectable solutions, sterile packaged powders and the like.

The compound can be administered by a variety of routes including oral, rectal, transdermal, subcutaneous, intravenous, intramuscular and intranasal.

When administered orally, these compositions are prepared according to techniques well-known in the art of pharmaceutical formulation. For oral administration, the compound is typically formulated with excipients such as binders, fillers, lubricants, extenders, diluents, disintegration agents and the like as are known in the art.

For parenteral administration, the compound is formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

A compound of the present invention, or a salt or solvate thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds of the present invention can also be administered to humans in a dosage range of 1 to 100 mg/kg body weight in divided doses. One preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the route of administration, the age, body weight general health, sex,diet, mode and time of administration, rate of excretion, drug combination, the severity of the particular condition, and the host undergoing therapy.

General methods useful for the synthesis of compounds embodied in this invention are shown below. The preparations shown below are disclosed for the purpose of illustration and are not meant to be interpreted as limiting the processes to make the compounds by any other methods It will be appreciated by those skilled in the art that a number of methods are available for the preparation of the compounds of the present invention as provided by Structural Formula I. A compound of Structural Formula I may be prepared by processes which include processes known in the chemical art for the production of structurally analogous compounds or by a novel process described herein. A process for the preparation of a compound of Structural Formula I (or a pharmaceutically acceptable salt thereof) and novel intermediates for the manufacture of a compound of Formula I, as defined above, provide further features of the invention and are illustrated by the following procedures in which the meanings of the generic radicals are as defined above, unless otherwise specified. It will be recognized that it may be preferred or necessary to prepare a compound of Formula I in which a functional group is protected using a conventional protecting group, and then to remove the protecting group to provide the compound of Formula I.

Thus, there is provided a process for preparing a compound of Formula I (or a pharmaceutically acceptable salt thereof) as provided in any of the above descriptions which is selected from any of those described in the examples, including the following.

Schemes I and II illustrate the synthesis of non-commercially available N-,O-disubstituted hydroxylamines I-C and II-C. In Scheme I benzaldehyde, I-A, substituted with 1–3 $R^3$ groups is condensed with hydroxylamine or an O-substituted hydroxylamine derivative. In the event that the hydroxyl group is unsubstituted ($R^2$=H), this position can be functionalized via nucleophilic attack on an appropriately substituted $R^2$—X electophile (X=Cl, Br, I, —OTs, —OMs, —OTf). It will be appreciated by those skilled in the art that this reaction can be conducted in a number of different ways. The resulting oxime I-B can be easily reduced to the corresponding N-,O-disubstituted hydroxylamine using sodium cyanoborohydride, or a related reducing agent such as triethylsilane, under acidic conditions. In scheme II, and O-substituted hydroxyl amine is acylated wit Boc-anhydride to form intermediate II-A. This can be reacted with an appropriately substituted $R^1CH_2$—X electophile (X=Cl, Br, I, —OTs, —OMs or —OTf) under basic conditions to yield the Boc-protected N-,O-disubstituted hydroxylamine II-B. The Boc-protecting group is removed to yield N-,O-disubstituted hydroxylamine II-C. It will be appreciated by those skilled in the art that other protecting groups or acylating agents can be used in place of the Boc-group to effect the same transformation.

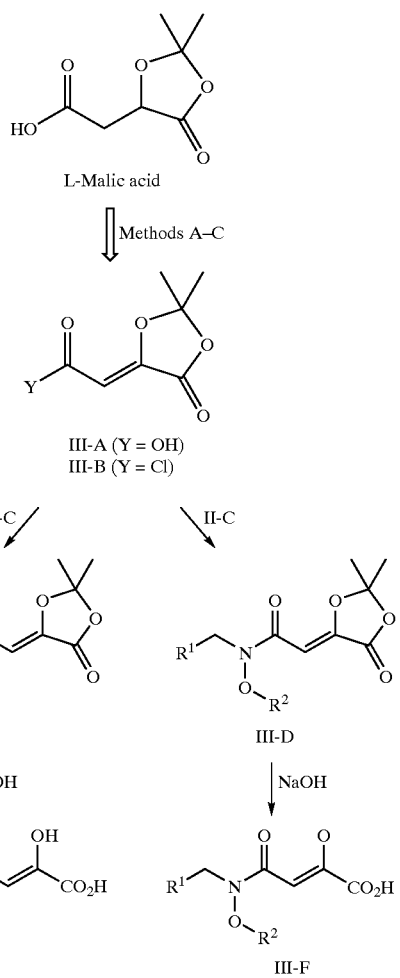

As shown in Scheme III, the N-,O-disubstituted hydroxylamines are then coupled to dioxolane III-A or III-B using standard amide bond forming chemistry. The syntheses of the dioxolanes III-A and III-B are described in the exemplification section. The resulting intermediates III-C and III-D are saponified with NaOH or LiOH to yield integrase inhibitors III-E and III-F.

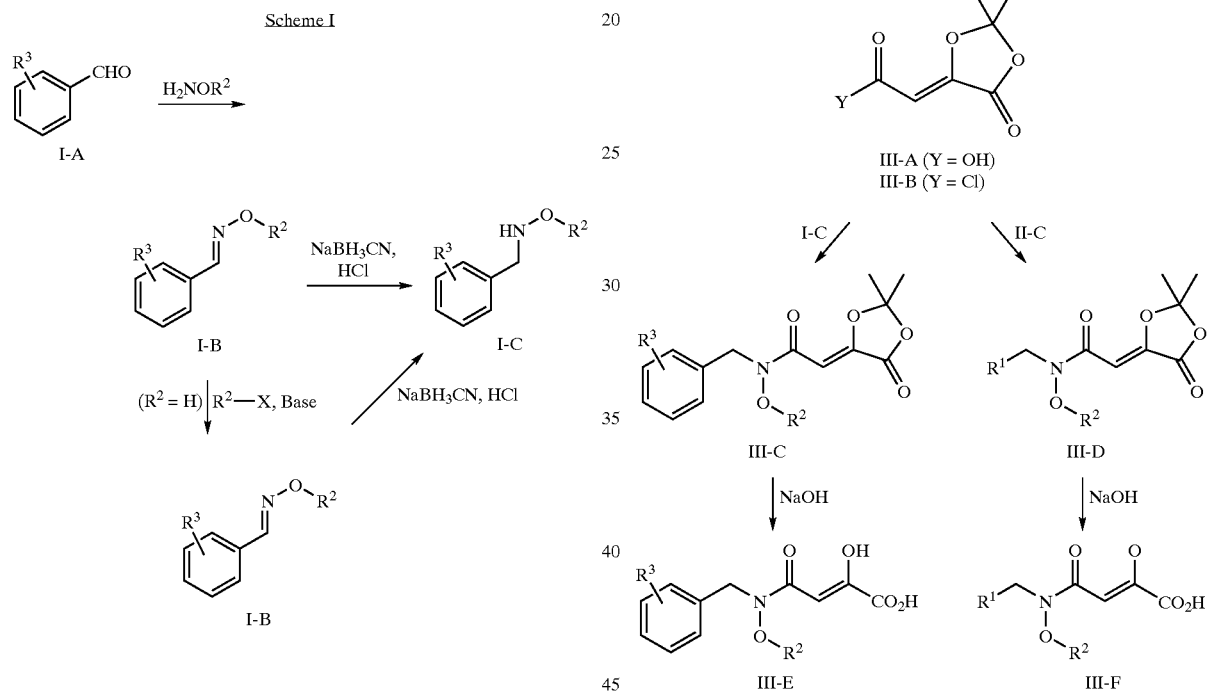

Alternative synthetic methods useful for producing the compounds described in this invention are illustrated in Scheme IV. The acylated N,O-disubstituted hydroxylamine IV-A can be synthesized starting directly from II-C, synthesized as shown previously or via a different route which commences with compound IV-C. IV-C can be reacted with N,O-bis-Boc-hydroxylamine to yield intermediate IV-D. After removal of the Boc-protecting groups this is acylated with acetyl chloride or acetic acid anhydride under standard amide bond forming conditions to produce IV-F. The hydroxyl group is then functionalized via nucleophilic substitution of an appropriately activated $R^2$—X (X=Cl, Br, I, —OTs, —OMs or OTf) yielding IV-A. This intermediate is condensed with dimethyl oxalate in a Claisen reaction carried out using lithium bis(trimethylsilyl)amide. Ester IV-B is saponified using NaOH or LiOH to yield integrase inhibitors III-F.

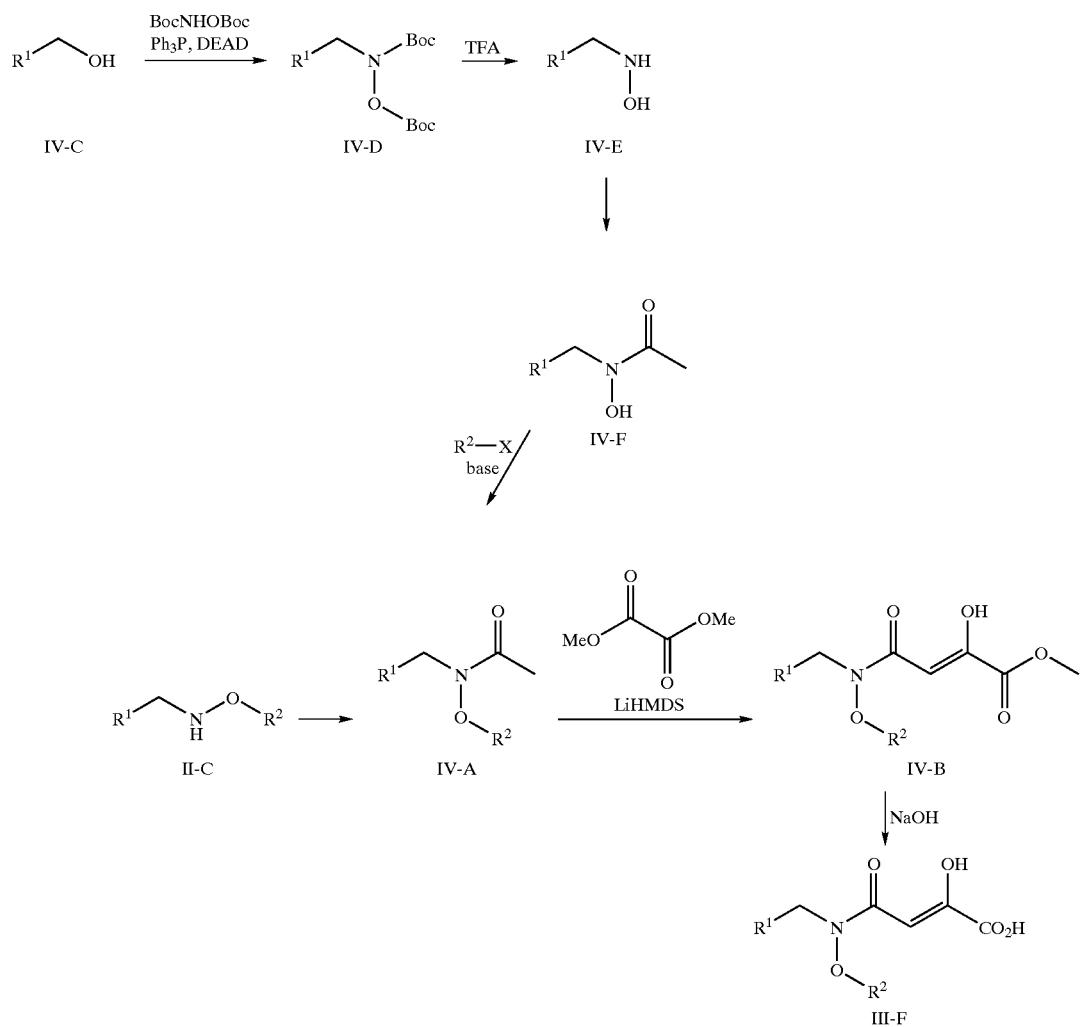
Starting from intermediate 20-C, Scheme V, illustrates the synthesis of compounds 20, 22-A, 22-B, 22 and 24.
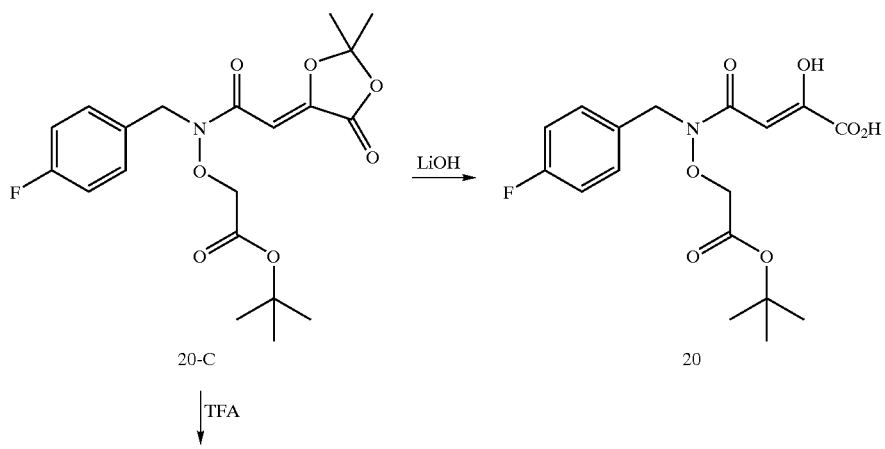

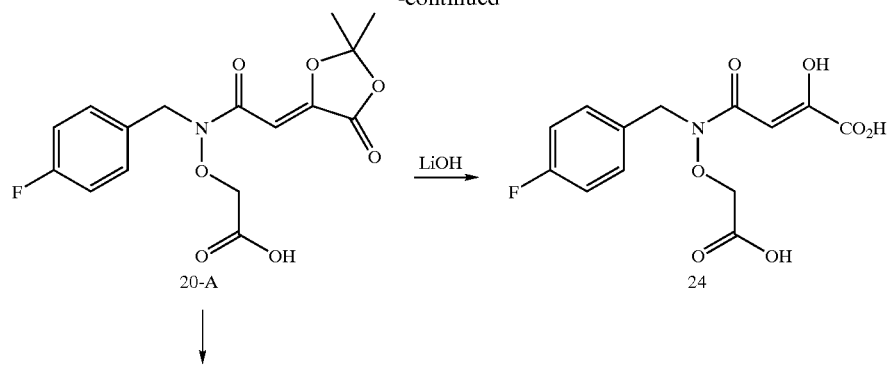

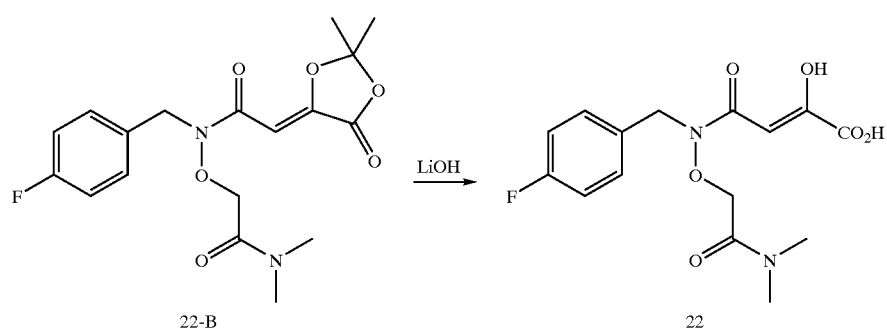

In Scheme VI compound 22-A is converted to the corresponding acid chloride, compound 38-A, using oxalyl chloride. This is subsequently reacted with amine VI-A using a suitable base catalyst to yield intermediate VI-B. This intermediate is hydrolyzed under basic conditions (LiOH) to produce inhibitors VI-C.

Scheme VI

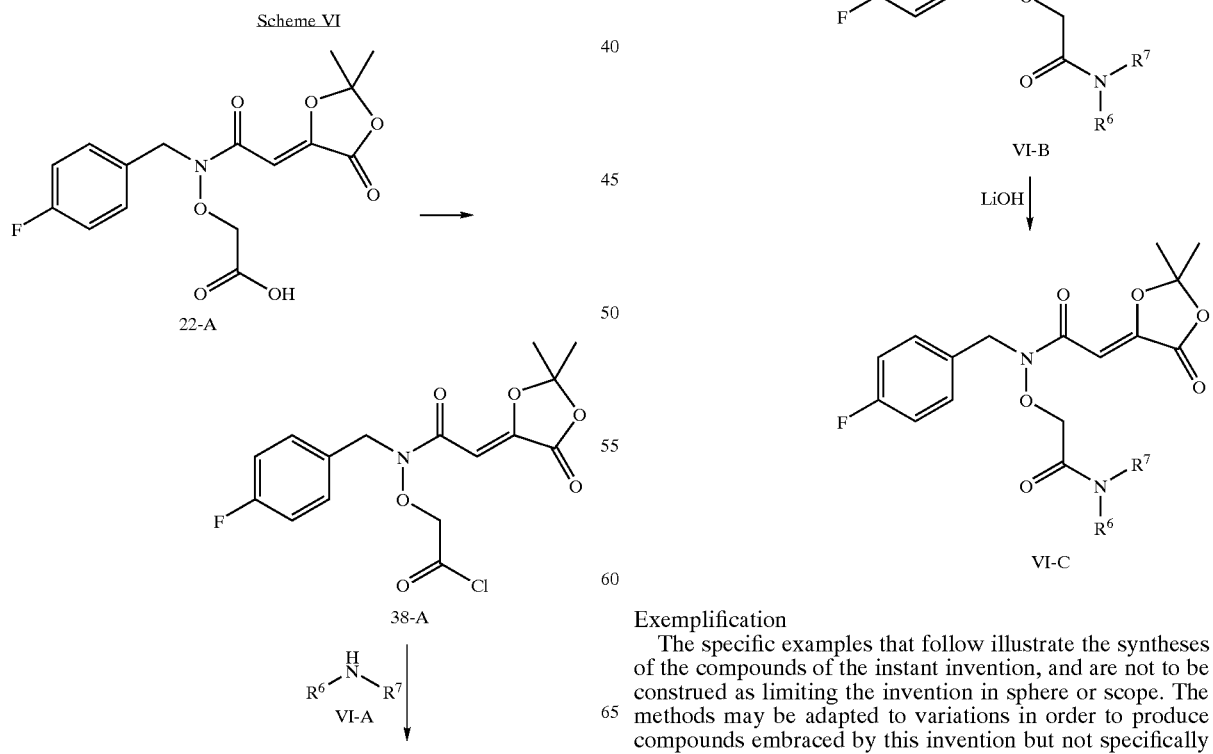

Exemplification

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C.) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents.

The abbreviations used herein are conventional abbreviations widely employed in the art. Some of which are: calcd (calculated); DMSO (dimethylsulfoxide); EtOAc (ethyl acetate); HPLC (high-pressure liquid chromatography); LC/MS (liquid chromatography, mass spectroscopy); LDA (lithium diisopropyl amide); LiHMDS (lithium bis(trimethylsilyl)amide); $SiO_2$ (silica gel); THF (tetrahydrofuran), TFA (trifluoroacetic acid), Me (methyl), Et (ethyl), Ph (phenyl), tBuOK (potassium tert-butoxide), NaOMe (sodium methoxide), NaOEt (sodium ethoxide), Boc (tert-butoxycarbonyl), and DEAD (diethylazo dicarboxylate).

Method A

Compound A-1: (S)-(+)-2,2-Dimethyl-5-oxo-1,3-dioxolane-4-acetic acid, tert-butyldiphenylsilyl ester

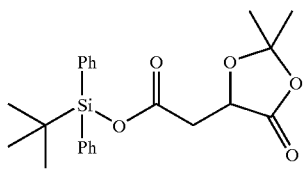

A solution of (S)-(+)-2,2-dimethyl-5-oxo-1,3-dioxolane-4-acetic acid (2.08 g, 11.9 mmol) in dry dichloromethane (20 ml) was treated with triethylamine (1.83 ml, 13.1 mmol) followed by a solution of t-butylchlorodiphenylsilane (3.44 g, 12.5 mmol) in dichloromethane (5 ml) added dropwise over 5 minutes. After 3 hours at 22° C., the reaction mixture was diluted with toluene (250 ml) washed with water, saturated sodium bicarbonate, brine and dried over magnesium sulfate. Evaporation of the solvent under reduced pressure and chromatography of the residue on silica gel (4×12 cm) using a mixture of toluene and ethyl acetate (0–2%) as eluent gave 4.90 g (99% yield) of the title material as a clear oil. $^1H$ NMR (400 MHz, $CDCl_3$) δ: 1.13 (s, 9), 1.58 (s, 3), 3.05 (m, 2), 4.79 (dd, 1, J=4, 7), 7.4–7.8 (m, 10).

Compound A-2: 4-Bromo-2,2-dimethyl-5-oxo-1,3-dioxolane-4-acetic acid, tert-butlydiphenylsilyl ester

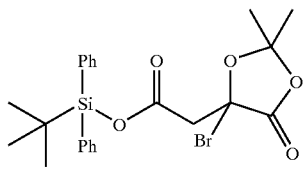

A solution of (S)-(+)-2,2-dimethyl-5-oxo-1,3-dioxolane-4-acetic acid, tert-butyldiphenylsilyl ester (21.65 g, 52.4 mmol) in carbon tetrachloride (160 ml) was treated with N-bromosuccinimide (9.35 g, 52.4 mmol) and 2,2'-azobisisobutyronitrile (200 mg) and the resulting mixture was heated under reflux (bath temperature 85° C.) while irradiating with a 500 watt lamp. After 10 minutes, the reaction mixture was cooled and the succinimide was filtered. The solvent was evaporated under vacuum to give the title bromide as a light yellow oil (~26 g) which was used immediately for the next step. $^1H$ NMR (400 MHz, $CDCl_3$) δ: 1.12 (s, 9), 1.41 (s, 3), 1.80 (s, 3), 3.80 (m, 2), 7.3–7.7 (m, 10).

Compound A-3: (Z)-2,2-Dimethyl-5-(tert-butyldiphenylsilyloxycarbonyl-methylene)-1,3-dioxolan-4-one

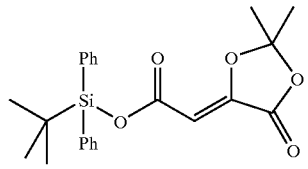

A solution of 4-bromo-2,2-dimethyl-5-oxo-1,3-dioxolane-4-acetic acid, tert-butyldiphenylsilyl ester (~26 g, 52.4 mmol) in dry tetrahydrofuran (160 ml) was cooled to 0° C. and treated dropwise over 5 minutes with 1,8-diazabicyclo[5,4,0]undec-7-ene (12.7 g, 78.8 mmol) and the resulting mixture was stirred at 5° C. for 1.5 hour. The solid formed was filtered and washed with a small amount of tetrahydrofuran. The filtrate was used as such for the next step.

Alternatively, the reaction mixture can be diluted with toluene, washed with water, saturated sodium bicarbonate, brine and dried (magnesium sulfate). Evaporation of the solvent gave an oil which was chromatographed on silica gel using a mixture of toluene and ethyl acetate (0–2%) as eluent. The title ester was obtained as an oil in 30–50% yield. $^1$HNMR (400 MHz, $CDCl_3$) δ: 1.16 (s, 9), 1.76 (s, 6), 5.97 (s, 1), 7.4–7.8 (m, 10).

Compound III-A: (2,2-Dimethyl-5-oxo-[1,3]dioxolan-4-ylidene)-acetic acid

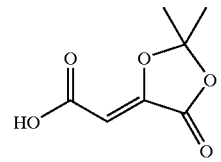

A solution of pure (Z)-2,2 dimethyl-5-(t-butyldiphenylsilyloxy-carbonylmethylene)-1,3-dioxolan-4- one (2.80 g, 6.82 mmol) in tetrahydrofuran (40 ml) was treated at 22° C. with acetic acid (2 ml) followed by 6.8 ml of a 1 M solution of tetrabutylammonium fluoride in tetrahydrofuran. After 15 minutes at 22° C., the reaction mixture was diluted with ethyl acetate, washed with water, brine and dried (magnesium sulfate). The solvent was concentrated under reduced pressure and the residue was triturated with toluene to give 1.00 g (85% yield) of the title compound as a white crystalline material: mp 203–204° C. (dec.). IR (KBr) ν max (cm$^{-1}$): 1805, 1707 and 1662. $^1$H NMR (400 MHz, CDCl$_3$) δ: 1.78 (s, 6), 5.89 (s, 1). Anal. calcd for C$_7$H$_8$O$_5$: C, 48.84; H, 4.68; Found: C, 48.84; H, 4.65.

Preparation of (2,2-Dimethyl-5-oxo-[1,3]dioxolan-4-ylidene)-acetic acid from crude A-3

A solution of the crude (Z)-2,2-dimethyl-5-(tert-butyldiphenylsilyloxycarbonyl methylene)-1,3-dioxolan-4-one (52.4 mmol) in tetrahydrofuran (200 ml) was treated with acetic acid (13 ml) followed with 50 ml of a 1 M solution of tetrabutylammonium fluoride in tetrahydrofuran. After 15 minutes at 22° C., the reaction mixture was filtered and the filtrate was concentrated in vacuo. Trituration of the residue with toluene gave 6.3 g (70% yield for three steps) of the title material as a white solid (>95% pure by $^1$HNMR).

Method B

Compound B-1: (+)-2,2-Dimethyl-5-oxo-1,3-dioxolane-4-acetic acid, tert-butyldimethylsilyl ester

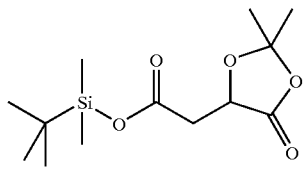

A solution of (S)-(+)-2,2-dimethyl-5-oxo-1,3-dioxolane-4-acetic acid (13.20 g, 75.8 mmol) in N,N-dimethylformamide (25 ml) was treated at 22° C. with imidazole (10.56 g, 0.155 mmol) followed by tert-butyldimethylsilyl chloride (12.0 g, 79.6 mmol) and the resulting mixture was stirred at 22° C. for 18 hours. The reaction mixture was then diluted with toluene (500 ml), washed with water (3 times), saturated sodium bicarbonate and brine. After drying (magnesium sulfate), the solvent was evaporated under reduced pressure to give an oil. Distillation under vacuum gave 20.9 g (96% yield) of the title material as a clear oil: Bp 80–90° C./0.1 torr (bulb to bulb distillation, air bath temperature). $^1$H NMR (400 MHz, CDCl$_3$) δ: 0.33 (s, 3), 0.36 (s, 3), 1.00 (s, 9), 1.11 (s, 3), 1.37 (s, 3), 2.72 (m, 2), 4.35 (dd, 1, J=4, 6).

Compound B-2: 4-Bromo-2,2-dimethyl-5-oxo-1,3-dioxolane-4-acetic acid, tert-butyldimethylsilyl ester

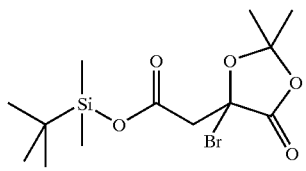

A solution of (S)-(+)-2,2-dimethyl-5-oxo-1,3-dioxolane-4-acetic acid, t-butyldimethylsilyl ester (20.9 g, 72.4 mmol) in carbon tetrachloride (200 ml) was treated with N-bromosuccinimide (14.18 g, 79.6 mmol) and 2,2'-azobisisobutyronitrile (0.30 g) and the resulting mixture was heated under reflux while irradiating with a 500 W lamp. After ~5 minutes, a mild exothermic reaction was observed and the mixture was heated for an additional 5 minutes. The reaction mixture was then cooled in an ice bath and the floating succinimide was filtered and washed with a small amount of carbon tetrachloride. The filtrate was used immediately as such for the next step. $^1$H NMR (400 MHz, CDCl$_3$) δ: 0.27 (s, 3), 0.28 (s, 3), 0.94 (s, 9), 1.66 (s, 3), 1.84 (s, 3), 3.62 (m, 2).

Compound B-3: (Z)-2,2-Dimethyl-5-(tert-butyldimethylsilyloxycarbonyl-methylene)-1,3-dioxolane

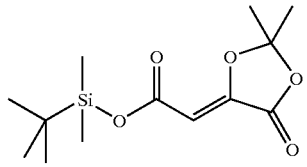

The solution of crude 4-bromo-2,2-dimethyl-5-oxo-1,3-dioxolane-4-acetic acid, tert-butyldimethylsilyl ester (72.4 mmol) in carbon tetrachloride (~220 ml) was cooled to 0–5° C. and treated dropwise over 10 minutes and under good stirring with a solution of 1,8-diazabicyclo [5,4,0]undec-7-ene (12.1 g, 79.6 mmol) in dry tetrahydrofuran (125 ml). A heavy precipitate was formed which gradually became a granular solid. After 1 h, the solid obtained was filtered and washed with a small amount of tetrahydrofuran. The filtrate was concentrated under reduced pressure to give a light orange oil which was used as such for the next step.

Compound III-A: (2,2-Dimethyl-5-oxo-[1,3] dioxolan-4-ylidene)-acetic acid

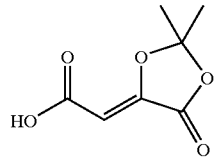

The crude (Z)-2,2-dimethyl-5-(tert-butyldimethylsilyloxycarbonylmethylene)-1,3-dioxolan-4-one (72.4 mmol) in tetrahydrofuran (50 ml) was treated at 22° C. with acetic acid (13 ml, 0.227 mmol) followed by 73 ml (73.0 mmol) of a 1M solution of tetrabutylammonium fluoride in tetrahydrofuran. After 1 h at 22° C., the reaction mixture was diluted with ethyl acetate (500 ml), washed with water, brine and dried (anhydrous magnesium sulfate). Evaporation of the solvent under reduced pressure and trituration of the residual solid with toluene (50 ml) gave 7.70 g (62% yield for 3 steps) of the title Z-isomer as a white crystalline solid. Concentration of the mother liquors yielded another 0.2 g of a 75:25 mixture of Z and E isomers. Z-Isomer; $^1$H NMR (400 MHz, CDCl$_3$) δ: 1.78 (s, 3), 5.89 (s, 1). E-Isomer: $^1$H NMR (400 MHz, CDCl$_3$) δ: 1.80 (s, 3), 6.03 (s, 1).

Method C

Compound III-B (2,2-Dimethyl-5-oxo-[1,3]dioxolan-4-ylidene)-acetyl chloride

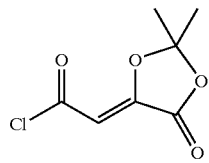

A mixture of (2,2-dimethyl-5-oxo-[1,3]dioxolan-4-ylidene)-acetic acid (0.50 g, 2.9 mmol) in dry dichloromethane (10 ml) was treated at 22° C. with oxalyl chloride (0.5 ml, 5.8 mmol) followed by a trace (capillary) of N,N-dimethylformamide. After 1 h at 22° C., the clear solution was concentrated in vacuo to give 0.55 g (quantitative) of the title acid chloride as a white crystalline solid.

EXAMPLE 1

Compound 1-A: N-Benzyl-2-(2,2-dimethyl-5-oxo-[1,3]-dioxolan-4-ylidene)-N-methoxy-acetamide

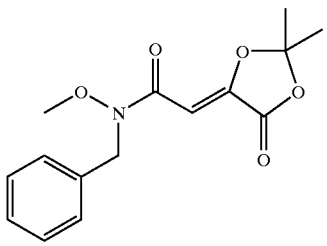

A solution of (2,2-dimethyl-5-oxo-[1,3]dioxolan-4-ylidene)-acetyl chloride (0.33 g, 1.74 mmol) in dichloromethane (5 ml) was added dropwise to a cold (0–5° C.) mixture of N-benzyl-O-methyl-hydroxylalmine (0.288 g, 2.1 mmol) (Keck, G. E. Wager, T. T.; McHardy, S. F. Tetrahedron, 55, 1999, 11755–11772) and pyridine (0.21 ml, 2.6 mmol) in dichloromethane (10 ml). The cooling bath was then removed and the solution was stirred at 22° C. for 1.5 hours. The reaction mixture was then quenched by the addition of water and ethyl acetate. The organic phase was washed successively with 0.1 N hydrochloric acid, saturated sodium bicarbonate, brine and dried (magnesium sulfate). Evaporation of the solvent and chromatography of the residue on silica gel (toluene-ethyl acetate, 75:25) gave 0.482 g (94% yield) of the title amide as white crystals: mp 109–110° C. (ethyl acetate-hexane). $^1$HNMR 400 MHz (CDCl$_3$) δ (ppm): 1.80 (6H, s), 3.67 (3H, s), 4.84 (2H, s), 6.41 (1H, s), 7.29–7.37 (5H, m). Anal. calcd for C$_{15}$H$_{17}$NO$_5$: C 61.84, H 5.88, N 4.80; Found: C 61.74, H 5.94, N 4.76.

Compound 1: 3-(Benzyl-methoxy-carbamoyl)-2-hydroxy-acrylic acid

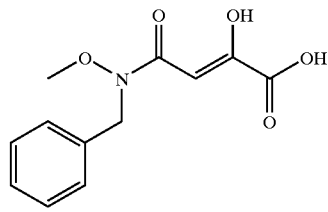

A solution of N-benzyl-2-(2,2-dimethyl-5-oxo-[1,3]-dioxolan-4-ylidene)-N-methoxy-acetamide (0.267 g, 0.917 mmol) in tetrahydrofuran (10 ml) was treated at 22° C. with 2 ml (2 mmol) of 1 M aqueous sodium hydroxide. After 1 h, the reaction mixture was acidified with 1N hydrochloric acid and extracted with ethyl acetate. The organic phase was washed with brine, dried (magnesium sulfate) and the solvent evaporated in vacuo to give 0.220 g (95% yield) of the title material as a white solid. $^1$HNMR 400 MHz (CDCl$_3$) δ (ppm) : 3.70 (3H, s), 4.85 (2H, s), 6.57 (1H, s), 7.32–7.37 (5H, m).

EXAMPLE 2

Compound 2-A: N-Benzyl-N-benzyloxy-2-(2,2-dimethyl-5-oxo-[1,3]dioxolan-4-ylidene)-acetamide

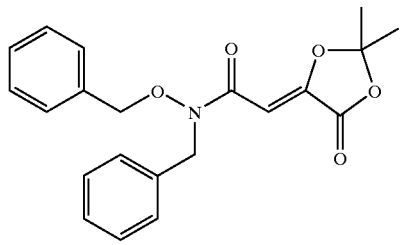

Reaction of (2,2-dimethyl-5-oxo-[1,3]dioxolan-4-ylidene)-acetyl chloride with N,O-dibenzyl-hydroxylamine (Bhat, J. I., Clegg, W.; Maskill, H.; Elsegood, M. R. J.; Menner, I. D.; Miatt, P. C. J. Chem. Soc. Perkin Trans. 2, 2000, 1435–1446) as described in the preparation of compound 1-A gave the title amide as white crystals (92% yield): mp 107–108° C. (ethyl acetate-hexane). $^1$HNMR 400 MHz (CDCl$_3$) δ (ppm): 1.72 (6H, s), 4.76 (2H, s), 4.84 (2H, s), 6.36 (1H, s), 7.28–7.38 (10H, m). HRMS (MAB N$_2$) calculated for C$_{21}$H$_{21}$NO$_5$[M$^+$]: 367.141973: Found: 367.140292.

Compound 2: 3-(Benzyl-benzyloxy-carbamoyl)-2-hydroxy-acrylic acid

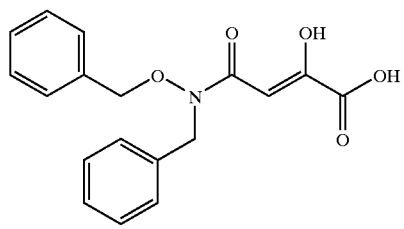

Saponification of (N-benzyl-N-benzyloxy-2-(2,2-dimethyl-5-oxo-[1,3]dioxolan-4-ylidene)-acetamide as described in the preparation of compound 1 gave the title material as a white solid (93% yield). ¹HNMR 400 MHz (CDCl₃) δ (ppm): 4.80 (2H, s), 4.83 (2H, s), 6.57 (1H, s), 7.19–7.43 (10H, m).

EXAMPLE 3

Compound 3-A: 4-Fluoro-benzaldehyde-O-methyl-oxime

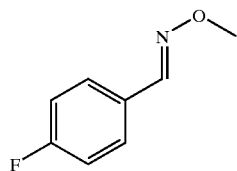

A solution of methoxylamine hydrochloride (13.4 g, 0.16 mol) in a mixture of water (150 ml) and tetrahydrofuran (50 ml) was treated with sodium acetate (11.2 g, 0.136 mol) followed by 4-fluorobenzaldehyde (11.57 g, 93.2 mmol) and the resulting mixture was stirred at 22° C. for 4 hours. The reaction mixture was then diluted with ether, washed with brine and dried over anhydrous magnesium sulfate. Evaporation of the solvent under reduced pressure gave 14.3 g of the crude title material as a clear oil which was used as such for the next step. Distillation of an aliquot in vacuo gave a clear oil; bp 45–50° C./0.5 torr. ¹HNMR 400 MHz (CDCl₃) δ (ppm): 3.99 (3H, s), 7.09 (2H, m), 7.6 (2H, m), 8.06 (1H, s).

Compound 3-B: N-(4-Fluoro-benzyl)-O-methyl-hydroxylamine

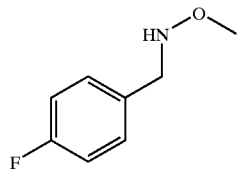

A solution of 4-fluorobenzaldehyde-O-methyloxime (93.2 mmol) in dichloromethane (150 ml) was treated with sodium cyanoborohydride (9.18 g, 0.146 mol) followed by 120 ml of 2 N hydrochloric acid in methanol added dropwise over 30 minutes. After 96 h at 22° C., the solvent was evaporated under reduce pressure and the residue was slurried with water and the pH was adjusted to 9 with 2 N aqueous sodium hydroxide. The aqueous phase was extracted twice with dichloromethane and the combined organic extracts were washed with brine, dried (magnesium sulfate) and concentrated under reduced pressure. The residual oil was chromatographed on silica gel (elution toluene-ethyl acetate 0–10%) and gave 5.92 g (41% yield) of the title amine as a clear oil. ¹HNMR 400 MHz (CDCl₃) δ (ppm): 3.49 (3H, s), 4.01 (2H, s), 5.69 (1H, broad s), 7.01 (2H, m), 7.31 (2H, m). The hydrochloride salt was obtained as a white solid: mp 170–171° C. Anal. calcd for C₈H₁₀FNO—HCl: C, 50.14; H, 5.78; N, 7.31. Found: C, 50.31; H, 5.80; N, 7.26

In an alternative procedure a solution of 4-fluorobenzaldehyde O-methyloxime (0.82 g, 5.35 mmol) in acetic acid ( 8 ml ) was treated at 10° C. with sodium cyanoborohydride (0.67 g, 10.7 mmol) added in small portions over 10 min and the resulting solution was stirred at 25° C. for 18 h. The solvent was evaporated under reduced pressure (co-evaporation with toluene twice) and the residue was slurried with water and the pH was adjusted to 9 with 2 N aqueous sodium hydroxide. The aqueous phase was extracted twice with ether and the combined organic extracts were washed with brine, dried (magnesium sulfate) and concentrated under reduced pressure. The residual oil was chromatographed on silica gel (elution hexane-ethyl acetate, 8:2) and distilled in vacuo to give 0.62 g (75% yield) of the title amine as a clear oil.

Compound 3-C: 2-(2,2-Dimethyl-5-oxo-[1,3]dioxolan-4-ylidene)-N-(4-fluoro-benzyl)-N-methoxy-acetamide

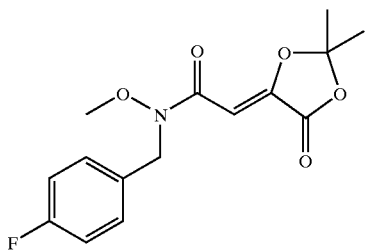

A solution of (2,2-dimethyl-5-oxo-[1,3]dioxolan-4-ylidene)-acetyl chloride (2.45 g, 12.9 mmol) in dichloromethane (15 ml) was added dropwise over 10 minutes to a cold (0–5° C.) mixture of N-4-fluorobenzyl-O-methyl-hydroxylamine (2.0 g, 12.9 mmol) and pyridine (2.1 ml, 25.7 mmol) in dichloromethane (50 ml). The cooling bath was then removed and the solution was stirred at 22° C. for 30 minutes. The reaction mixture was then quenched by the addition of water and ethyl acetate. The organic phase was washed successively with 0.1 N hydrochloric acid, saturated sodium bicarbonate, brine and dried (magnesium sulfate). Evaporation of the solvent and chromatography of the residue on silica gel (toluene-ethyl acetate, 8:2) gave 3.72 g (93% yield) of the title amide as white crystals after recrystallization from ethyl acetate/hexanes. Differential scanning calorimetry shows a sharp endotherm at 107° C. ¹HNMR 400 MHz (CDCl₃) δ (ppm): 1.75 (6H, s), 3.68 (3H, s), 4.79 (2H, s), 6.38 (1H, s), 7.0 (2H, m), 7.34 (2H, m). ¹³CNMR 100 MHz (CDCl₃) δ (ppm): 26.81, 48.43, 63.03, 94.48, 114.22, 115.31, 115.56, 130.47, 132.03, 146.95, 161.21, 162.46, 163.65, 164.43. ¹⁹FNMR 377 MHz(CDCl₃) δ (ppm): 114.97. Anal. calcd for C₁₅H₁₆FNO₅: C, 58.25; H, 5.21; N, 4.52; Found: C, 58.33; H, 5.38; N, 4.51.

Compound 3: 3-[(4-Fluoro-benzyl)-methoxy-carbamoyl]-2-hydroxy-acrylic acid

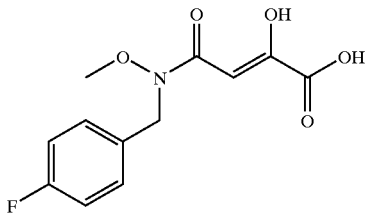

A solution of 2-(2,2-dimethyl-5-oxo-[1,3]dioxolan-4-ylidene)-N-(4-fluoro-benzyl)-N-methoxy-acetamide (3.65 g, 11.8 mmol) in tetrahydrofuran (150 ml) was treated at 15° C. with 35 ml (35 mmol) of 1 M aqueous sodium hydroxide.

After 30 minutes, the reaction mixture was acidified with 1N hydrochloric acid (65 ml) and extracted with ethyl acetate. The organic phase was washed with brine, dried (magnesium sulfate) and evaporated in vacuo to give a white solid. Recrystallization from ethyl acetate and hexane gave 3.04 g (96% yield) of the title material as white needles; mp 129° C. (dec.). $^1$HNMR 400 MHz (CDCl$_3$) δ (ppm): 3.73 (3H, s), 4.84 (2H, s), 6.57 (1H, s), 7.07 (2H, mn), 7.34 (2H, m). $^{13}$CNMR (enol form) 125 MHz (DMSO-d$_6$) δ (ppm): 47.08, 63.05, 93.35, 130.61, 130.83, 130.90, 132.86, 132.89, 133.14, 133.16, 161.02, 161.38, 163.32, 163.81, 170.97. Anal. calcd for C$_{12}$H$_{12}$FNO$_5$: C, 53.53; H, 4.49; N, 5.20; Found: C, 53.78; H, 4.30; N, 4.90.

EXAMPLE 4

Compound 4-A: N-(3,4-Dichloro-benzyl)-O-methyl-hydroxylamine

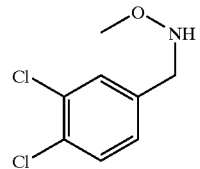

Reaction of 3,4-dichlorobenzaldehyde with methoxylamine hydrochloride followed by reduction with sodium cyanoborohydride as described in the preparation of compounds 3-A and 3-B gave the title hydroxylamine as a clear oil. $^1$HNMR 400 MHz (CDCl$_3$) δ (ppm): 3.48 (3H, s), 3.99 (2H, s), 5.74 (1H, broad s), 7.20 (1H, dd, J=2.0 Hz and J=8.1 Hz), 7.40 (1H, d, J=8.1 Hz), 7.47 (1H, d, J=2.0 Hz).

Compound 4-B: N-(3,4-Dichloro-benzyl)-2-(2,2-dimethyl-5-oxo-[1,3]dioxolan-4-ylidene)-N-methoxy-acetamide

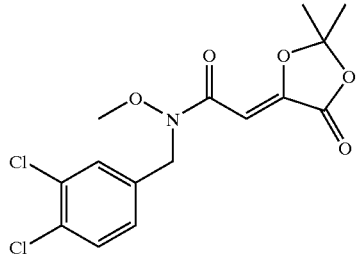

Reaction of (2,2-dimethyl-5-oxo-[1,3]dioxolan-4-ylidene)-acetyl chloride with N-3,4-dichlorobenzyl-O-methyl-hydroxylamine as described in the preparation of compound 1-A gave the title amide as a white solid (94% yield): mp 119–120° C. (ethyl acetate-hexane). $^1$HNMR 400 MHz (CDCl$_3$) δ (ppm): 1.76 (6H, s), 3.71 (3H, s), 4.72 (2H, s), 6.38 (1H, s), 7.20 (1H, dd, J=2.0 Hz and J=8.5 Hz), 7.40 (1H, d, J=8.5 Hz), 7.46 (1H, d, J=2.0 Hz). Anal. calcd for C$_{15}$H$_{15}$Cl$_2$NO$_5$: C, 50.02; H, 4.20; N, 3.89. Found: C, 50.12; H, 4.12; N, 3.80.

Compound 4: 3-[(3,4-Dichloro-benzyl)-methoxy-carbamoyl]-2-hydroxy-acrylic acid

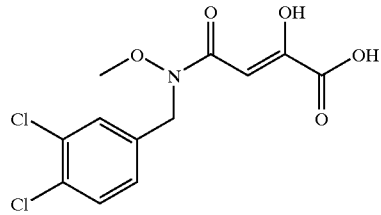

Saponification of N-(3,4-dichloro-benzyl)-2-(2,2-dimethyl-5-oxo-[1,3]dioxolan-4-ylidene)-N-methoxy-acetamide as described in the preparation of compound 1 gave the title material as a white solid (96% yield). $^1$HNMR 400 MHz (DMSO-d$_6$) δ (ppm): mixture of rotamers and keto-enol forms: 3.75 (3H, s), 4.90 (2H, s), 6.31 (1H, s), 7.28 (1H, dd, J=2.0 Hz and J=8.5 Hz,), 7.57 (1H, d, J=2.0 Hz), 7.62 (1H, d, J=8.5 Hz). HRMS (MAB N$_2$) calculated for C$_{12}$H$_{11}$Cl$_2$NO$_5$[M$^+$]: 319.001428: Found: 319.001699.

EXAMPLE 5

Compound 5-A: N-(3-Chloro-4-fluoro-benzyl)-O-methyl-hydroxylamine

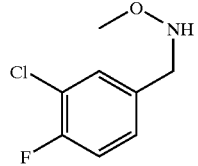

Reaction of 3-chloro-4-fluorobenzaldehyde with methoxylamine hydrochloride followed by reduction with sodium cyanoborohydride as described in the preparation of compounds 3-A and 3-B gave the title hydroxylamine as a clear oil. $^1$HNMR 400 MHz (CDCl$_3$) δ (ppm): 3.48 (3H, s), 3.98 (2H, s), 5.72 (1H, broad s), 7.10 (1H, t), 7.22 (1H, mn), 7.42 (1H, m).

Compound 5-B: N-(3-Chloro-4-fluoro-benzyl)-2-(2,2-dimethyl-5-oxo-[1,3]dioxolan-4-ylidene)-N-methoxy-acetamide

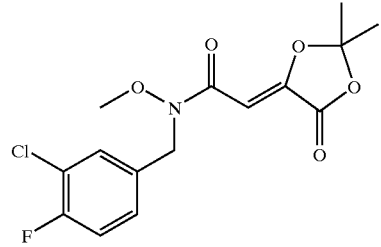

Reaction of (2,2-dimethyl-5-oxo-[1,3]dioxolan-4-ylidene)-acetyl chloride with N-(3-chloro-4-fluorobenzyl)-O-methyl-hydroxylamine as described in the preparation of compound 1-A gave the title amide as a white solid (91% yield): mp 110–111° C. (ethyl acetate-hexane). $^1$HNMR 400 MHz (CDCl$_3$) δ (ppm): 1.76 (6H, s), 3.71 (3H, s), 4.75 (2H, s), 6.38 (1H, s), 7.09 (1H, t, J=8.8 Hz), 7.23 (1H, m), 7.41 (1H, dd, J=2.4 Hz and J=6.8 Hz). Anal. calcd for $C_{15}H_{15}ClFNO_5$: C, 52.41; H, 4.39; N, 4.07. Found: C, 52.25; H, 4.36; N, 3.87.

Compound 5: 3-[(3-Chloro-4-fluoro-benzyl)-methoxy-carbamoyl]-2-hydroxy-acrylic acid

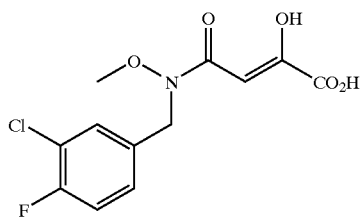

Saponification of N-(3-chloro-4-fluoro-benzyl)-2-(2,2-dimethyl-5-oxo-[1,3]dioxolan-4-ylidene)-N-methoxy-acetamide as described in the preparation of compound 1 gave the title material as a white solid (99% yield). $^1$HNMR 400 MHz (DMSO-$d_6$) δ (ppm): mixture of rotamers and keto-enol forms: 3.75 (3H, s), 4.88 (2H, s), 6.31 (1H, s), 7.29–7.53, (3H, m). HRMS (MAB $N_2$) calculated for $C_{12}H_{11}ClFNO_5[M^+]$: 303.030979; Found: 303.032401.

EXAMPLE 6

Compound 6-A: 3,4-Dichlorobenzaldehyde O-benzyl oxime

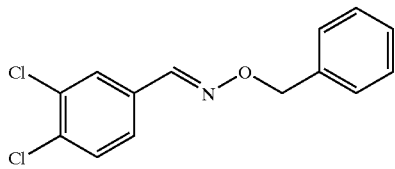

A solution of hydroxylamine hydrochloride (2.73 g, 39.3 mmol) in water (35 ml) was treated with sodium acetate (2.74 g, 33.4 mmol) followed by a solution of 3,4-dichlorobenzaldehyde (4.0 g, 22.8 mmol) in tetrahydrofuran (15 ml) and the resulting mixture was stirred at 22° C. for 2 h. The reaction mixture was then diluted with ether (250 ml), washed with water, brine and dried over anhydrous magnesium sulphate. Evaporation of the solvent gave 4.3 g of 3,4-dichlorobenzaldehyde oxime as a white solid.

Sodium hydride (1.05 g of 60% suspension in mineral oil, 0.63 g, 26.3 mmol) was washed with hexane, suspended in tetrahydrofuran (10 ml) and then treated with benzyl bromide (2.7 ml, 22.8 mmol) A solution of the above oxime in tetrahydrofuran (10 ml) was then added dropwise and the resulting mixture was stirred at 22° C. for 18 h. The reaction mixture was then diluted with dichloromethane, washed with water, brine and dried. Evaporation of the solvent and chromatography of the residue on silica gel (elution hexane-toluene, 8:2 to 1:1) gave 4.30 g (67% yield) of the title oxime ether as a clear oil. $^1$HNMR 400 MHz (CDCl$_3$) δ (ppm): 5.12 (2H, s, OCH$_2$), 7.3–7.44 (7H, m, aromatics), 7.68 (1H, d, aromatic), 8.04 (1H, s, CH).

Compound 6-B: O-Benzyl-N-(3,4-dichlorobenzyl)-hydroxylamine

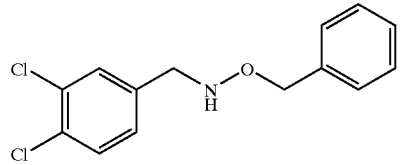

Reduction of 3,4-dichlorobenzaldehyde O-benzyl oxime as described in the preparation of compound 3-B gave the title hydroxylamine as a clear oil. The hydrochloride salt was obtained as a white solid. $^1$HNMR 400 MHz (DMSO-$d_6$) δ (ppm): 4.20 (2H, s, NCH$_2$), 4.83 (2H, s, OCH$_2$), 7.3–7.45 (6H, m, aromatics), 7.63 (1H, d, J=8.2 Hz, aromatic), 7.63 (1H, s, aromatic).

Compound 6-C: N-Benzyloxy-N-(3,4-dichloro-benzyl)-2-(2,2-dimethyl-5-oxo-[1,3]-dioxolan-4-ylidene)-acetamide

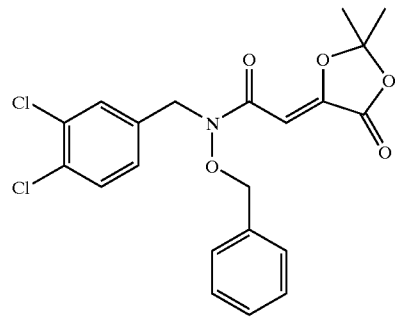

Reaction of (2,2-dimethyl-5-oxo-[1,3]dioxolan-4-ylidene)-acetyl chloride with O-benzyl-N-(3,4-dichlorobenzyl)-hydroxylamine as described in the preparation of compound 1-A gave the title amide as white crystals (78% yield): mp 113–116° C. (ethyl acetate-hexane). $^1$HNMR 400 MHz (CDCl$_3$) δ (ppm): 1.73 (6H, s, CH$_3$), 4.73 (2H, s, CH$_2$), 4.82 (2H, s, CH$_2$), 6.34 (1H, s, CH), 7.18–7.41 (8H, m, aromatics). Anal. calcd for $C_{21}H_{19}Cl_2NO_5$: C, 57.81; H, 4.39; N, 3.21. Found: C, 57.92; H, 4.21; N, 3.12.

Compound 6: 3-[Benzyloxy-(3,4-dichloro-benzyl)-carbamoyl]-2-hydroxy-acrylic acid

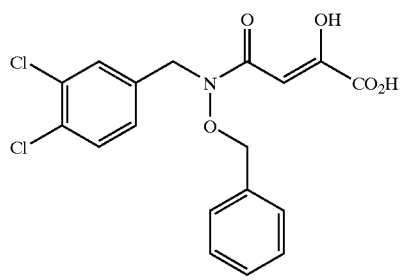

Saponification of N-benzyloxy-N-(3,4-dichloro-benzyl)-2-(2,2-dimethyl-5-oxo-[1,3]-dioxolan-4-ylidene)-acetamide as described in the preparation of compound 1 gave the title material as a white solid (91% yield). $^1$HNMR 400 MHz (CDCl$_3$) δ (ppm): 4.72 (2H, s, CH$_2$), 4.73 (2H, s, CH$_2$), 6.56

(1H, s, CH), 7.12–7.52 (8H, m, aromatics). HRMS (MAB N$_2$) calculated for C$_{18}$H$_{15}$Cl$_2$NO$_5$ [M$^+$]: 395.032728; Found: 395.033590.

EXAMPLE 7

Compound 7-A: 3-Fluorobenzaldehyde O-methyloxime

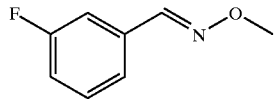

Reaction of 3-fluorobenzaldehyde with methoxylamine hydrochloride as described in the preparation of compound 3-A gave the title oxime ether as a clear oil. (94% yield). HPLC indicated a 88:12 mixture of E- and Z-isomer. $^1$HNMR 400 MHz (CDCl$_3$) δ (ppm): (E-isomer) 3.98 (3H, s, OCH$_3$), 7.03–7.08 (2H, m, aromatics), 7.26–7.36 (2H, m, aromatics), 8.02 (1H, s, CH).

Compound 7-B: N-3-Fluorobenzyl-O-methyl-hydroxylamine

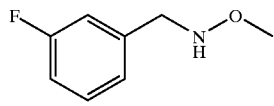

Reduction 3-fluorobenzaldehyde O-methyloxime with sodium cyanoborohydride as described in the preparation of compound 3-B gave the title hydroxylamine as a clear oil (60% yield). $^1$HNMR 400 MHz (CDCl$_3$) δ (ppm): 3.50 (3H, s, OCH$_3$), 4.04 (2H, s, NCH$_2$), 5.75 (1H, broad s, NH), 6.95–7.32 (4H, m, aromatics). The hydrochloride salt was obtained as a white solid: mp 130–131° C. (dec.). Anal. calcd for C$_8$H$_{10}$FNO—HCl: C, 50.14; H, 5.78; N, 7.31. Found: C, 50.10; H, 5.73; N, 7.38.

Compound 7-C: 2-(2,2-Dimethyl-5-oxo-[1,3]dioxolan-4-ylidene)-N-(3-fluoro-benzyl)-N-methoxy-acetamide

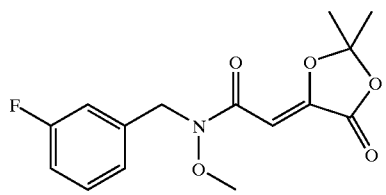

Reaction of (2,2-dimethyl-5-oxo-[1,3]dioxolan-4-ylidene)-acetyl chloride with N-(3-fluorobenzyl)-O-methyl-hydroxylamine as described in the preparation of compound 1-A gave the title amide as a white solid (94% yield): mp 110–111° C. (ethyl acetate-hexane). $^1$HNMR 400 MHz (CDCl$_3$) δ (ppm): 1.76 (6H, s, CH$_3$), 3.70 (3H, s, OCH$_3$), 4.82 (2H, s, NCH$_2$). 6.40 (1H, s, CH), 6.96–7.32 (4H, m, aromatics). Anal. calcd. for C$_{15}$H$_{16}$FNO$_5$: C, 58.25; H, 5.21; N, 4.52. Found: C, 58.00; H, 5.30; N, 4.49.

Compound 7: 3[(3-Fluoro-benzyl)-methoxy-carbamoyl]-2-hydroxy-acrylic acid

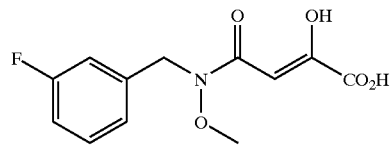

Saponification of 2-(2,2-dimethyl-5-oxo-[1,3]-dioxolan-4-ylidene)-N-methoxy-acetamide as described in the preparation of compound 1 gave the title material as a white solid (97% yield). $^1$HNMR 400 MHz (CDCl$_3$) δ (ppm): 3.73 (3H, s, OCH$_3$), 4.84 (2H, s, NCH$_2$), 6.57 (1H, s, CH), 7.0–7.35 (4H, m, aromatics). HRMS calcd. For C$_{12}$H$_{12}$FNO$_5$ [M$^+$]: 269.069951. Found: 269.070091.

EXAMPLE 8

Compound 8-A: 2-Fluorobenzaldehyde O-methyloxime

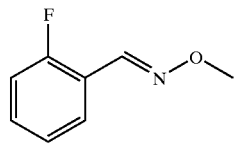

Reaction of 2-fluorobenzaldehyde with methoxylamine hydrochloride as described in the preparation of compound 3-A gave the title oxime ether as a clear oil (98% yield). HPLC indicated a 91:9 mixture of E- and Z-isomers. $^1$HNMR 400 MHz (CDCl$_3$) δ (ppm): (E-isomer) 3.99 (3H, s, OCH$_3$), 7.07 (1H, m, aromatic), 7.14 (1H, m, aromatic), 7.34 (1H, m, aromatic), 7.82 (1H, m, aromatic), 8.31 (1H, s, CH).

Compound 8-B: N-2-Fluorobenzyl-O-methyl-hydroxylamine

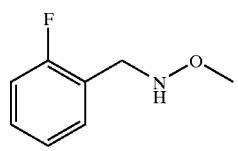

Reduction of 2-fluorobenzaldehyde O-methyloxime with sodium cyanoborohydride as described in the preparation of compound 3-B gave the title hydroxylamine as a clear oil (74% yield). $^1$HNMR 400 MHz (CDCl$_3$) δ (ppm): 3.52 (3H, s, OCH$_3$), 4.11 (2H, s, NCH$_2$), 5.78 (1H, broad s, NH), 7.05 (1H, m, aromatic), 7.11 (1H, m, aromatic), 7.27 (1H, m, aromatic), 7.38 (1H, m, aromatic). The hydrochloride salt was obtained as a white solid: mp 138–143° C. (dec.). Anal. calcd. for C$_8$H$_{10}$FNO—HCl: C, 50.14; H, 5.78; N, 7.31. Found: C, 50.37; H, 5.71; N, 7.18.

Compound 8-C: 2-(2,2-Dimethyl-5-oxo-[1,3]-dioxolan-4-ylidene)-N-(2-fluoro-benzyl)-N-methoxy acetamide

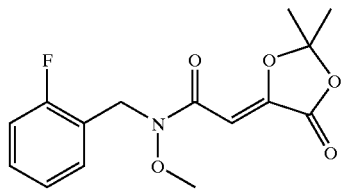

Reaction of (2,2-dimethyl-5-oxo-[1,3]dioxolan-4-ylidene)-acetyl chloride with N-(2-fluorobenzyl)-O-methyl-hydroxylamine as described in the preparation of compound 1-A gave the title amide as a white solid (84% yield): mp 109–111° C. (ethyl acetate-hexane). $^1$HNMR 400 MHz (CDCl$_3$) δ (ppm): 1.75 (6H, s, CH$_3$), 3.72 (3H, s, OCH$_3$), 4.92 (2H, s, NCH$_2$), 6.40 (1H, s, CH), 7.03–7.12 (2H, m, aromatics), 7.24–7.30 (1H, m, aromatic), 7.4 (1H, m, aromatic). Anal. calcd. for C$_{15}$H$_{16}$FNO$_5$: C, 58.25; H, 5.21; N, 4.52. Found: C, 58.47; H, 5.16; N, 4.66.

Compound 8: 3-[(2-Fluoro-benzyl)-methoxy-carbamoyl]-2-hydroxy-acrylic acid

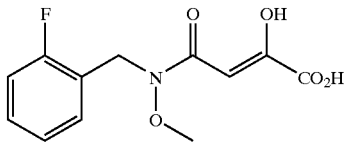

Saponification of 2-(2,2-dimethyl-5-oxo-[1,3]-dioxolan-4-ylidene)-N-(2-fluoro-benzyl)-N-methoxy acetamide as described in the preparation of compound 1 gave the title material as white crystals (60% yield). $^1$HNMR 400 MHz (CDCl$_3$) δ (ppm): 3.73 (3H, s, OCH$_3$), 4.84 (2H, s, NCH$_2$), 6.57 (1H, s, CH), 7.0–7.35 (4H, m, aromatics). HRMS (MAB N$_2$) calculated for C$_{12}$H$_{12}$FNO$_5$ [M$^+$]269.069951: Found: 269.070089.

EXAMPLE 9

Compound 9-A: 4-Fluorophenylacetaldehyde O-methyloxime

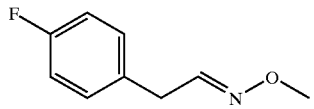

Reaction of 4-fluorophenylacetaldehyde with methoxy-lamine hydrochloride as described in the preparation of compound 3-A gave the title oxime ether as a clear oil (43% yield). $^1$HNMR indicated a 1:1 mixture of E- and Z-isomers. $^1$HNMR 400 MHz (CDCl$_3$) δ (ppm): 3.51 (2H, d, J=6.7 Hz, CH$_2$), 3.66 (2H, d, J=5.5 Hz, CH$_2$), 3.88 (3H, s, OCH$_3$), 3.96 (3H, s, OCH$_3$), 6.79 (1H, t, J=5.5 Hz, CH), 7.03 (2H, m, aromatics), 7.19 (2H, m, aromatics), 7.45 (1H, t, J=6.7 Hz, CH).

Compound 9-B: N-[2-(4-Fluorophenyl)-ethyl]-O-methyl-hydroxylamine

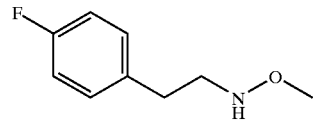

Reduction of 4-fluorophenylacetaldehyde O-methyloxime with sodium cyanoborohydride as described in the preparation of compound 3-B gave the title hydroxy-lamine as a clear oil after chromatography on silica gel (62% yield). $^1$HNMR 400 MHz (C$_6$D$_6$) δ (ppm): 2.64 (2H, t, J=7.1 Hz, CH$_2$), 2.97 (2H, t, J=7.1 Hz, CH$_2$), 3.53 (3H, s, OCH$_3$), 5.24 (broad, NH), 6.9 (4H, m, aromatics).

Compound 9-C: 2-(2,2-Dimethyl-5-oxo-[1,3]dioxolan-4-ylidene)-N-[2-(4-fluoro-phenyl)-ethyl]-N-methoxy-acetamide

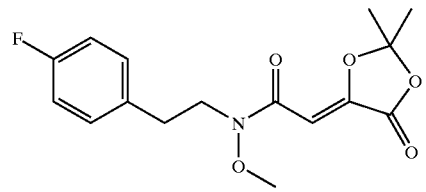

Reaction of (2,2-dimethyl-5-oxo-[1,3]dioxolan-4-ylidene)-acetyl chloride with N-[2-(4-fluorophenyl)-ethyl]-O-methyl-hydroxylamine as described in the preparation of compound 1-A gave the title amide as white crystals (86% yield): mp 106–107° C. (ethyl acetate-hexane). $^1$HNMR 400 MHz (CDCl$_3$) δ (ppm): 1.76 (6H, s, CH$_3$), 2.95 (2H, m, CH$_2$), 3.72 (3H, s, OCH$_3$), 3.87 (2H, m, NCH$_2$), 6.38 (1H, broad s, CH), 6.99 (2H, m, aromatics), 7.20 (2H, m, aromatics). Anal. calcd for C$_{16}$H$_{18}$FNO$_5$: C, 59.43; H, 5.61; N, 4.33. Found: C, 59.39; H, 5.43; N, 4.13.

Compound 9: 3-{[2-(4-Fluoro-phenyl)-ethyl]-methoxy-carbamoyl}-2-hydroxy-acrylic acid

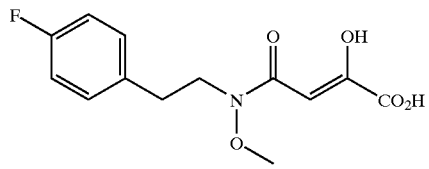

Saponification of 2-(2,2-dimethyl-5-oxo-[1,3]dioxolan-4-ylidene)-N-[2-(4-fluoro-phenyl)-ethyl]-N-methoxy-acetamide as described in the preparation of compound 1 gave the title material as white crystals (92% yield): mp 107–108° C. (dec) (ethyl acetate-hexane). $^1$HNMR 400 MHz (DMSO-d$_6$) δ (ppm): 2.88 (2H, t, J=7.1 Hz, CH$_2$), 3.72 (3H, s, OCH$_3$), 3.90 (2H, t, J=7.1 Hz, NCH$_2$), 6.25 (1H, s, CH), 7.11 (2H, m, aromatics), 7.28 (2H, m, aromatics), 13.27 (1H, broad, OH), 13.75 (1H, broad, OH). Anal. calcd for C$_{13}$H$_{14}$FNO$_5$: C, 55.12; H, 4.98; N, 4.94. Found: C, 55.05; H, 4.85; N, 4.91.

EXAMPLE 10

Compound 10-A: N-(4-Chloro-benzyl)-2-(2,2-dimethyl-5-oxo-[1,3]dioxolan-4-ylidene)-N-methoxy-acetamide

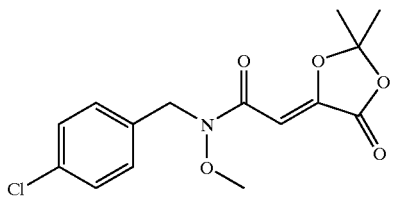

Reaction of (2,2-dimethyl-5-oxo-[1,3]dioxolan-4-ylidene)-acetyl chloride with N-(4-chlorobenzyl)-O-methyl-hydroxylamine (Kawase, M.; Kikugawa, Y. J. Chem. Soc. Perkin Trans.1, 1979, 643–645) as described in the preparation of compound 1-A gave the title amide as white crystals (95% yield): mp 129–130° C. (ethyl acetate-hexane). $^1$HNMR 400 MHz (CDCl$_3$) δ (ppm): 1.75 (6H, s, CH$_3$), 3.69 (3H, s, OCH$_3$), 4.79 (2H, s, NCH$_2$), 6.39 (1H, s, CH), 7.4 (4H, s, aromatics). Anal. calcd. for C$_{15}$H$_{16}$ClNO$_5$: C, 55.31; H, 4.95; N, 4.30. Found: C, 55.32; H, 4.95; N, 4.27.

Compound 10: 3-[(4-Chloro-benzyl)-methoxy-carbamoyl]-2-hydroxy-acrylic acid

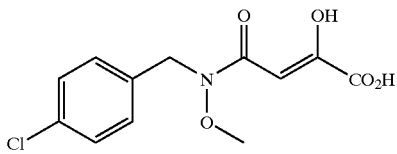

Saponification of N-(4-chloro-benzyl)-2-(2,2-dimethyl-5-oxo-[1,3]dioxolan-4-ylidene)-N-methoxy-acetamide as described in the preparation of compound 1 gave the title material as white crystals (74% yield). $^1$HNMR 400 MHz (CDCl$_3$) δ (ppm): 3.71 (3H, s, OCH$_3$), 4.81 (2H, s, NCH$_2$), 6.55 (1H, s, CH), 7.26–7.34 (4H, m, aromatics). HRMS (MAB N$_2$) calculated for C$_{12}$H$_{12}$ClNO$_5$[M$^+$]: 285.040400; Found: 285.039996.

EXAMPLE 11

Compound 11-A: 3,4-Difluorobenzaldehyde O-methyloxime

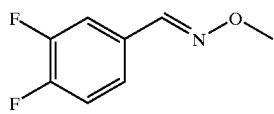

Reaction of 3,4-difluorobenzaldehyde with methoxylamine hydrochloride as described in the preparation of compound 3-A gave the title oxime ether as a clear oil (100% yield). $^1$HNMR indicated a 85:15 mixture of E- and Z-isomers. $^1$HNMR 400 MHz (CDCl$_3$) δ (ppm): (E-isomer) 3.97 (3H, s, OCH$_3$), 7.12–7.26 (2H, m, aromatics), 7.44–7.52 (1H, m, aromatic), 7.97 (1H, s, CH).

Compound 11-B: N-3,4-Difluorobenzyl-O-methyl-hydroxylamine

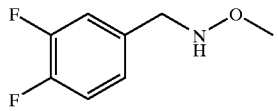

Reduction of 3,4-difluorobenzaldehyde O-methyloxime with sodium cyanoborohydride as described in the preparation of compound 3-B gave the title hydroxylamine as a clear oil (82% yield). $^1$HNMR 400 MHz (CDCl$_3$) δ (ppm): 3.48 (3H, s, OCH$_3$), 3.98 (2H, s, NCH$_2$), 5.73 (1H, broad s, NH), 7.04–7.23 (3H, m, aromatics). The hydrochloride salt was obtained as a white solid: mp 139–142° C. (dec.). Anal. calcd. for C$_8$H$_9$F$_2$NO$_2$—HCl: C, 45.83; H. 4.80; N, 6.68. Found: C, 45.96; H, 4.93, N, 6.67.

Compound 11-C: N-(3,4-Difluoro-benzyl)-2-(2,2-dimethyl-5-oxo-[1,3]dioxolan-4-ylidene)-N-methoxy-acetamide

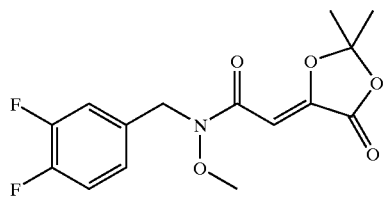

Reaction of (2,2-dimethyl-5-oxo-[1,3]dioxolan-4-ylidene)-acetyl chloride with N-3,4-difluorobenzyl-O-methyl-hydroxylamine as described in the preparation of compound 1-A gave the title amide as a white solid (96% yield): mp 110–111° C. (ethyl acetate-hexane). $^1$HNMR 400 MHz (CDCl$_3$) δ (ppm): 1.76 (6H, s, CH$_3$), 3.71 (3H, s, OCH$_3$), 4.72 (2H, s, NCH$_2$), 6.38 (1H, s, CH), 7.05–7.22 (3H, m, aromatics). Anal. calcd. for C$_{15}$H$_{15}$NO$_5$: C, 55.04; H, 4.62; N, 4.28. Found: C, 54.99; H, 4.55; N, 4.22.

Compound 11: 3-[(3,4-Difluoro-benzyl)-methoxy-carbamoyl]-2-hydroxy-acrylic acid

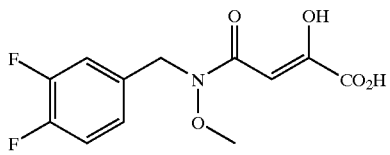

Saponification of N-(3,4-difluoro-benzyl)-2-(2,2-dimethyl-5-oxo-[1,3]dioxolan-4-ylidene)-N-methoxy-acetamide as described in the preparation of compound 1 gave the title material as white crystals (95% yield): mp 127–129° C. (ethyl acetate-hexane). $^1$HNMR 400 MHz (CDCl$_3$) δ (ppm): 3.73 (3H, s, OCH$_3$), 4.78.(2H, s, NCH$_2$), 6.55 (1H, s, CH), 7.04–7.19 (3H, m, aromatics). Anal. calcd. for C$_{12}$H$_{11}$F$_2$NO$_5$: C, 50.18; H, 3.86; N, 4.88. Found: C, 49.98; H, 3.91; N, 4.64.

EXAMPLE 12

Compound 12-A: 4-Fluorobenzaldehyde O-ethyloxime

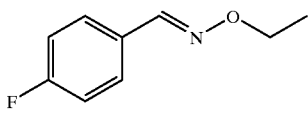

Reaction of 4-fluorobenzaldehyde with ethoxylamine hydrochloride as described in the preparation of compound 3-A gave the title oxime ether as a clear oil after chromatography on silica gel (elution toluene-ethyl acetate 95:5) and distillation (58% yield). $^1$HNMR 400 MHz (CDCl$_3$) δ (ppm): 1.35 (3H, t, J=7.07 Hz, CH$_3$), 4.24 (2H, q, J=7.07 Hz, OCH$_2$), 7.08 (2H, m, aromatics), 7.59 (2H, m, aromatics), 8.07 (1H, s, CH).

Compound 12-B: O-Ethyl-N-4-fluorobenzyl-hydroxylamine

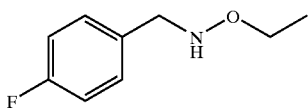

Reduction of 4-fluorobenzaldehyde O-ethyloxime with sodium cyanoborohydride as described in the preparation of compound 3-B gave the title hydroxylamine as a clear oil after chromatography (74% yield). $^1$HNMR 400 MHz (C$_6$D$_6$) δ (ppm): 1.13 (3H, t, J=7.1 Hz, CH$_3$), 3.70 (2H, q, J=7.1 Hz, OCH$_2$), 3.78 (2H, d, J=5.4 Hz, NCH$_2$), 5.20 (2H, broad t, NH), 6.89 (2H, m, aromatics), 7.09 (2H, m, aromatics). Anal. calcd for C$_9$H$_{12}$FNO: C, 63.88; H, 7.14; N, 8.27. Found: C, 63.68; H, 7.08; N, 8.46.

Compound 12-C: 2-(2,2-Dimethyl-5-oxo-[1,3]dioxolan-4-ylidene)-N-ethoxy-N-(4-fluoro-benzyl)-acetamide

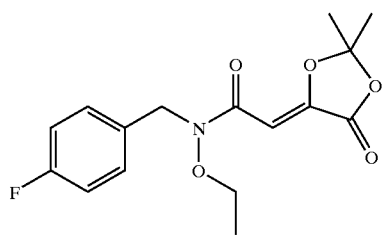

Reaction of (2,2-dimethyl-5-oxo-[1,3]dioxolan-4-ylidene)-acetyl chloride with O-ethyl-N-4-fluorobenzyl-hydroxylamine as described in the preparation of compound 1-A gave the title amide as white crystals (92% yield): mp 95–96° C. (ethyl acetate-hexane). $^1$HNMR 400 MHz (CDCl$_3$) δ (ppm): 1.27 (3H, t, J=7.07 Hz, CH$_3$), 1.77 (6H, s, CH$_3$), 3.90 (2H, q, J=7.07 Hz, OCH$_2$), 4.81 (2H, s, NCH$_2$), 6.41 (1H, s, CH), 7.03 (2H, m, aromatics), 7.37 (2H, m, aromatics). Anal. calcd for C$_{16}$H$_{18}$FNO$_5$: C, 59.43; H, 5.61; N, 4.33. Found: C, 59.50; H, 5.60; N, 4.17.

Compound 12: 3-[Ethoxy-(4-fluoro-benzyl)-carbamoyl]-2-hydroxy-acrylic acid

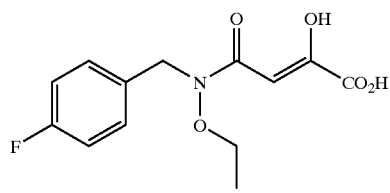

Saponification of 2-(2,2-dimethyl-5-oxo-[1,3]dioxolan-4-ylidene)-N-ethoxy-N-(4-fluorobenzyl)-acetamide as described in the preparation of compound 1 gave the title material as white crystals (96% yield): mp 120–121° C. (dec.), (ethyl acetate-hexane). $^1$HNMR 400 MHz (DMSO-d$_6$) δ (ppm): (mixture of enol and keto forms, 78: 22); enol form: 1.18 (3H, t, J=7.0 Hz, CH$_3$), 3.98 (2H, t, J=7.0 Hz, OCH$_2$), 4.87 (2H, s, NCH$_2$), 6.32 (1H, s, CH), 7.19 (2H, m, aromatics), 7.36 (2H, m, aromatics), 13.3 (1H, broad s, OH), 13.8 (1H, broad s, OH). Anal. calcd for C$_{13}$H$_{14}$FNO$_5$: C, 55.12; H, 4.98; N, 4.94. Found: C, 54.96; H, 4.80; N, 4.88.

EXAMPLE 13

Compound 13-A: 4-Fluorobenzaldehyde O-isobutyloxime

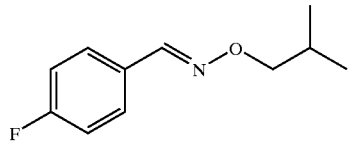

Reaction of 4-fluorobenzaldehyde with O-isobutyl-hydroxylamine hydrochloride as described in the preparation of compound 3-A gave the title oxime ether as a clear oil after chromatography on silica gel (elution toluene-ethyl acetate 95:5), (77% yield). $^1$HNMR 400 MHz (CDCl$_3$) δ (ppm): 0.98 (6H, d, J=6.5 Hz, CH$_3$), 2.07 (1H, m, CH), 3.95 (2H, d, J=7.18 Hz, OCH$_2$), 7.08 (2H, m, aromatics), 7.59 (2H, m, aromatics), 8.08 (1H, s, CH). Anal. calcd for C$_{11}$H$_{14}$FNO: C, 67.67; H, 7.22; N, 7.17. Found: C, 67.71; H, 7.32; N, 7.38.

Compound 13-B: N-(4-Fluorobenzyl)-O-isobutyl-hydroxylamine

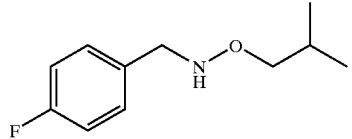

Reduction of 4-fluorobenzaldehyde O-isobutyloxime with sodium cyanoborohydride as described in the preparation of compound 3-B gave the title hydroxylamine as a clear oil after chromatography (65% yield). $^1$HNMR 400 MHz (C$_6$D$_6$) δ (ppm): 0.87 (6H, d, J=6.75 Hz, CH$_3$), 1.88 (1H, m, CH), 3.46 (2H, d, J=6.41 Hz, OCH$_2$), 4.05 (2H, s, NCH$_2$), 7.04 (2H, m, aromatics), 7.37 (2H, m, aromatics). Anal. calcd for C$_{11}$H$_{16}$FNO: C, 66.98; H, 8.17; N, 7.10. Found: C, 66.88; H, 7.97; N, 7.32.

Compound 13-C: 2-(2,2-Dimethyl-5-oxo-[1,3]dioxolan-4-ylidene)-N-(4-fluoro-benzyl)-N-isobutoxy-acetamide

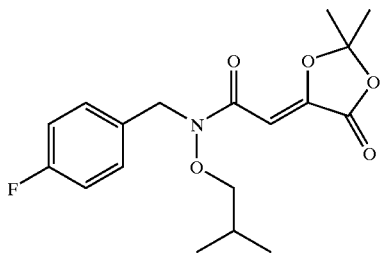

Reaction of (2,2-dimethyl-5-oxo-[1,3]dioxolan-4-ylidene)-acetyl chloride with N-(4-fluorobenzyl)-O-isobutyl-hydroxylamine as described in the preparation of compound 1-A gave the title amide as white crystals (91% yield): mp 105–106° C. (ethyl acetate-hexane). $^1$HNMR 400 MHz (CDCl$_3$) δ (ppm): 0.98 (3H, d, J=6.45 Hz, CH$_3$), 1.77 (6H, s, CH$_3$), 1.95 (1H, m, CH), 3.64 (2H, d, J=6.63 Hz, OCH$_2$), 4.80 (2H, s, NCH$_2$), 6.41 (1H, s, CH), 7.03 (2H, m, aromatics), 7.36 (2H, m, aromatics). Anal. calcd for C$_{18}$H$_{22}$FNO$_5$: C, 61.53; H, 6.31; H, 3.98. Found: C, 61.47; H, 6.39; N, 3.97.

Compound 13: 3-[(4-Fluoro-benzyl)-isobutoxy-carbamoyl]-2-hydroxy-acrylic acid

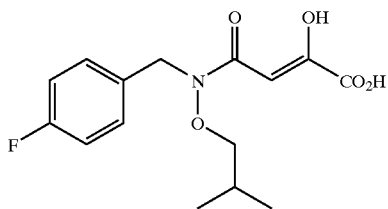

Saponification of 2-(2,2-dimethyl-5-oxo-[1,3]dioxolan-4-ylidene)-N-(4-fluorobenzyl)-N-isobutoxy-acetamide as described in the preparation of compound 1 gave the title material as white crystals (96% yield): mp 100–101° C., (ethyl acetate-hexane). $^1$HNMR 400 MHz (DMSO-d$_6$) δ (ppm): (mixture of enol and keto forms, 8:2); enol form: 0.91 (3H, d, J=6.49 Hz, CH$_3$), 1.47 (1H, m, CH), 3.74 (2H, d, J=5.84 Hz, OCH$_2$), 4.86 (2H, s, NCH$_2$), 6.35 (1H, s, CH), 7.18 (2H, m, aromatics), 7.36 (2H, m, aromatics), 13.2 (1H, broad s, OH). Anal. calcd for C$_{15}$H$_{18}$FNO$_5$: C, 57.87; H, 5.82; N, 4.50. Found: C, 57.88; H, 5.84; N, 4.30.

EXAMPLE 14

Compound 14-A: 3-Bromo-4-fluorobenzaldehyde O-methyloxime

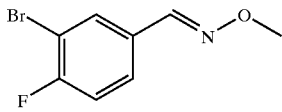

Reaction of 3-bromo-4-fluorobenzaldehyde with methoxylamine hydrochloride as described in the preparation of compound 3-A gave the title oxime ether as a clear oil (95% yield). $^1$HNMR indicated a 95:5 mixture of E- and Z-isomers. $^1$HNMR 400 MHz (CDCl$_3$) δ (ppm): (E-isomer) 3.97 (3H, s, OCH$_3$), 7.12 (1H, m, aromatics), 7.48 (1H, m, aromatic), 7.82 (1H, m, aromatic), 7.97 (1H, s, CH).

Compound 14-B: N-3-Bromo-4-fluorobenzyl-O-methyl-hydroxylamine

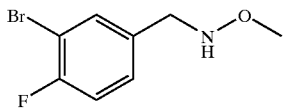

Reduction of 3-bromo-4-fluorobenzaldehyde O-methyloxime with sodium cyanoborohydride as described in the preparation of compound 3-B gave the title hydroxylamine as a clear oil (83% yield). $^1$HNMR 400 MHz (CDCl$_3$) δ (ppm): 3.48 (3H, s, OCH$_3$), 3.99 (2H, s, NCH$_2$), 7.08 (1H, m, aromatic), 7.27 (1H, m, aromatic), 7.57 (1H, m, aromatic). The hydrochloride salt was obtained as a white solid: mp 150–151° C. Anal. calcd. for C$_8$H$_9$BrFNO—HCl: C, 35.52; H, 3.73; N, 5.18. Found: C, 35.54; H, 3.61; N, 5.12.

Compound 14-C: N-(3-Bromo-4-fluoro-benzyl)-2-(2,2-dimethyl-5-oxo-[1,3]dioxolan-4-ylidene)-N-methoxy-acetamide

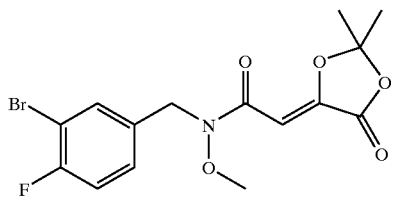

Reaction of (2,2-dimethyl-5-oxo-[1,3]dioxolan-4-ylidene)-acetyl chloride with N-3-bromo-4-fluorobenzyl-O-methyl-hydroxylamine as described in the preparation of compound 1-A gave the title amide as a white solid (100% yield): mp 117–119° C. (ethyl acetate-hexane). $^1$HNMR 400 MHz (CDCl$_3$) δ (ppm): 1.75 (6H, s, CH$_3$), 3.71 (3H, s, OCH$_3$), 4.76 (2H, s, NCH$_2$), 6.38 (1H, s, CH), 7.07 (1H, m, aromatic), 7.28 (1H, m, aromatic), 7.56 (1H, m, aromatic). Anal. calcd. for C$_{15}$H$_{15}$BrFNO$_5$: C, 46.41; H, 3.89; N, 3.61. Found: C, 46.43; H, 4.01; N, 3.53.

Compound 14: 3-[(3-Bromo-4-fluoro-benzyl)-methoxy-carbamoyl]-2-hydroxy-acrylic acid

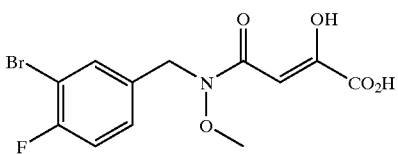

Saponification of N-(3-bromo-4-fluoro-benzyl)-2-(2,2-dimethyl-5-oxo-[1,3]dioxolan-4-ylidene)-N-methoxy-acetamide as described in the preparation of compound 1 gave the title material as white crystals (88% yield): mp 140–141° C. (ethyl acetate-hexane). $^1$HNMR 400 MHz (CDCl$_3$) δ (ppm): 3.74 (3H, s, OCH$_3$), 4.78 (2H, s, NCH$_2$), 6.56 (1H, s, CH), 7.10 (1H, m, aromatic), 7.26 (1H, m, aromatic), 7.53 (1H, m, aromatic). Anal. calcd. for C$_{12}$H$_{11}$BrFNO$_5$: C, 41.40; H, 3.18; N, 4.02. Found: C, 41.53; H, 3.26; N, 3.94.

EXAMPLE 15

Compound 15-A: 2-Methylbenzaldehyde O-methyloxime

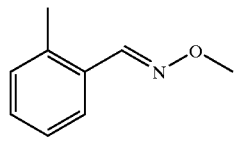

Reaction of 2-methylbenzaldehyde with methoxylamine hydrochloride as described in the preparation of compound 3-A gave the title oxime ether as a clear oil (96% yield). HPLC indicated a 95:5 mixture of E- and Z-isomers. $^1$HNMR 400 MHz (CDCl$_3$) δ (ppm): (E-isomer) 2.44 (3H, s, CH$_3$), 4.01 (3H, s, OCH$_3$), 7.19–7.28 (3H, m, aromatics), 7.73 (1H, m, aromatic), 8.36 (1H, s, CH).

Compound 15-B: N-2-Methylbenzyl-O-methyl-hydroxylamine

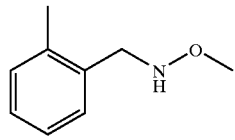

Reduction of 2-methylbenzaldehyde O-methyloxime with sodium cyanoborohydride as described in the preparation of compound 3-B gave the title hydroxylamine as a clear oil (83% yield). $^1$HNMR 400 MHz (CDCl$_3$) δ (ppm): 2.42 (3H, s, CH$_3$), 3.55 (3H, s, OCH$_3$), 4.11 (2H, s, NCH$_2$), 5.64 (1H, s, NH), 7.19–7.32 (4H, m, aromatics). The hydrochloride salt was obtained as a white solid: mp 148–150° C. Anal. calcd. for C$_9$H$_{13}$NO—HCl: C, 57.60; H, 7.51; N, 7.46. Found: C, 57.59; H, 7.69; N, 7.52.

Compound 15-C: 2-(2,2-Dimethyl-5-oxo-[1,3]dioxolan-4-ylidene)-N-methoxy-N-(2-methyl-benzyl)-acetamide

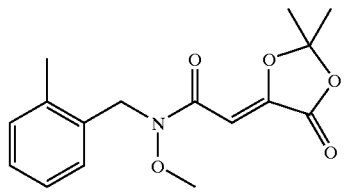

Reaction of (2,2-dimethyl-5-oxo-[1,3]dioxolan-4-ylidene)-acetyl chloride with N-(2-methylbenzyl)-O-methyl-hydroxylamine as described in the preparation of compound 1-A gave the title amide as white crystals (100% yield): mp 96–97° C. (ethyl acetate-hexane). $^1$HNMR 400 MHz (CDCl$_3$) δ (ppm): 1.78 (6H, s, CH$_3$), 2.4 (3H, s, CH$_3$), 3.59 (3H, s, OCH$_3$), 4.89 (2H, s, NCH$_2$), 6.44 (1H, s, CH), 7.2–7.28 (4H, m, aromatics). Anal. calcd. for C$_{16}$H$_{19}$NO$_5$: C, 62.94; H, 6.27; N, 4.59. Found: C, 62.90; H, 6.21; N, 4.52.

Compound 15: 2-Hydroxy-3-[methoxy-(2-methyl-benzyl)-carbamoyl]-acrylic acid

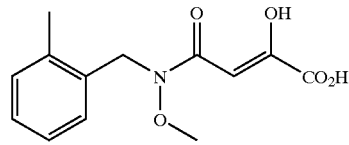

Saponification of 2-(2,2-dimethyl-5-oxo-[1,3]dioxolan-4-ylidene)-N-methoxy-N-(2-methyl-benzyl)-acetamide as described in the preparation of compound 1 gave the title material as white crystals (100% yield): mp 85–87° C. (dec.)(ethyl acetate-hexane). $^1$HNMR 400 MHz (CDCl$_3$) δ (ppm): 2.39 (3H, s, CH$_3$), 3.63 (3H, s, OCH$_3$), 4.9 (2H, s, NCH$_2$), 6.6 (1H, s, CH), 7.22–7.28 (4H, m, aromatics). Anal. calcd. for C$_{13}$H$_{15}$NO$_5$: C, 58.86; H, 5.70; N, 5.28. Found: C, 58.59; H, 5.67; N, 5.14.

EXAMPLE 16

Compound 16-A: 4-Methoxybenzaldehyde O-methyloxime

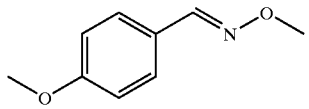

Reaction of 4-methoxybenzaldehyde with methoxylamine hydrochloride as described in the preparation of compound 3-A gave the title oxime ether as a clear oil (100% yield). $^1$HNMR indicated a 95:5 mixture of E- and Z-isomers. $^1$HNMR 400 MHz (CDCl$_3$) δ (ppm): (E-isomer) 3.83 (3H, s, OCH$_3$), 3.94 (3H, s, OCH$_3$), 6.89 (2H, m, aromatics), 7.52 (2H, m, aromatics), 8.05 (1H, s, CH).

Compound 16-B: N-4-Methoxybenzyl-O-methyl-hydroxylamine

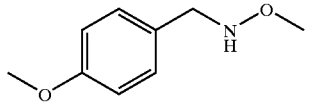

Reduction of 4-methoxybenzaldehyde O-methyloxime with sodium cyanoborohydride as described in the preparation of compound 3-B gave the title hydroxylamine as a clear oil (96% yield). $^1$HNMR 400 MHz (CDCl$_3$) δ (ppm): 3.49 (3H, s, OCH$_3$), 3.79 (3H, s, OCH$_3$), 3.98 (2H, s, NCH$_2$), 5.62 (1H, broad s, NH), 6.86 (2H, m, aromatics), 7.25 (2H, m, aromatics). The hydrochloride salt was obtained as a white solid: mp 157–158° C. (dec.). Anal. calcd. for C$_9$H$_{13}$NO$_2$—HCl: C, 53.03; H, 6.92; N, 6.87. Found: C, 53.14; H, 6.76; N, 6.80.

Compound 16-C: 2-(2,2-Dimethyl-5-oxo-[1,3]dioxolan-4-ylidene)-N-methoxy-N-(4-methoxy-benzyl)-acetamide

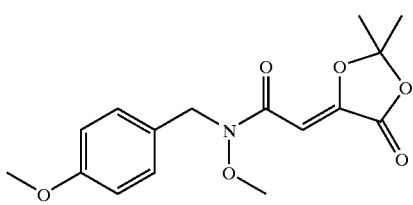

Reaction of (2,2-dimethyl-5-oxo-[1,3]dioxolan-4-ylidene)-acetyl chloride with N-(4-methoxybenzyl)-O-methyl-hydroxylamine as described in the preparation of compound 1-A gave the title amide as white crystals (97% yield): mp 113–114° C. (ethyl acetate-hexane). $^1$HNMR 400 MHz (CDCl$_3$) δ (ppm): 1.75 (6H, s, CH$_3$), 3.66 (3H, s, OCH$_3$), 3.79 (3H, s, OCH$_3$), 4.77 (2H, s, NCH$_2$), 6.38 (1H, s, CH), 6.85 (2H, m, aromatics), 7.29 (2H, m, aromatics). Anal. calcd. for C$_{16}$H$_{19}$NO$_6$: C, 59.80; H, 5.96; N, 4.35. Found: C, 59.87; H, 5.76; N, 4.17.

Compound 16: 2-Hydroxy-3-[methoxy-(4-methoxy-benzyl)-carbamoyl]-acrylic acid

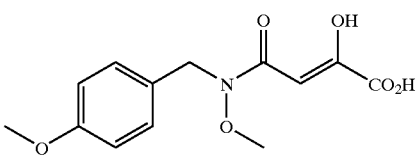

Saponification of 2-(2,2-dimethyl-5-oxo-[1,3]dioxolan-4-ylidene)-N-methoxy-N-(4-methoxy-benzyl)-acetamide as described in the preparation of compound 1 gave the title material as white crystals (95% yield): mp 83–86° C. (ethyl acetate-hexane). $^1$HNMR 400 MHz (CDCl$_3$) δ (ppm): 3.69 (3H, s, OCH$_3$), 3.80 (3H, s, OCH$_3$), 4.78 (2H, s, NCH$_2$), 6.54 (1H, s, CH), 6.88 (2H, m, aromatics), 7.27 (2H, m, aromatics). Anal. calcd. for C$_{13}$H$_{15}$NO$_6$: C, 55.51; H, 5.37; N, 4.98. Found: C, 55.45; H, 5.31; N, 4.79.

EXAMPLE 17

Compound 17-A: 2,4-Difluorobenzaldehyde O-methyloxime

Reaction of 2,4-difluorobenzaldehyde with methoxylamine hydrochloride as described in the preparation of compound 3-A gave the title oxime ether as a clear oil (80% yield). $^1$HNMR indicated a 95:5 mixture of E- and Z-isomers. $^1$HNMR 400 MHz (CDCl$_3$) δ (ppm): (E-isomer) 3.98 (3H, s, OCH$_3$), 6.79–6.91 (2H, m, aromatics), 7.79–7.85 (1H, m, aromatic), 8.24 (1H, s, CH).

Compound 17-B: N-2,4-Difluorobenzyl-O-methyl-hydroxylamine

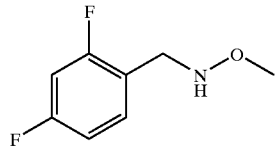

Reduction of 2,4-difluorobenzaldehyde O-methyloxime with sodium cyanoborohydride as described in the preparation of compound 3-B gave the title hydroxylamine as a clear oil (72% yield). $^1$HNMR 400 MHz (CDCl$_3$) δ (ppm): 3.51 (3H, s, OCH$_3$), 4.07 (2H, s, NCH$_2$), 6.78–6.88 (2H, m, aromatics), 7.32–7.38 (1H, m, aromatic). The hydrochloride salt was obtained as a white solid: mp 154–158° C. (dec.). Anal. calcd. for C$_8$H$_9$NO$_2$—HCl: C, 45.83; H, 4.80; N, 6.68. Found: C, 45.81; H, 4.84; N, 6.59.

Compound 17-C: N-(2,4-Difluoro-benzyl)-2-(2,2-dimethyl-5-oxo-[1,3]dioxolan-4-ylidene)-N-methoxy-acetamide

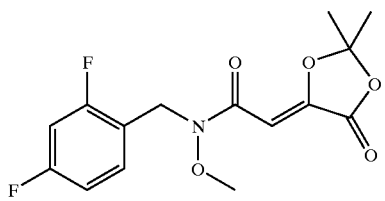

Reaction of (2,2-dimethyl-5-oxo-[1,3]dioxolan-4-ylidene)-acetyl chloride with N-2,4-difluorobenzyl-O-methyl-hydroxylamine as described in the preparation of compound 1-A gave the title amide as a white solid (97% yield): mp 120–125° C. (ethyl acetate-hexane). $^1$HNMR 400 MHz (CDCl$_3$) δ (ppm): 1.75 (6H, s, CH$_3$), 3.73 (3H, s, OCH$_3$), 4.86 (2H, s, NCH$_2$), 6.38 (1H, s, CH), 6.78–6.87 (2H, m, aromatics), 7.37–7.43 (1H, m, aromatic). Anal. calcd. for C$_{15}$H$_{15}$F$_2$NO$_5$: C, 55.04; H, 4.62; N, 4.28. Found: C, 55.03; H. 4.43; N, 4.17.

Compound 17: 3-[(2,4-Difluoro-benzyl)-methoxy-carbamoyl]-2-hydroxy-acrylic acid

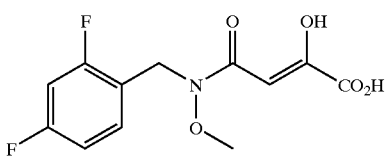

Saponification of N-(2,4-difluoro-benzyl)-2-(2,2-dimethyl-5-oxo-[1,3]dioxolan-4-ylidene)-N-methoxy-acetamide as described in the preparation of compound 1 gave the title material as white crystals (100% yield): mp 131–132° C. (ethyl acetate-hexane). $^1$HNMR 400 MHz (CDCl$_3$) δ (ppm): 3.74 (3H, s, OCH$_3$), 4.88 (2H, s, NCH$_2$), 6.55 (1H, s, CH), 6.81–6.90 (2H, m, aromatics), 7.31–7.37 (1H, m, aromatic). Anal. calcd. for C$_{12}$H$_{11}$F$_2$NO$_5$: C, 50.18; H, 3.86; N, 4.88. Found: C, 50.19; H, 3.87; N, 4.83.

EXAMPLE 18

Compound 18-A: 4-Carbomethoxybenzaldehyde O-methyloxime

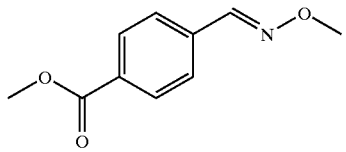

Reaction of methyl 4-formylbenzoate with methoxylamine hydrochloride as described in the preparation of compound 3-A gave the title oxime ether (96% yield) as a white solid (mixture of E- and Z-isomers). The E-isomer was obtained as white crystals from hexane; mp 66–67° C. (Lit. mp 65–66° C., Cooks, R. G.; Varvoglis, A. G. Org. Mass Spectrum., 5, 1971, 687). $^1$HNMR 400 MHz (DMSO-$d_6$) δ (ppm): (E-isomer) 3.86 (3H, s, OCH$_3$), 3.93 (3H, s, OCH$_3$), 7.75 (2H, d, aromatics), 7.98 (2H, d, aromatics), 8.32 (1H, s, CH).

Compound 18-B: N-4-Carbomethoxybenzyl-O-methyl-hydroxylamine

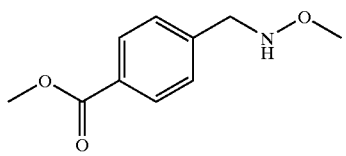

Reduction of 4-carbomethoxybenzaldehyde O-methyloxime with sodium cyanoborohydride as described in the preparation of compound 3-B gave the title hydroxylamine as an oil (53% yield). The hydrochloride salt was obtained as a white solid: mp 166–169° C. $^1$HNMR 400 MHz (DMSO-$d_6$) δ (ppm): 3.75 (3H, s, OCH$_3$), 3.86 (3H, s, OCH$_3$), 4.39 (2H, s, NCH$_2$), 7.65 (2H, d, aromatics), 7.97 (2H, d, aromatics). Anal. calcd for C$_{10}$H$_{13}$NO$_3$—HCl: C, 51.84; H, 6.09; N, 6.04. Found: C, 51.74; H, 6.01; N, 5.50.

Compound 18-C: 4-({[2-(2,2-Dimethyl-5-oxo-[1,3]dioxolan-4-ylidene)-acetyl]-methoxy-amino}-methyl)benzoic acid methyl ester

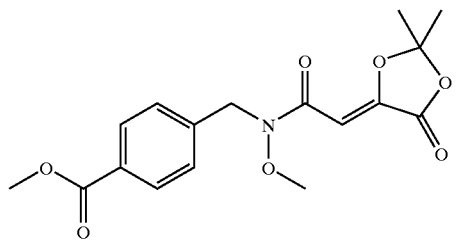

Reaction of (2,2-dimethyl-5-oxo-[1,3]dioxolan-4-ylidene)-acetyl chloride with N-4-carbomethoxybenzyl-O-methyl-hydroxylamine as described in the preparation of compound 1-A gave the title amide as a white solid (83% yield): mp 120° C. (dichloromethane-hexane). $^1$HNMR 400 MHz (CDCl$_3$) δ (ppm): 1.75 (6H, s, CH$_3$), 3.67 (3H, s, OCH$_3$), 3.91 (3H, s, OCH$_3$), 4.88 (2H, s, NCH$_2$), 6.40 (1H, s, CH), 7.42 (2H, d, aromatics), 8.0 (2H, d, aromatics). Anal. calcd for C$_{17}$H$_{19}$NO$_7$: C, 58.45; H, 5.48; N, 4.01. Found: C, 58.54; H, 5.55; N, 3.61.

Compound 18: 4-{[(3-Carboxy-3-hydroxy-acryloyl)-methoxy-amino]-methyl}-benzoic acid methyl ester

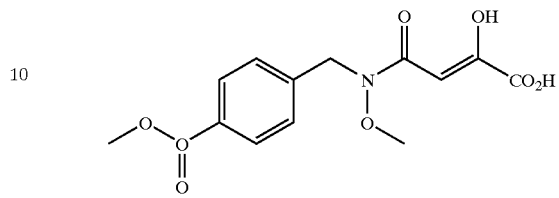

Saponification of 4-({[2-(2,2-dimethyl-5-oxo-[1,3]dioxolan-4-ylidene)-acetyl]-methoxy-amino}-methyl)benzoic acid methyl ester as described in the preparation of compound 1 gave the title material as white crystals (72% yield): mp 110–111° C. (dichloromethane-hexane). $^1$HNMR 400 MHz (CDCl$_3$) δ (ppm): 3.72 (3H, s, OCH$_3$), 3.92 (3H, s, OCH$_3$), 4.90 (2H, s, NCH$_2$), 6.58 (1H, s, CH),. 7.39 (2H, d, aromatics), 8.02 (2H, d, aromatics). Anal. calcd for C$_{14}$H$_{15}$NO$_7$: C, 53.74; H, 4.96; H, 4.48. Found: C, 53.61; H, 4.78; N, 4.44.

EXAMPLE 19

Compound 19-A: 3-Cyano-4-fluorobenzaldehyde O-methyloxime

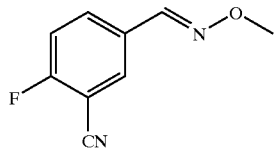

Reaction of 3-cyano-4-fluorobenzaldehyde with methoxylamine hydrochloride as described in the preparation of compound 3-A gave the title oxime ether as a clear oil after chromatography on silica gel (elution hexane-ethyl acetate 8:2) (94% yield). $^1$HNMR indicated a 93:7 mixture of E- and Z-isomers. $^1$HNMR 400 MHz (CDCl$_3$) δ (ppm): (E-isomer) 4.02 (3H, s, OCH$_3$), 7.26 (1H, m, aromatic), 7.85 (2H, m, aromatics), 8.03 (1H, s, CH).

Compound 19-B: N-(3-Cyano-4-fluorobenzyl)-O-methyl-hydroxylamine

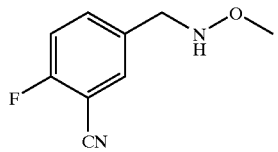

Reduction of 3-cyano-4-fluorobenzaldehyde O-methyloxime with sodium cyanoborohydride as described in the preparation of compound 3-B gave the title hydroxylamine as a clear oil after chromatography on silica gel (elution hexane-ethyl acetate 8: 2) (73% yield). $^1$HNMR 400 MHz (CDCl$_3$) δ (ppm): 3.46 (3H, s, OCH$_3$), 4.02 (2H, s, NCH$_2$), 7.18 (1H, t, aromatic), 7.58–7.66 (2H, m, aromatics). The hydrochloride salt was obtained as a white solid: mp 152–158° C. Anal. calcd for $C_9H_9FN_2O \cdot HCl$: C, 49.89; H, 4.65; N, 12.93. Found: C, 50.04; H, 4.64; N, 12.84.

Compound 19-C: N-(3-Cyano-4-fluoro-benzyl)-2-(2,2-dimethyl-5-oxo-[1,3]dioxolan-4-ylidene)-N-methoxy-acetamide

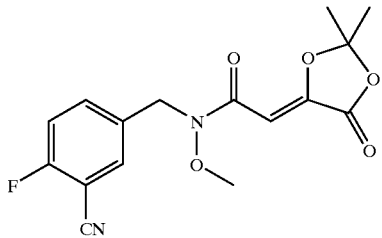

Reaction of (2,2-dimethyl-5-oxo-[1,3]dioxolan-4-ylidene)-acetyl chloride with N-(3-cyano-4-fluorobenzyl)-O-methyl-hydroxylamine as described in the preparation of compound 1-A gave the title amide as white crystals (97% yield): mp 119–120° C. (ethyl acetate-hexane). $^1$HNMR 400 MHz (CDCl$_3$) δ (ppm): 1.75 (6H, s, CH$_3$), 3.75 (3H, s, OCH$_3$), 4.78 (2H, s, NCH$_2$), 6.36 (1H, s, CH), 7.17 (1H, t, aromatic), 7.58–7.64 (2H, m, aromatics). Anal. calcd for $C_{16}H_{15}F_2NO_5$: C, 57.48; H, 4.52; N, 8.38. Found: C, 57.39; H, 4.61; N, 8.32.

Compound 19: 3-[(3-Cyano-4-fluoro-benzyl)-methoxy-carbamoyl]-2-hydroxy-acrylic acid

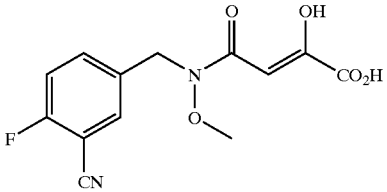

Saponification of N-(3-cyano-4-fluorobenzyl)-2-(2,2-dimethyl-5-oxo-[1,3]dioxolan-4-ylidene)-N-methoxy-acetamide as described in the preparation of compound 1 gave the title material as white crystals (93% yield): mp 144–151° C. (dec) (ethyl acetate-hexane). $^1$HNMR 400 MHz (DMSO-d$_6$) δ (ppm): (mixture of enol and keto forms, 7:3); enol form: 3.75 (3H, s, OCH$_3$), 4.92 (2H, s, NCH$_2$), 6.31 (1H, s, CH), 7.53 (1H, m, aromatic), 7.68–7.87 (2H, m, aromatics). Anal. calcd for: $C_{13}H_{11}FN_2O_5$: C, 53.07; H, 3.77; N, 9.52. Found: C, 52.93; H, 3.85; N, 9.45.

EXAMPLE 20

Compound 20-A: (4-Fluorobenzylideneaminooxy)-acetic acid tert-butyl ester

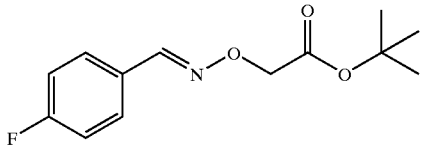

Condensation of 4-fluorobenzaldehyde with hydroxylamine hydrochloride followed by reaction with tert-butyl bromoacetate using the same procedure as described for compound 6-A gave the title oxime ether as a clear oil (84% yield). $^1$HNMR 400 MHz (CDCl$_3$) δ (ppm): 1.52 (9H, s, t-Bu), 4.61 (2H, s, OCH$_2$), 7.08 (2H, m, aromatics), 7.59 (2H, m, aromatics), 8.19 (1H, s, CH).

Compound 20-B: [N-(4-Fluorobenzyl)aminooxy]-acetic acid tert-butyl ester

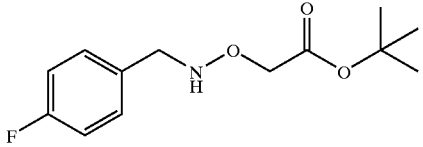

Reduction of (4-fluorobenzylideneaminooxy)-acetic acid tert-butyl ester as described in the preparation of compound 3-B gave the title hydroxylamine as a clear oil (65% yield). $^1$HNMR 400 MHz (C$_6$D$_6$) δ (ppm): 1.43 (9H, s, t-Bu), 3.84 (2H, d, J=5.6 Hz, NCH$_2$), 4.17 (2H, s, OCH$_2$), 6.39 (1H, broad t, NH), 6.86 (2H, m, aromatics), 7.05 (2H, m, aromatics).

Compound 20-C: [[2-(2,2-Dimethyl-5-oxo-[1,3]dioxolan-4-ylidene)-acetyl]-(4-fluoro-benzyl)-aminooxy]-acetic acid tert-butyl ester

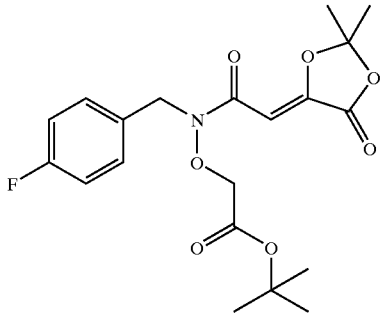

Reaction of (2,2-dimethyl-5-oxo-[1,3]dioxolan-4-ylidene)-acetyl chloride with [N-(4-fluorobenzyl)aminooxy]-acetic acid tert-butyl ester as described in the preparation of compound 1-A gave the title amide as white crystals (85% yield): mp 119–120° C. (ethyl acetate-hexane). 1HNMR 400 MHz (CDCl$_3$) δ (ppm): 1.48 (9H, s, t-Bu), 1.74 (6H, s, CH$_3$), 4.30 (2H, s, CH$_2$), 4.88 (2H, s, CH$_2$), 6.48 (1H, s, CH), 7.0 (2H, m, aromatics), 7.38 (2H, m, aromatics). Anal. calcd for $C_{20}H_{24}FNO_7$: C, 58.67; H, 5.91; N, 3.42. Found: C, 58.83; H, 5.92; N, 3.31.

Compound 20: 3-[tert-Butoxycarbonylmethoxy-(4-fluoro-benzyl)-carbamoyl]-2-hydroxy-acrylic acid

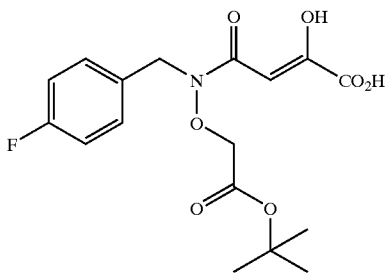

A solution of [[2-(2,2-dimethyl-5-oxo-[1,3]-dioxolan-4-ylidene)-acetyl]-(4-fluorobenzyl)-aminooxy]-acetic acid tert-butyl ester (0.10 g, 0.24 mmol) in tetrahydrofuran (3 ml) was treated at 0° C. with 0.48 ml (0.48 mmol) of 1 M aqueous lithium hydroxide. After 1 h, the reaction mixture was acidified with 1N hydrochloric acid and extracted with ethyl acetate. The organic phase was washed with brine, dried (magnesium sulphate) and evaporated in vacuo. Chromatograpy of the residual solid on Premisphere 5 μC-8 (gradient of acetonitrile in water) gave 0.037 g (41% yield) of the title material as a white solid: mp 73° C. (dec.). $^1$HNMR 400 MHz (CDCl$_3$) δ (ppm): 1.51 (9H, s t-Bu), 4.36 (2H, s, CH$_2$), 4.95 (2H, s, CH$_2$), 6.66 (1H, broad s, CH), 7.05 (2H, m, aromatics), 7.39 (2H, m, aromatics). HRMS (ES$^+$) calculated for C$_{17}$H$_{21}$FNO$_7$[M+H]$^+$: 370.130206. Found: 370.129173.

EXAMPLE 21

Compound 21-A: 4-Cyanobenzaldehyde O-methyloxime

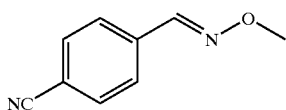

Reaction of 4-cyanobenzaldehyde with methoxylamine hydrochloride as described in the preparation of compound 3-A gave the title oxime ether as a white solid (96% yield). $^1$HNMR indicated a 95:5 mixture of E- and Z-isomers. $^1$HNMR 400 MHz (CDCl$_3$) δ (ppm): (E-isomer) 4.02 (3H, s, OCH$_3$), 7.07 (4H, m, aromatics), 8.06 (1H, s, CH).

Compound 21-B: N-4-Cyanobenzyl-O-methyl-hydroxylamine

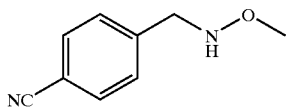

Reduction of 4-cyanobenzaldehyde O-methyloxime with sodium cyanoborohydride as described in the preparation of compound 3-B gave the title hydroxylamine as a clear oil (75% yield). $^1$HNMR 400 MHz (CDCl$_3$) δ (ppm): 3.48 (3H, s, OCH$_3$), 4.09 (2H, s, NCH$_2$), 7.48 (2H, m, aromatics), 7.63 (2H, m, aromatics). The hydrochloride salt was obtained as a white solid: mp 168° C. (dec.). Anal. calcd. for C$_9$H$_{10}$N$_2$O—HCl: C, 54.41; H, 5.58; N, 14.10. Found: C, 54.44; H, 5.62; N, 13.94.

Compound 21-C: N-(4-Cyano-benzyl)-2-(2,2-dimethyl-5-oxo-[1,3]dioxolan-4-ylidene)-N-methoxy-acetamide

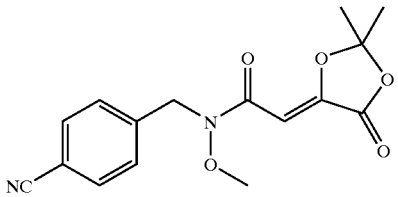

Reaction of (2,2-dimethyl-5-oxo-[1,3]dioxolan-4-ylidene)-acetyl chloride with N-(4-cyanobenzyl)-O-methyl-hydroxylamine as described in the preparation of compound 1-A gave the title amide as white crystals (99% yield): mp 148–149° C. (ethyl acetate-hexane). $^1$HNMR 400 MHz (CDCl$_3$) δ (ppm): 1.75 (6H, s, CH$_3$), 3.72 (3H, s, OCH$_3$), 4.86 (2H, s, NCH$_2$), 6.39 (1H, s, CH), 7.46 (2H, m, aromatics), 7.63 (2H, m, aromatics). Anal. calcd. for C$_{16}$H$_{16}$N$_2$O$_5$: C, 60.75; H, 5.10; N, 8.86. Found: C, 60.60; H, 4.91; N, 8.78.

Compound 21: 3-[(4-Cyano-benzyl)-methoxy-carbamoyl]-2-hydroxy-acrylic acid

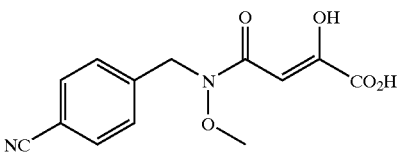

Saponification of N-(4-cyano-benzyl)-2-(2,2-dimethyl-5-oxo-[1,3]dioxolan-4-ylidene)-N-methoxy-acetamide as described in the preparation of compound 1 gave the title material as white crystals (92% yield): mp 135–137° C. (dec.)(ethyl acetate-hexane). $^1$HNMR 400 MHz (CDCl$_3$) δ (ppm): 3.75 (3H, s, OCH$_3$), 4.89 (2H, s, NCH$_2$), 6.58 (1H, s, CH), 7.43 (2H, m, aromatics), 7.66 (2H, m, aromatics). Anal. calcd. for C$_{13}$H$_{12}$N$_2$O$_5$: C, 56.52; H, 4.38; N, 10.14. Found: C, 56.70; H, 4.38; N, 10.07.

EXAMPLE 22

Compound 22-A: [[2-(2,2-Dimethyl-5-oxo-[1,3]-dioxolan-4-ylidene)-acetyl]-(4-fluorobenzyl)-aminooxy]-acetic acid.

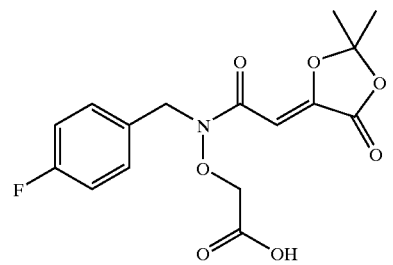

A solution [[2-(2,2-dimethyl-5-oxo-[1,3]-dioxolan-4-ylidene)-acetyl]-(4-fluorobenzyl)-aminooxy]-acetic acid tert-butyl ester (0.60 g, 1.46 mmol) in dichloromethane (15 ml) was treated at 22° C. with trifluoroacetic acid (4 ml) and the resulting mixture was stirred for 2h. Evaporation of the solvent in vacuo gave 0.517 g (100% yield) of the title material as a white solid. ¹HNMR 400 MHz (CDCl₃) δ (ppm): 1.79 (6H, s, CH₃), 4.41 (2H, s, CH₂), 4.88 (2H, s, CH₂), 6.4 (1H, broad, CH), 7.09 (2H, m, aromatics), 7.35 (2H, m, aromatics). HRMS (ES⁺) calculated for $C_{16}H_{17}FNO_7[M+H]^+$: 354.098905. Found: 354.098878.

Compound 22-B: N-Dimethylcarbamoylmethoxy-2-(2,2-dimethyl-5-oxo-[1,3]dioxolan-4-ylidene)-N-(4-fluoro-benzyl)-acetamide

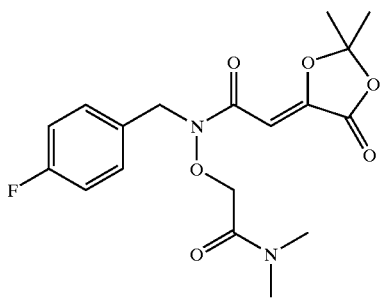

A solution [[2-(2,2-dimethyl-5-oxo-[1,3]-dioxolan-4-ylidene)-acetyl]-(4-fluorobenzyl)-aminooxy]-acetic acid (0.681 g, 1.93 mmol) in dichloromethane (20 ml) was treated at 22° C. with oxalyl chloride (0.34 ml, 3.9 mmol) and a trace of N,N-dimethylformamide and the resulting mixture was stirred for 1 h. The solvent and excess reagent were then evaporated in vacuo. The residual material was dissolved in dry dichloromethane (10 ml) and added dropwise to a cold (0° C.) solution of dimethylamine (0.18 g, 4.0 mmol) and pyridine (0.25 ml, 3.2 mmol ) in dichloromethane. After 2 h, the reaction mixture was diluted with ethyl acetate, washed with saturated sodium bicarbonate and brine and dried over anhydrous magnesium sulphate. Evaporation of the solvent in vacuo and crystallisation of the residue from a mixture of ethyl acetate and hexane gave 0.370 g (50% yield) of the title material as a white solid. ¹HNMR 400 MHz (CDCl₃) δ (ppm): 1.77 (6H, s, CH₃), 2.91 (3H, s, CH₃), 2.97 (3H, s, CH₃), 4.53 (2H, s, CH₂), 4.93 (2H, s, CH₂), 6.43 (1H, s, CH), 7.03 (2H, m, aromatics), 7.41 (2H, m, aromatics). HRMS (ES⁺) calculated for $C_{18}H_{22}FN_2O_6$ [M+H]⁺: 381.146190. Found: 381.146382.

Compound 22: 3-[Dimethylcarbamoylmethoxy-(4-fluoro-benzyl)-carbamoyl]-2-hydroxy-acrylic acid

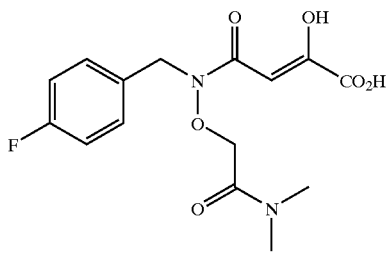

A solution of N-dimethylcarbamoylmethoxy-2-(2,2-dimethyl-5-oxo-[1,3]-dioxolan-4-ylidene)-N-(4-fluorobenzyl)-acetamide (0.065 g, 0.17 mmol in tetrahydrofuran (3 ml) was treated at 0° C. with 0.34 ml (0.34 mmol) of 1 M aqueous lithium hydroxide. After 1 h, the reaction mixture was acidified with 1N hydrochloric acid and extracted with ethyl acetate. The organic phase was washed with brine, dried (magnesium sulphate) and evaporated in vacuo. Crystallisation of the residual solid from a mixture of ethyl acetate and hexane gave 0.043 g (74% yield) of the title material as a white solid: mp 118–120° C. ¹HNMR 400 MHz (DMSO-d₆) δ (ppm); (mixture of enol and keto forms, 7:3); enol form: 2.83 (3H, s, NCH₃), 2.88 (3H, s, NCH₃), 4.79 (2H, s, CH₂), 4.94 (2H, s, CH₂), 6.47 (1H, s, CH), 7.18 (2H, m, aromatics), 7.38 (2H, m, aromatics), 13.2 (1H, broad, OH), 13.7 (1H, broad, OH). HRMS (ES⁺) calculated for $C_{15}H_{18}FN_2O_6[M+H]^+$: 341.114890. Found: 341.115095.

EXAMPLE 23

Compound 23-A: 4-Acetamidobenzaldehyde O-methyloxime

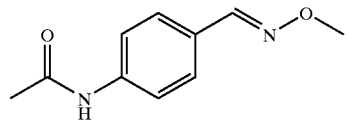

Reaction of 4-acetamidobenzaldehyde with methoxylamine hydrochloride as described in the preparation of compound 3-A gave the title oxime ether as a white solid (98% yield). ¹HNMR indicated a 95:5 mixture of E- to Z-isomers. ¹HNMR 400 MHz (CDCl₃) δ (ppm): (E-isomer) 2.19 (3H, s, CH₃), 3.96 (3H, s, OCH₃), 7.22 (1H, broad s, NH), 7.53 (4H, m, aromatics), 8.01 (1H, s, CH).

Compound 23-B: N-4-Acetamidobenzyl-O-methyl-hydroxylamine

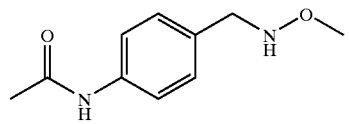

Reduction of 4-acetamidobenzaldehyde O-methyloxime with sodium cyanoborohydride as described in the preparation of compound 3-B gave the title hydroxylamine as a waxy solid (100% yield). ¹HNMR 400 MHz (CDCl₃) δ (ppm): 2.16 (3H, s, CH₃), 3.49 (3H, s, OCH₃), 4.00 (2H, s, NCH₂), 7.26 (1H, broad s, NH), 7.29 (2H, m, aromatics), 7.46 (2H, m, aromatics). The hydrochloride salt was obtained as a white solid: mp 186–188° C. (dec.). Anal. calcd. for $C_{10}H_{14}N_2O_2$—HCl—H₂O: C, 50.87; H, 6.66; N, 11.87. Found: C, 50.77; H, 6.44; N, 12.16.

Compound 23-C: N-(4-Acetylamino-benzyl)-2-(2,2-dimethyl-5-oxo-[1,3]-dioxolan-4-ylidene)-N-methoxy-acetamide

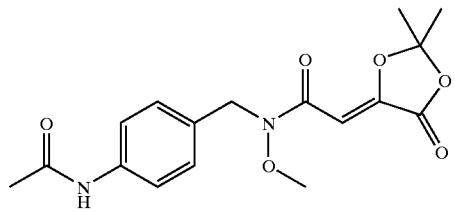

Reaction of (2,2-dimethyl-5-oxo-[1,3]dioxolan-4-ylidene)-acetyl chloride with N-(4-acetamidobenzyl)-O- methyl-hydroxylamine as described in the preparation of compound 1-A gave the title amide as white crystals (92% yield): mp 212–215° C. (dec.) (dichloromethane-hexane). $^1$HNMR 400 MHz (CDCl$_3$) δ (ppm): 1.73 (6H, s, CH$_3$), 2.16 (3H, s, CH$_3$), 3.67 (3H, s, OCH$_3$), 4.78 (2H, s, NCH$_2$), 6.39 (1H, s, CH), 7.32 (3H, m, aromatics and NH), 7.45 (2H, m, aromatics). Anal. calcd. for C$_{17}$H$_{20}$N$_2$O$_6$: C, 57.87; H, 5.86; N, 7.94. Found: C, 57.76; H, 5.68; N, 8.51.

Compound 23: 3-[(4-Acetylamino-benzyl)-methoxy-carbamoyl]-2-hydroxy-acrylic acid

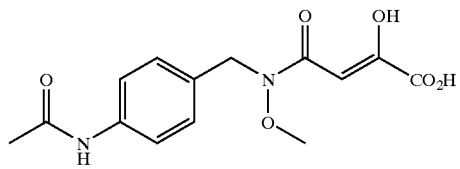

Saponification of N-(4-acetylamino-benzyl)-2-(2,2-dimethyl-5-oxo-[1,3]-dioxolan-4-ylidene)-N-methoxy-acetamide as described in the preparation of compound 1 gave the title material as white crystals (83% yield): mp 155° C. (dec.)(ethyl acetate). $^1$HNMR 400 MHz (DMSO-d$_6$) δ (ppm): mixture of rotamers and keto-enol isomers; 2.02 (3H, s, CH$_3$), 3.71 (3H, s, OCH$_3$), 4.8 (2H, s, NCH$_2$), 6.30 (1H, s, CH), 7.2 (2H, m, aromatics), 7.52 (2H, m, aromatics), 9.93 (OH). Anal. calcd. for C14H$_{16}$N$_2$O$_6$: C, 54.54; H, 5.23; N, 9.09. Found: C, 54.06; H, 5.57; N, 8.39.

EXAMPLE 24

Compound 24: 3-[Carboxymethoxy-(4-fluoro-benzyl)-carbamoyl]-2-hydroxy-acrylic acid

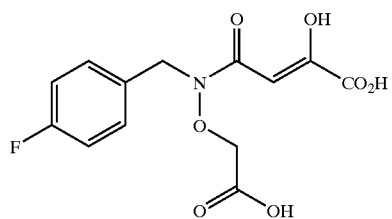

A solution of [[2-(2,2-dimethyl-5-oxo-[1,3]-dioxolan-4-ylidene)-acetyl]-(4-fluorobenzyl)-aminooxy]-acetic acid (0.20 g, 0.56 mmol) in tetrahydrofuran (5 ml) was treated at 0° C. with 1.7 ml (1.7 mmol) of 1 M aqueous lithium hydroxide. After 2 h, the reaction mixture was acidified with 1N hydrochloric acid and extracted with ethyl acetate. The organic layer was washed with brine, dried (magnesium sulphate) and evaporated in vacuo. Crystallisation of the residual solid from a mixture of ethyl acetate and hexane gave 0.083 g (47% yield) of the title material as a white solid: mp 135–138° C. $^1$HNMR 400 MHz (DMSO-d$_6$) δ (ppm): (mixture of enol and keto forms, 7:3); enol form: 4.65 (2H, s, CH$_2$), 4.92 (2H, s, CH$_2$), 6.51 (1H, s, CH), 7.18 (2H, m, aromatics), 7.37 (2H, m, aromatics), 13.17 (1H, broad, OH). Anal. calcd for C$_{13}$H$_{12}$FNO$_7$: C, 49.85; H, 3.86; N, 4.47. Found: C, 49.83; H, 3.90; N, 4.37.

EXAMPLE 25

Compound 25-A: 4-Methyl-benzaldehyde O-methyl-oxime

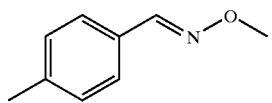

Reaction of 4-methylbenzaldehyde with methoxylamine hydrochloride as described in the preparation of compound 3-A gave the title oxime as a clear oil (95% yield), bp 80–85° C./4 torr (bulb to bulb distillation, air bath temperature). HPLC indicated a 94:6 mixture of E- and Z-isomers. $^1$HNMR 400 MHz (CDCl$_3$) δ (ppm): (E-isomer) 2.39 (3H, s, CH$_3$), 3.99 (3H, s, OCH$_3$), 7.2 (2H, d, J=8.1 Hz, aromatics), 7.5 (2H, d, J=8.1 Hz, aromatics), 8.07 (1H, s, CH).

Compound 25-B: O-Methyl-N-(4-methyl-benzyl)-hydroxylamine

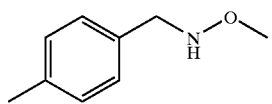

Reduction of 4-methylbenzaldehyde O-methyloxime with sodium cyanoborohydride as described in the preparation of compound 3-B gave the title hydroxylamine as a clear oil (76% yield): bp 70–80° C./3.5 torr (bulb to bulb distillation, air bath temperature). $^1$HNMR 400 MHz (CDCl$_3$) δ (ppm): 2.36 (3H, s, CH$_3$), 3.54 (3H, s, OCH$_3$), 4.04 (2H, s, NCH$_2$), 5.7 (broad, NH), 7.17 (2H, d, J=8.1 Hz, aromatics), 7.26 (2H, d, J=8.1 Hz, aromatics). The hydrochloride salt was obtained as a white solid: mp 162–164° C. Anal. calcd for C$_9$H$_{13}$NO—HCl: C, 57.60; H, 7.51; N, 7.46. Found: C, 57.87; H, 7.45; N, 7.25.

Compound 25-C: 2-(2,2-Dimethyl-5-oxo-[1,3] dioxolan-4-ylidene)-N-methoxy-N-(4-methyl-benzyl)-acetamide

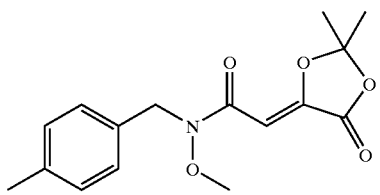

Reaction of (2,2-dimethyl-5-oxo-[1,3]dioxolan-4-ylidene)-acetyl chloride with N-(4-methylbenzyl)-O-methyl-hydroxylamine as described in the preparation of compound 1-A gave the title amide as white crystals (78% yield): mp 108–110° C. (ethyl acetate-hexane). $^1$HNMR 400 MHz (CDCl$_3$) δ (ppm): 1.92 (6H, s, CH$_3$), 2.5 (3H, s, CH$_3$), 3.84 (3H, s, OCH$_3$), 4.97 (2H, s, NCH$_2$), 6.57 (1H, s, CH), 7.31 (2H, d, J=8.1 Hz, aromatics), 7.42 (2H, d, J=8.1 Hz, aromatics). Anal. calcd for C$_{16}$H$_{19}$NO$_5$: C, 62.94; H, 6.27; N, 4.59. Found: C, 63.14; H, 5.93; N, 4.34.

Compound 25: 2-Hydroxy-3-[methoxy-(4-methyl-benzyl)-carbamoyl]-acrylic acid

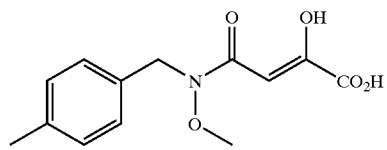

Saponification of 2-(2,2-dimethyl-5-oxo-[1,3]dioxolan-4-ylidene)-N-methoxy-N-(4-methyl-benzyl)-acetamide as described in the preparation of compound 1 gave the title material as a white solid (95% yield): mp 108–111° C. (dec) (ethyl acetate-hexane). $^1$HNMR 400 MHz (CDCl$_3$) δ (ppm): 2.37 (3H, s, CH$_3$), 3.72 (3H, s, OCH$_3$), 4.83 (2H, s, NCH$_2$), 6.59 (1H, s, CH), 7.18 (2H, d, J=8.1 Hz, aromatics), 7.25 (2H, d, J=8.1 Hz, aromatics). Anal. calcd for C$_{13}$H$_{15}$NO$_5$: C, 58.86; H, 5.70; N, 5.28. Found: C, 58.66; H, 5.71; N, 5.23.

EXAMPLE 26

Compound 26-A: 4-Fluoro-3-methyl-benzaldehyde O-methyl-oxime

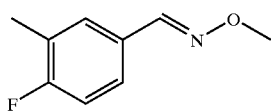

Reaction of 4-fluoro-3-methyl-benzaldehyde with methoxylamine hydrochloride as described in the preparation of compound 3-A gave the title oxime ether as a clear oil after chromatography on silica gel (elution hexane-ethyl acetate 8:2) (100% yield). $^1$HNMR indicated a 9:1 mixture of E- and Z-isomers. $^1$HNMR 400 MHz (CDCl$_3$) δ (ppm): (E-isomer) 2.29 (3H, broad s, CH$_3$), 3.96 (3H, s, OCH$_3$), 7.0 (1H, m, aromatic), 7.34 (1H, m, aromatic), 7.4 (1H, m, aromatic), 8.0 (1H, s, CH).

Compound 26-B: N-(4-Fluoro-3-methyl-benzyl)-O-methyl-hydroxylamine

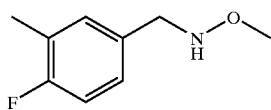

Reduction of 4-fluoro-3-methyl-benzaldehyde O-methyloxime with sodium cyanoborohydride as described in the preparation of compound 3-B gave the title hydroxylamine as a clear oil after chromatography on silica gel (elution hexane-ethyl acetate 8:2) (94% yield). $^1$HNMR 400 MHz (CDCl$_3$) δ (ppm): 2.27 (3H, broad s, CH$_3$), 3.50 (3H, s, OCH$_3$), 3.97 (2H, broad s, NCH$_2$), 5.67 (1H, broad, NH), 6.95 (1H, m, aromatic), 7.11–7.17 (2H, m, aromatics. The hydrochloride salt was obtained as a white solid: mp 162° C. Anal. calcd for C$_9$H$_{12}$FNO—HCl: C, 52.56; H, 6.37; N, 6.81. Found: C, 52.80; H, 6.33; N, 6.70.

Compound 26-C: 2-(2,2-Dimethyl-5-oxo-[1,3]dioxolan-4-ylidene)-N-(4-Fluoro-3-methyl-benzyl)-N-methoxy-acetamide

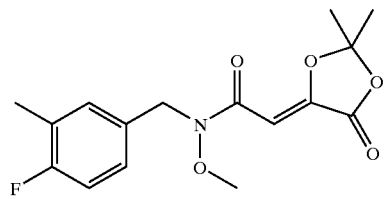

Reaction of (2,2-dimethyl-5-oxo-[1,3]dioxolan-4-ylidene)-acetyl chloride with N-(4-fluoro-3-methyl-benzyl)-O-methyl-hydroxylamine as described in the preparation of compound 1-A gave the title amide as white crystals (95% yield): mp 107–108° C. (ethyl acetate-hexane). $^1$HNMR 400 MHz (CDCl$_3$) δ (ppm): 1.75 (6H, s, CH$_3$), 2.26 (3H, broad s, CH$_3$), 3.69 (3H, s, OCH$_3$), 4.75 (2H, s, NCH$_2$), 6.39 (1H, s, CH), 6.95 (1H, m, aromatic), 7.13–7.19 (2H, m, aromatics). Anal. calcd for C$_{16}$H$_{18}$FNO$_5$: C, 59.43; H, 5.61; N, 4.33. Found: C, 59.24; H, 5.47; N 4.29.

Compound 26: 3-[(4-Fluoro-3-methyl-benzyl)-methoxy-carbamoyl]-2-hydroxy-acrylic acid

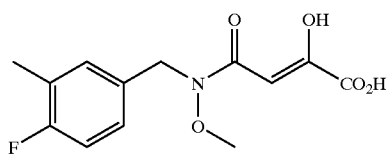

Saponification of 2-(2,2-dimethyl-5-oxo-[1,3]dioxolan-4-ylidene)-N-(4-fluoro-3-methyl-benzyl)-N-methoxy-acetamide as described in the preparation of compound 1 gave the title material as white crystals (96% yield): mp 120–122° C. (ethyl acetate-hexane). $^1$HNMR 400 MHz (CDCl$_3$) δ (ppm): 2.27 (3H, broad s, CH$_3$), 3.71 (3H, s, OCH$_3$), 4.77 (2H, s, NCH$_2$), 6.56 (1H, s, CH), 6.97 (1H, m, aromatic), 7.1–7.15 (2H, m, aromatics). Anal. calcd for C$_{13}$H$_{14}$FNO$_5$: C, 55.12; H, 4.98; N, 4.94. Found: C, 55.06; H, 4.91; N, 4.83.

EXAMPLE 27

Compound 27-A: 3-Fluoro-4-methyl-benzaldehyde O-methyl-oxime

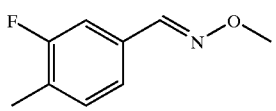

Reaction of 3-fluoro-4-methyl-benzaldehyde with methoxylamine hydrochloride as described in the preparation of compound 3-A gave the title oxime ether as a clear oil (94% yield). $^1$HNMR indicated a 9:1 mixture of E- and Z-isomers. $^1$HNMR 400 MHz (CDCl$_3$) δ (ppm): (E-isomer) 2.28 (3H, broad s, CH$_3$), 3.97 (3H, s, OCH$_3$), 7.15–7.29 (3H, m, aromatics), 7.99 (1H, s, CH).

Compound 27-B: N-(3-Fluoro-4-methyl-benzyl)-O-methyl-hydroxylamine

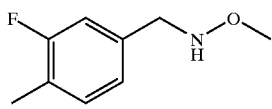

Reduction of 3-fluoro-4-methyl-benzaldehyde O-methyloxime with sodium cyanoborohydride as described in the preparation of compound 3-B gave the title hydroxylamine as a clear oil after chromatography on silica gel (elution hexane-ethyl acetate 8:2) (57% yield). $^1$HNMR 400 MHz (CDCl$_3$) δ (ppm): 2.25 (3H, broad s, CH$_3$), 3.50 (3H, s, OCH$_3$), 3.99 (2H, broad s, NCH$_2$), 5.71 (1H, broad, NH), 7.01 (2H, m, aromatics), 7.13 (1H, m, aromatic). The hydrochloride salt was obtained as a white solid: mp 140–142° C. Anal. calcd for C$_9$H$_{12}$FNO—HCl: C, 52.56; H, 6.37; N, 6.81. Found: C, 52.63; H, 6.30; N, 6.78.

Compound 27-C: 2-(2,2-Dimethyl-5-oxo-[1,3]dioxolan-4-ylidene)-N-(3-fluoro-4-methyl-benzyl)-N-methoxy-acetamide

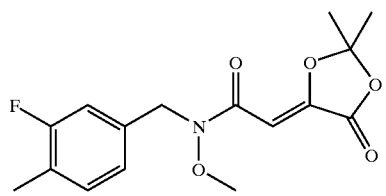

Reaction of (2,2-dimethyl-5-oxo-[1,3]dioxolan-4-ylidene)-acetyl chloride with N-(3-fluoro-4-methyl-benzyl)-O-methyl-hydroxylamine as described in the preparation of compound 1-A gave the title amide as white crystals (100% yield): mp 131° C. (ethyl acetate-hexane). $^1$HNMR 400 MHz (CDCl$_3$) δ (ppm): 1.75 (6H, s, CH$_3$), 2.25 (3H, broad s, CH$_3$), 3.69 (3H, s, OCH$_3$), 4.77 (2H, s, NCH$_2$), 6.39 (1H, s, CH), 7.0–7.03 (2H, m, aromatics), 7.13 (1H, m, aromatic). Anal. calcd for C$_{16}$H$_{18}$FNO$_5$: C, 59.43; H, 5.61; N, 4.33. Found: C, 59.51; H, 5.60; N, 4.24.

Compound 27: 3-[(3-Fluoro-4-methyl-benzyl)-methoxy-carbamoyl]-2-hydroxy-acrylic acid

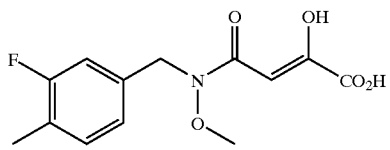

Saponification of 2-(2,2-dimethyl-5-oxo-[1,3]dioxolan-4-ylidene)-N-(3-fluoro-4-methyl-benzyl)-N-methoxy-acetamide as described in the preparation of compound 1 gave the title material as white crystals (100% yield): mp 99° C. (ethyl acetate-hexane). $^1$HNMR 400 MHz (CDCl$_3$) δ (ppm): 2.26 (3H, broad s, CH$_3$), 3.72 (3H, s, OCH$_3$), 4.79 (2H, s, NCH$_2$), 6.56 (1H, s, CH), 7.0 (2H, m, aromatics), 7.16 (1H, m, aromatic). Anal. calcd for C$_{13}$H$_{14}$FNO$_5$: C, 55.12; H, 4.98; N, 4.94. Found: C, 54.82; H, 4.90; N, 4.80.

EXAMPLE 28

Compound 28-A: 4-Trifluoromethyl-benzaldehyde O-methyloxime

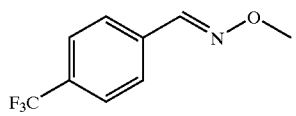

Reaction of 4-trifluoromethylbenzaldehyde with methoxylamine hydrochloride as described in the preparation of compound 3-A gave the title oxime ether as a clear oil (100% yield). $^1$HNMR indicated a 9:1 mixture of E- and Z-isomers. $^1$HNMR 400 MHz (CDCl$_3$) δ (ppm): (E-isomer) 4.00 (3H, s, OCH$_3$), 7.62 (2H, m, aromatics), 7.69 (2H, m, aromatics), 8.08 (1H, s, CH).

Compound 28-B: O-Methyl-N-(4-trifluoromethyl-benzyl)-hydroxylamine

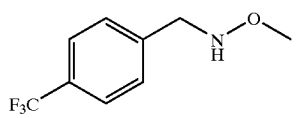

Reduction 4-trifluoromethyl-benzaldehyde O-methyloxime of with sodium cyanoborohydride as described in the preparation of compound 3-B gave the title hydroxylamine as a clear oil (73% yield). $^1$HNMR 400 MHz (CDCl$_3$) δ (ppm): 3.49 (3H, s, OCH$_3$), 4.09 (2H, s, NCH$_2$), 5.80 (1H, broad s, NH), 7.48 (2H, m, aromatics), 7.60 (2H, m, aromatics). The hydrochloride salt was obtained as a white solid: mp 132–133° C. Anal. calcd for C$_9$H$_{10}$F$_3$NO—HCl: C, 44.74; H, 4.59; N, 5.80. Found: C, 44.71; H, 4.53; N, 5.68.

Compound 28-C: 2-(2,2-Dimethyl-5-oxo-[1,3]dioxolan-4-ylidene)-N-methoxy-N-(4-trifluoromethyl-benzyl)-acetamide

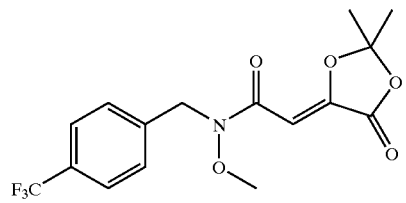

Reaction of (2,2-dimethyl-5-oxo-[1,3]dioxolan-4-ylidene)-acetyl chloride with O-methyl-N-(4-trifluoromethyl-benzyl)-hydroxylamine as described in the preparation of compound 1-A gave the title amide as white crystals (97% yield): mp 110° C. (ethyl acetate-hexane). $^1$HNMR 400 MHz (CDCl$_3$) δ (ppm): 1.76 (6H, s, CH$_3$), 3.71 (3H, s, OCH$_3$), 4.87 (2H, s, NCH$_2$), 6.40 (1H, s, CH), 7.47 (2H, m, aromatics), 7.59 (2H, m, aromatics). Anal. calcd for C$_{16}$H$_{16}$F$_3$NO$_5$: C, 53.49; H, 4.49; N, 3.90. Found: C, 53.48; H, 4.53; N, 3.83.

Compound 28: 2-Hydroxy-3-[methoxy-(4-trifluoromethyl-benzyl)-carbamoyl]-acrylic acid

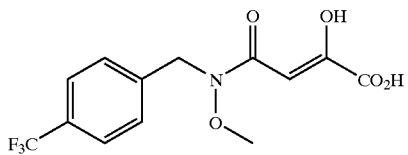

Saponification of 2-(2,2-dimethyl-5-oxo-[1,3]dioxolan-4-ylidene)-N-methoxy-N-(4-trifluoromethyl-benzyl)-acetamide as described in the preparation of compound 1 gave the title material as white crystals (94% yield): mp 108–110° C. (ethyl acetate-hexane). $^1$HNMR 400 MHz (CDCl$_3$) δ (ppm): 3.74 (3H, s, OCH$_3$), 4.90 (2H, s, NCH$_2$), 6.58 (1H, s, CH), 7.45 (2H, m, aromatics), 7.62 (2H, m, aromatics). Anal. calcd for C$_{13}$H$_{12}$F$_3$NO$_5$: C, 48.91; H, 3.78; N, 4.38. Found: C, 48.96; H, 3.79; N, 4.29.

EXAMPLE 29

Compound 29-A: 4-Fluoro-2-trifluoromethyl-benzaldehyde O-methyloxime

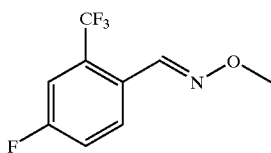

Reaction of 4-fluoro-2-trifluoromethyl-benzaldehyde with methoxylamine hydrochloride as described in the preparation of compound 3-A gave the title oxime ether as a clear oil (93% yield). $^1$HNMR indicated a 92:8 mixture of E- and Z-isomers. $^1$HNMR 400 MHz (CDCl$_3$) δ (ppm): (E-isomer) 4.00 (3H, s, OCH$_3$), 7.25 (1H, m, aromatic), 7.37 (1H, m, aromatic), 8.08 (1H, m, aromatic), 8.36 (1H, broad s, CH).

Compound 29-B: N-(4-Fluoro-2-trifluoromethyl-benzyl)-O-methyl-hydroxylamine

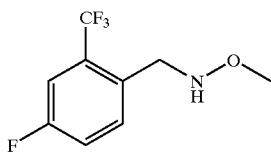

Reduction of 4-fluoro-2-trifluoromethyl-benzaldehyde O-methyloxime with sodium cyanoborohydride as described in the preparation of compound 3-B gave the title hydroxylamine as a clear oil after chromatography on silica gel (elution hexane-ethyl acetate 8:2) (35% yield). $^1$HNMR 400 MHz (CDCl$_3$) δ (ppm): 3.55 (3H, s, OCH$_3$), 4.21 (2H, s, NCH$_2$), 5.76 (1H, broad, NH), 7.26 (1H, m, aromatic), 7.38 (1H, m, aromatic), 7.64 (1H, m, aromatic). The hydrochloride salt was obtained as a white solid: mp 138–140° C. Anal. calcd for C$_9$H$_9$F$_4$NO—HCl: C, 41.64; H, 3.88; N, 5.39. Found: C, 41.49; H, 3.68; N, 5.26.

Compound 29: 2-(2,2-Dimethyl-5-oxo-[1,3]dioxolan-4-ylidene)-N-(4-fluoro-2-trifluoromethyl-benzyl)-N-methoxy-acetamide.

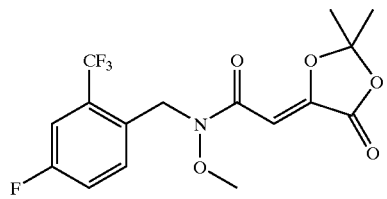

Reaction of (2,2-dimethyl-5-oxo-[1,3]dioxolan-4-ylidene)-acetyl chloride with N-(4-fluoro-2-trifluoromethyl-benzyl)-O-methyl-hydroxylamine as described in the preparation of compound 1-A gave the title amide as white crystals (98% yield): mp 129–130° C. (ethyl acetate-hexane). $^1$HNMR 400 MHz (CDCl$_3$) δ (ppm): 1.76 (6H, s, CH$_3$), 3.69 (3H, s, OCH$_3$), 5.04 (2H, s, NCH$_2$), 6.45 (1H, s, CH), 7.21 (1H, m, aromatic), 7.37 (1H, m, aromatic), 7.47 (1H, m, aromatic). Anal. calcd for C$_{16}$H$_{15}$F$_4$NO$_5$: C, 50.94; H, 4.01; N, 3.71. Found: C ,50.96; H, 4.07; N, 3.66.

EXAMPLE 30

Compound 30-A: 2-Chloro-4-fluoro-benzaldehyde O-methyloxime

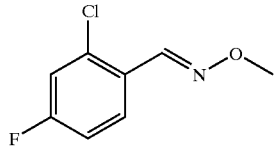

Reaction of 2-chloro-4-fluoro-benzaldehyde with methoxylamine hydrochloride as described in the preparation of compound 3-A gave the title oxime ether as a clear oil (93% yield). $^1$HNMR indicated a 9:1 mixture of E- and Z-isomers. $^1$HNMR 400 MHz (CDCl$_3$) δ (ppm): (E-isomer) 3.99 (3H, s, OCH$_3$), 6.99 (1H, m, aromatic), 7.12 (1H, m, aromatic), 7.87 (1H, m, aromatic), 8.41 (1H, s, CH).

Compound 30-B: N-(2-Chloro-4-fluoro-benzyl)-O-methyl-hydroxylamine

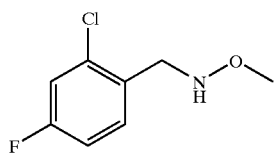

Reduction of 2-chloro-4-fluoro-benzaldehyde O-methyloxime with sodium cyanoborohydride as described in the preparation of compound 3-B gave the title hydroxylamine as a clear oil after chromatography on silica gel (elution dichloromethane-ethyl acetate 95:5) (54% yield). $^1$HNMR 400 MHz (CDCl$_3$) δ (ppm): 3.55 (3H, s, OCH$_3$), 4.16 (2H, s, NCH$_2$), 6.99 (1H, m, aromatic), 7.15 (1H, dd, J=2.5 Hz and J=8.6 Hz, aromatic), 7.41 (1H, dd, J=6.0 Hz and J=8.6 Hz, aromatic). The hydrochloride salt was obtained as a white solid: mp 159° C. Anal. calcd for C$_8$H$_9$ClFNO—HCl: C, 42.50; H, 4.46; N, 6.20. Found: C, 42.50; H, 4.36; N, 5.98.

Compound 30-C: N-(2-Chloro-4-fluoro-benzyl)-2-(2,2-dimethyl-5-oxo-[1,3]dioxolan-4-ylidene)-N-methoxy-acetamide

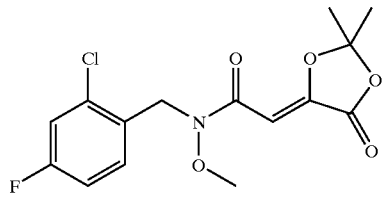

Reaction of (2,2-dimethyl-5-oxo-[1,3]dioxolan-4-ylidene)-acetyl chloride with N-(2-chloro-4-fluoro-benzyl)-O-methyl-hydroxylamine as described in the preparation of compound 1-A gave the title amide as white crystals (97% yield): mp 127–128° C. (ethyl acetate-hexane). $^1$HNMR 400 MHz (CDCl$_3$) δ (ppm): 1.76 (6H, s, CH$_3$), 3.70 (3H, s, OCH$_3$), 4.95 (2H, s, NCH$_2$), 6.41 (1H, s, CH), 6.96 (1H, m, aromatic), 7.13 (1H, dd, J=2.5 Hz and J=8.7 Hz, aromatic), 7.38 (1H, dd, J=6.1 Hz and J=8.6 Hz, aromatic). Anal. calcd for C$_{15}$H$_{15}$ClFNO$_5$: C, 52.41; H, 4.39; N, 4.07. Found: C, 52.49; H, 4.15; N, 3.76.

Compound 30: 3-[(2-Chloro-4-fluoro-benzyl)-methoxy-carbamoyl]-2-hydroxy-acrylic acid

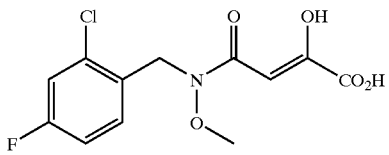

Saponification of N-(2-chloro-4-fluoro-benzyl)-2-(2,2-dimethyl-5-oxo-[1,3]dioxolan-4-ylidene)-N-methoxy-acetamide as described in the preparation of compound 1 gave the title material as white crystals (98% yield): mp 140–143° C. (ethyl acetate-hexane). $^1$HNMR 400 MHz (DMSO-d$_6$) δ (ppm): mixture of keto-enol forms 25:75; enol: 3.72 (3H, s, OCH$_3$), 4.96 (2H, s, NCH$_2$), 6.33 (1H, s, CH),. 7.25 (1H, m, aromatic), 7.41 (1H, m, aromatic), 7.50 (1H, m, aromatic); keto: 3.64 (3H, s OCH$_3$), 3.98 (2H, s, CH$_2$), 4.84 (2H, s, CH$_2$). Anal. calcd for C$_{12}$H$_{11}$ClFNO$_5$: C, 47.46; H, 3.65; N, 4.61. Found: C, 47.45; H, 3.61; N, 4.56.

EXAMPLE 31

Compound 31-A: 2-Isopropoxy-benzaldehyde O-methyloxime

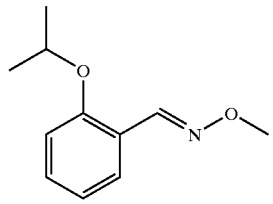

Reaction of 2-isopropoxybenzaldehyde (Hach, Collect. Czech. Commun., 23, 1958, 1902–1907) with methoxylamine hydrochloride as described in the preparation of compound 3-A gave the title oxime ether as a clear oil after chromatography on silica gel (elution hexane-ethyl acetate 8:2) (96% yield). $^1$HNMR indicated a 95:5 mixture of E- and Z-isomers. $^1$HNMR 400 MHz (CDCl$_3$) δ (ppm): (E-isomer) 1.33 (6H, d, J=6.1 Hz, CH$_3$), 3.97 (3H, s, OCH$_3$), 4.56 (1H, m, CH), 6.90 (2H, m, aromatics), 7.30 (1H, m, aromatic), 7.79 (1H, dd, J=2.0 Hz and J=7.6 Hz, aromatic), 8.47 (1H, s, CH).

Compound 31-B: N-(2-Isopropoxy-benzyl)-O-methyl-hydroxylamine

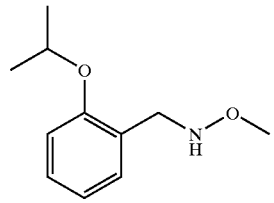

Reduction of 2-isopropoxy-benzaldehyde O-methyloxime with sodium cyanoborohydride as described in the preparation of compound 3-B gave the title hydroxylamine as a clear oil after chromatography on silica gel (elution hexane-ethyl acetate 8:2) (83% yield). $^1$HNMR 400 MHz (CDCl$_3$) δ (ppm): 1.35 (6H, d, J=6.1 Hz, CH$_3$), 3.56 (3H, s, OCH$_3$), 4.07 (2H, broad s, NCH$_2$), 4.59 (1H, m, CH), 6.08 (1H, broad s, NH), 6.86–6.91 (2H, m, aromatics), 7.20–7.24 (2H, m, aromatics). The hydrochloride salt was obtained as a white solid: mp 90° C. Anal. calcd for C$_{11}$H$_{17}$NO$_2$—HCl: C, 57.02; H, 7.83; N, 6.04. Found: C, 56.93; H, 7.64; N, 5.96

Compound 31-C: 2-(2,2-Dimethyl-5-oxo-[1,3]dioxolan-4-ylidene)-N-(2-isopropoxy-benzyl)-N-methoxy-acetamide

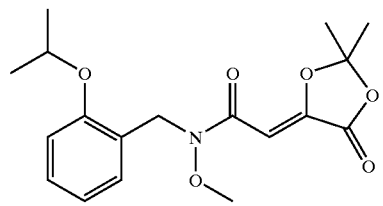

Reaction of (2,2-dimethyl-5-oxo-[1,3]dioxolan-4-ylidene)-acetyl chloride with N-(2-isopropoxy-benzyl)-O-methyl-hydroxylamine as described in the preparation of compound 1-A gave the title amide as white crystals (93% yield): mp 103° C. (ethyl acetate-hexane). $^1$HNMR 400 MHz (CDCl$_3$) δ (ppm): 1.34 (6H, d, J=6.0 Hz, CH$_3$), 1.75 (6H, s, CH$_3$), 3.68 (3H, s, OCH$_3$), 4.60 (1H, m, CH), 4.95 (2H, broad s, NCH$_2$), 6.44 (1H, s, CH), 6.89 (2H, m, aromatics), 7.2–7.3 (2H, m, aromatics). Anal. calcd for C$_{18}$H$_{23}$NO$_6$: C, 61.88; H, 6.64; N, 4.01. Found: C, 61.22; H, 6.33; N, 3.87.

Compound 31: 2-Hydroxy-3-[(2-isopropoxy-benzyl)-methoxy-carbamoyl]-acrylic acid

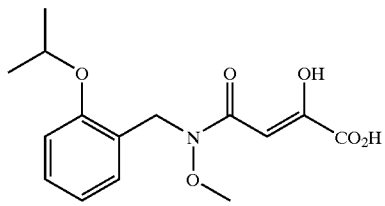

Saponification of 2-(2,2-dimethyl-5-oxo-[1,3]dioxolan-4-ylidene)-N-(2-isopropoxy-benzyl)-N-methoxy-acetamide as described in the preparation of compound 1 gave the title material as a white syrup (92% yield). $^1$HNMR 400 MHz (CDCl$_3$) δ (ppm): 1.33 (6H, d, J=6.1 Hz, CH$_3$) 3.69 (3H, s, OCH$_3$), 4.60 (1H, m, CH), 4.91 (2H, s, NCH$_2$), 6.60 (1H, s, CH), 6.87–6.92 (2H, m, aromatics), 7.21–7.28 (2H, m, aromatics). HRMS (MAB N$_2$) calculated for C$_{15}$H$_{19}$NO$_6$ [M$^+$]: 309.121238: found: 309.120947.

EXAMPLE 32

Compound 32-A: 4-Formyl-benzoic acid tert-butyl ester

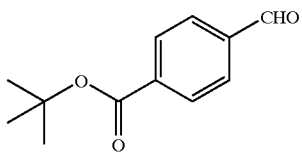

A suspension of 4-carboxybenzaldehyde (5.2 g, 34.6 mmol) in tetrahydrofuran (130 ml) was treated under argon with di-tert-butyl dicarbonate (15.3 g, 70.0 mmol) and 4-dimethylaminopyridine (1.28 g, 10.0 mmol) and the resulting mixture was stirred at 22° C. for 72 h. After dilution with dichloromethane, the reaction mixture was washed successively with 5% citric acid, saturated sodium bicarbonate and brine and dried over anhydrous magnesium sulphate. Evaporation of the solvent under reduced pressure and chromatography of the residue on silica gel (elution toluene-ethyl acetate, 95:5) yielded 2.43 g (34% yield) of the title ester as a white solid. $^1$HNMR 400 MHz (CDCl$_3$) δ (ppm): 1.61 (9H, s, t-Bu), 7.92 (2H, d, J=8.3 Hz, aromatics), 8.13 (2H, d, J=8.3 Hz, aromatics), 10.09 (1H, s, CH).

Compound 32-B: 4-(Methoxyimino-methyl)-benzoic acid tert-butyl ester

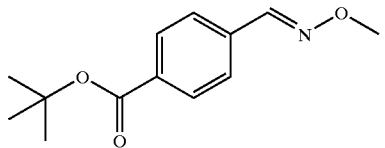

Reaction of 4-formyl-benzoic acid tert-butyl ester with methoxylamine hydrochloride as described in the preparation of compound 3-A gave the title oxime ether as a clear oil after chromatography on silica gel ( elution hexane-ethyl acetate, 96:4) (79% yield). $^1$HNMR 400 MHz (CDCl$_3$) δ (ppm): 1.60 (9H, s, t-Bu), 4.00 (3H, s, OCH$_3$), 7.62 (2H, d, J=8.0 Hz, aromatics), 7.97 (2H, d, J=8.0 Hz, aromatics), 8.08 (1H, s, CH).

Compound 32-C: 4-(Methoxyamino-methyl)-benzoic acid tert-butyl ester

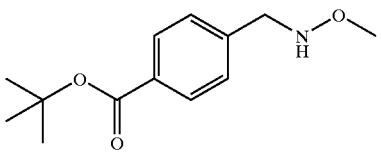

Reduction of 4-(methoxyimino-methyl)-benzoic acid tert-butyl ester with sodium cyanoborohydride as described in the preparation of compound 3-B gave the title hydroxylamine as a clear oil after chromatography on silica gel (elution hexane-ethyl acetate 8:2) (56% yield). $^1$HNMR 400 MHz (CDCl$_3$) δ (ppm): 1.59 (9H, s, t-Bu), 3.49 (3H, s, OCH$_3$), 4.09 (2H, s, NCH$_2$), 7.41 (2H, d, J=8.6 Hz, aromatics), 7.96 (2H, d, J=8.6 Hz, aromatics). The hydrochloride salt was obtained as a white solid: mp 130–132° C. Anal. calcd for C$_{13}$H$_{19}$NO$_3$—HCl: C, 57.04; H, 7.36; N, 5.12. Found: C, 56.90; H, 7.27; N, 5.00.

Compound 32-D: 4-({[2-(2,2-Dimethyl-5-oxo-[1,3] dioxolan-4-ylidene)-acetyl]-methoxy-amino}-methyl)-benzoic acid tert-butyl ester

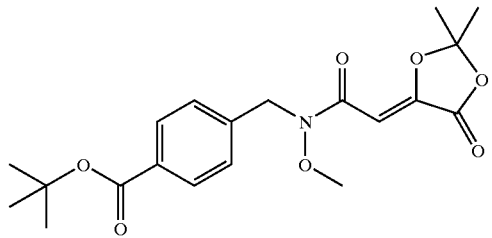

Reaction of (2,2-dimethyl-5-oxo-[1,3]dioxolan-4-ylidene)-acetyl chloride with 4-(methoxyamino-methyl)-benzoic acid tert-butyl ester as described in the preparation of compound 1-A gave the title amide as white crystals (93% yield): mp 137–138° C. (dichloromethane-hexane). $^1$HNMR 400 MHz (CDCl$_3$) δ (ppm): 1.58 (9H, s, t-Bu), 1.76 (6H, s, CH$_3$), 3.67 (3H, s, OCH$_3$), 4.87 (2H, s, NCH$_2$), 6.40 (1H, s, CH), 7.39 (2H, d, J=8.2 Hz, aromatics), 7.95 (2H, d, J=8.2 Hz, aromatics). Anal. calcd for C$_{20}$H$_{25}$NO$_7$: C, 61.37; H. 6.44; N, 3.58. Found: C, 61.23; H, 6.25; N, 3.52.

Compound 32-E: 4-({[2-(2,2-Dimethyl-5-oxo-[1,3] dioxolan-4-ylidene)-acetyl]-methoxy-amino}-methyl)-benzoic acid

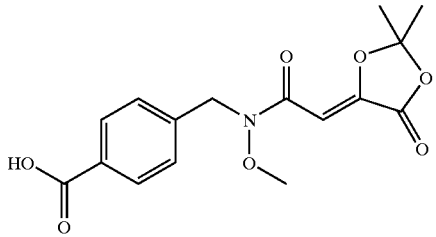

A solution of 4-({[2-(2,2-dimethyl-5-oxo-[1,3]dioxolan-4-ylidene)-acetyl]-methoxy-amino}-methyl)-benzoic acid tert-butyl ester (0.60 g, 1.53 mmol) in dichloromethane (25 ml) was treated at 22° C. with trifluoroacetic acid (6 ml) and the resulting mixture was stirred for 1 h. Evaporation of the solvent in vacuo and recrystallization of the solid residue gave 0.457 g (89% yield) of the title material as white crystals: mp 217–219° C. (dichloromethane-hexane). ¹HNMR 400 MHz (DMSO-$d_6$) δ (ppm): 1.70 (6H, s, $CH_3$), 3.72 (2H, s, $OCH_3$), 4.89 (2H, s, $NCH_2$), 6.18 (1H, s, CH), 7.39 (2H, d, J=8.3 Hz, aromatics), 7.91 (2H, d, J=8.3 Hz, aromatics), 12.9 (1H, broad s, OH). Anal. calcd for $C_{16}H_{17}NO_7$: C, 57.31; H, 5.11; N, 4.18. Found: C, 57.33; H, 5.08; N, 4.25.

Compound 32: 4-{[(3-Carboxy-3-hydroxy-acryloyl)-methoxy-amino]-methyl}-benzoic acid methyl ester

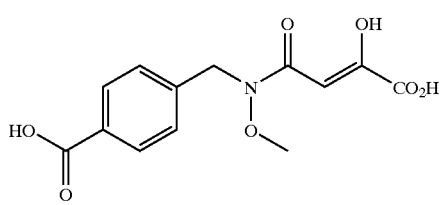

Saponification of 4-({[2-(2,2-dimethyl-5-oxo-[1,3]dioxolan-4-ylidene)-acetyl]-methoxy-amino}-methyl)-benzoic acid as described in the preparation of compound 1 gave the title material as a white solid (66% yield); mp 123–125° C. ¹HNMR 400 MHz (DMSO-$d_6$) δ (ppm) :mixture of enol and keto forms, 7:3; enol form, 3.75 (3H, s, $OCH_3$), 4.97 (2H, s, $NCH_2$), 6.34 (1H, s, CH), 7.4 (2H, d, J=8.3 Hz, aromatics), 7.92 (2H, d, J=8.3 Hz, aromatics), 13.2 (2H, broad, OH); keto form, 3.65 (3H, s, $OCH_3$), 3.97 (2H, s, $CH_2$), 4.87 (2H, s, $NCH_2$). Anal. calcd for $C_{13}H_{13}NO7$ —0.2 $H_2O$: C, 52.25; H, 4.52; N, 4.69. Found: C, 52.17; H, 4.42; N, 4.64.

EXAMPLE 33

Compound 33: 4-({[2-(2,2-Dimethyl-5-oxo-[1,3]dioxolan-4-ylidene)-acetyl]-methoxy-amino}-methyl)-N-methyl-benzamide

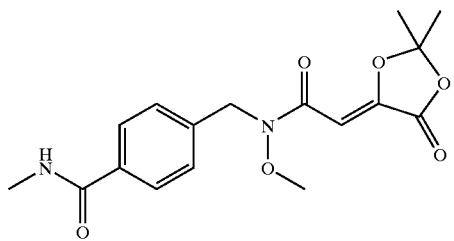

A solution of 4-({[2-(2,2-dimethyl-5-oxo-[1,3]dioxolan-4-ylidene)-acetyl]-methoxy-amino}-methyl)-benzoic acid (0.150 g, 0.45 mmol) in dichloromethane (2 ml) was treated at 22° C. with oxalyl chloride (0.08 ml) and a trace (capillary) of N,N-dimethylformamide and the resulting mixture was stirred for 2 h. The solvent and excess reagent were evaporated in vacuo and the residue was dissolved in dichloromethane (2 ml). This solution was added dropwise to a cold (5° C.) solution of methylamine (0.5 mmol, 0.25 ml of a 2M solution in tetrahydrofuran) and pyridine (0.01 ml) in dichloromethane (2 ml). After 1 h at 22° C., the reaction mixture was diluted with ethyl acetate, washed successively with 0.1 N hydrochloric acid, saturated sodium bicarbonate, brine and dried over anhydrous magnesium sulphate. Evaporation of the solvent under reduced pressure and chromatography of the residue on silica gel (elution ethyl acetate and acetonitrile, 0 to 5%) yielded 0.060 g (38% yield) of the title amide as a white solid. ¹HNMR 400 MHz (DMSO-$d_6$) δ (ppm): 1.69 (6H, s, $CH_3$), 2.77 (3H, d, J=4.5 Hz, $NCH_3$), 3.72 (2H, s, $OCH_3$), 4.85 (2H, s, $NCH_2$), 6.18 (1H, s, CH), 7.35 (2H, d, J=8.2 Hz, aromatics), 7.79 (2H, d, J=8.2 Hz, aromatics), 8.41 (1H, broad q, NH).

EXAMPLE 34

Compound 34-A: 3-(4-Fluorophenyl)-propionaldehyde O-methyloxime

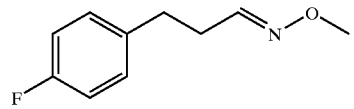

Reaction of 3-(4-fluorophenyl)-propionaldehyde (Dickinson, R. P.; Dack, K. N.; Steele, J.; Tute, M. S. Bioorg. Med. Chem. Lett., 6, 14, 1996, 1691–1696) with methoxylamine hydrochloride as described in the preparation of compound 3-A gave the title oxime ether as a clear oil (97% yield), bp 65–75° C./1.5 torr (bulb to bulb distillation, air bath temperature). ¹HNMR indicated a 6:4 mixture of E- and Z-isomers. ¹HNMR 400 MHz (CDCl₃) δ (ppm): 2.51 and 2.65 (2H, 2 m, $CH_2$), 2.8 (2H, m, $CH_2$), 3.84 and 3.88 (3H, 2 s, $OCH_3$), 6.67 (t, J=5.5 Hz, CH), 7.0 (2H, m, aromatics), 7.16 (2H, m, aromatics), 7.40 (t, J=4.2 Hz, CH).

Compound 34-B: N-[3-(4-Fluorophenyl)-propyl]-O-methyl-hydroxylamine

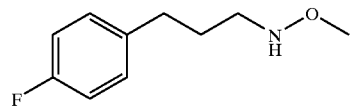

Reduction of 3-(4-fluorophenyl)-propionaldehyde O-methyloxime with sodium cyanoborohydride as described in the preparation of compound 3-B gave the title hydroxylamine as a clear oil after chromatography on silica gel and distillation in vacuo (75% yield): bp 70–75° C./0.7 torr (bulb to bulb distillation, air bath temperature). ¹HNMR 400 MHz (CHCl₃) δ (ppm): 1.85 (2H, m, $CH_2$), 2.68 (2H, t, J=7.9 Hz, $CH_2$), 2.95 (2H, t, J=7.1 Hz, $CH_2$), 3.56 (3H, s, $OCH_3$), 5.58 (1H, broad, NH), 6.99 (2H, m, aromatics), 7.17 (2H, m, aromatics). The hydrochloride salt was obtained as a white solid: mp 97–100° C. Anal. calcd for $C_{10}H_{14}FNO$—HCl: C, 54.67; H, 6.88; N, 6.38. Found: C, 54.72; H, 6.71; N, 6.42.

Compound 34-C: 2-(2,2-Dimethyl-5-oxo-[1,3]
dioxolan-4-ylidene)-N-[3-(4-fluoro-phenyl)-propyl]-
N-methoxy-acetamide

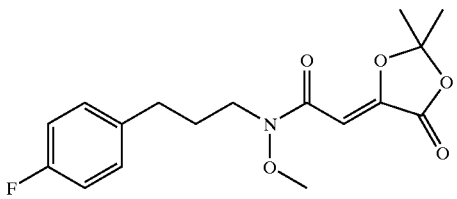

Reaction of (2,2-dimethyl-5-oxo-[1,3]dioxolan-4-ylidene)-acetyl chloride with N-[3-(4-fluorophenyl)-propyl]-O-methyl-hydroxylamine as described in the preparation of compound 1-A gave the title amide as white crystals (97% yield): mp 90–91° C. (ethyl acetate-hexane). $^1$HNMR 400 MHz (CDCl$_3$) δ (ppm): 1.77 (6H, s, CH$_3$), 1.98 (2H, m, CH$_2$), 2.64 (2H, t, J=7.9 Hz, CH$_2$), 3.71 (2H, t, J=7.6 Hz, NCH$_2$), 3.73 (3H, s, OCH$_3$), 6.41 (1H, broad s, CH), 6.98 (2H, m, aromatics), 7.16 (2H, m, aromatics). Anal. calcd for C$_{17}$H$_{20}$FNO$_5$: C, 60.53; H, 5.98; N, 4.15. Found: C, 60.43; H, 5.99; N, 4.09.

Compound 34: 3-{[3-(4-Fluorophenyl)-propyl]-
methoxy-carbamoyl}-2-hydroxy-acrylic acid

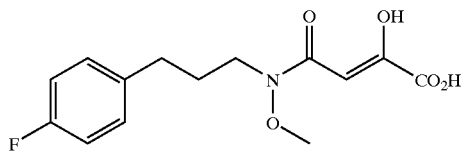

Saponification of 2-(2,2-dimethyl-5-oxo-[1,3]dioxolan-4-ylidene)-N-[3-(4-fluoro-phenyl)-propyl]-N-methoxy-acetamide as described in the preparation of compound 1 gave the title material as white crystals (98% yield): mp 86° C. (dec) (ether-hexane). $^1$HNMR 400 MHz (CDCl$_3$) δ (ppm): 2.0 (2H, m, CH$_2$), 2.65 (2H, t, J=7.8 Hz, CH$_2$), 3.72 (2H, t, J=7.1 Hz, NCH$_2$), 3.75 (3H, s, OCH$_3$), 6.57 (1H, s, CH), 7.0 (2H, m, aromatics), 7.17 (2H, m, aromatics). Anal. calcd for C$_{14}$H$_{16}$FNO$_5$: C, 56.56; H. 5.43; N, 4.71. Found: C, 56.78; H, 5.49; N, 4.69.

EXAMPLE 35

Compound 35-A: 3-(3,4-Dichlorophenyl)-
propionaldehyde O-methyloxime

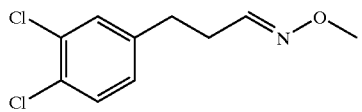

Reaction of 3-(3,4-dichlorophenyl)-propionaldehyde (Heck, J. Amer. Chem. Soc., 90, 1968, 5526) with methoxylamine hydrochloride as described in the preparation of compound 3-A gave the title oxime ether as a clear oil (91% yield), bp 80–90° C./0.5 torr (bulb to bulb distillation, air bath temperature). $^1$HNMR indicated a 55:45 mixture of E- and Z-isomers. $^1$HNMR 400 MHz (CDCl$_3$) δ (ppm): 2.63 and 2.76 (2H, 2 m, CH$_2$), 2.9 (2H, m, CH$_2$), 3.96 and 4.01 (3H, 2 s, OCH$_3$), 6.77 (t, J=5.5 Hz, CH), 7.16–7.5 (3H, m, aromatics and CH).

Compound 35-B: N-[3-(3,4-Dichlorophenyl)-
propyl]-O-methyl-hydroxylamine

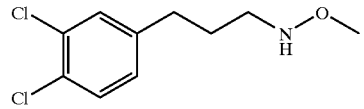

Reduction of 3-(3,4-dichlorophenyl)-propionaldehyde O-methyloxime with sodium cyanoborohydride as described in the preparation of compound 3-B gave the title hydroxylamine as a clear oil after chromatography on silica gel and distillation in vacuo (48% yield): bp 75–80° C./0.3 torr (bulb to bulb distillation, air bath temperature). $^1$HNMR 400 MHz (CHCl$_3$) δ (ppm): 1.81 (2H, m, CH$_2$), 2.63 (2H, t, J=7.8 Hz, CH$_2$), 2.90 (2H, t, J=7.1 Hz, CH$_2$), 3.52 (3H, s, OCH$_3$), 5.55 (broad, NH), 7.01 (1H, dd, J=2.0 Hz and J=8.1 Hz, aromatic), 7.27 (1H, broad d, aromatic), 7.32 (1H, d, J=8.1 Hz, aromatic). The hydrochloride salt was obtained as a white solid: mp 81–83° C. Anal. calcd for C$_{10}$H$_{13}$Cl$_2$NO—HCl: C, 44.39; H, 5.22; N, 5.18. Found: C, 44.57; H, 5.05; N, 5.18.

Compound 35-C: N-[3-(3,4-Dichloro-phenyl)-
propyl]-2-(2,2-dimethyl-5-oxo-[1,3]dioxolan-4-
ylidene)-N-methoxy-acetamide

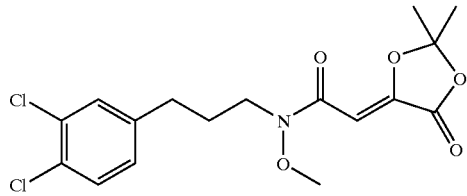

Reaction of (2,2-dimethyl-5-oxo-[1,3]dioxolan-4-ylidene)-acetyl chloride with N-[3-(3,4-dichlorophenyl)-propyl]-O-methyl-hydroxylamine as described in the preparation of compound 1-A gave the title amide as white crystals (95% yield): mp 105–106° C. (ethyl acetate-hexane). $^1$HNMR 400 MHz (CDCl$_3$) δ (ppm): 1.91 (6H, s, CH$_3$), 2.13 (2H, m, CH$_2$), 2.77 (2H, t, J=7.9 Hz, CH$_2$), 3.86 (2H, t, J=7.0 Hz, NCH$_2$), 3.88 (3H, s, OCH$_3$), 6.54 (1H, broad s, CH), 7.2 (H, broad dd, aromatic), 7.44 (1H, broad d, J=2 Hz, aromatic), 7.50 (1H, d, J=8.1 Hz, aromatic). Anal. calcd for C$_{17}$H$_{19}$Cl$_2$NO$_5$: C, 52.59; H, 4.93; N, 3.61. Found: C, 52.68; H, 5.08; N, 3.50.

Compound 35: 3-{[3-(3,4-Dichlorophenyl)-propyl]-
methoxy-carbamoyl}-2-hydroxy-acrylic acid

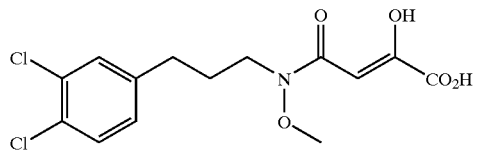

Saponification of N-[3-(3,4-dichloro-phenyl)-propyl]-2-(2,2-dimethyl-5-oxo-[1,3]dioxolan-4-ylidene)-N-methoxy-acetamide as described in the preparation of compound 1 gave the title material as white crystals (97% yield): mp 106° C. (dec) (ethyl acetate-hexane). $^1$HNMR 400 MHz (CDCl$_3$) δ (ppm): 1.97 (2H, m, CH$_2$), 2.61 (2H, t, J=7.7 Hz, CH$_2$), 3.71 (2H, t, J=6.9 Hz, NCH$_2$), 3.73 (3H, s, OCH$_3$), 6.54 (1H, s, CH), 7.03 (1H, dd, J=2.0 Hz and J=8.24 Hz, aromatic), 7.28 (1H, d, J=2.0 Hz, aromatic) 7.35 (1H, d, J=8.24 Hz, aromatic). Anal. calcd for C$_{14}$H$_{15}$Cl$_2$NO$_5$: C, 48.29; H, 4.34; N, 4.02. Found: C, 48.34; H, 4.24; N, 3.98.

EXAMPLE 36

Compound 36-A: (3,4-Dichlorobenzylideneaminooxy)-acetic acid tert-butyl ester

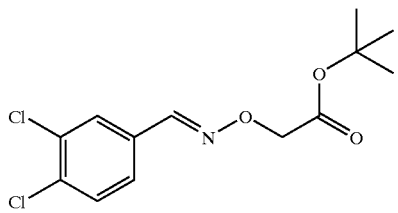

Condensation of 3,4-dichlorobenzaldehyde with hydroxylamine hydrochloride followed by reaction with tert-butyl bromoacetate using a procedure similar to the one described for the preparation of compound 6-A gave the title oxime ether as a clear oil after chromatography on silica gel (elution dichloromethane-hexane 1:1) (94% yield). $^1$HNMR 400 MHz (CDCl$_3$) δ (ppm): 1.52 (9H, s, t-Bu), 4.63 (2H, s, OCH$_2$), 7.41 (1H, dd, J=1.9 Hz and J=8.6 Hz, aromatic), 7.47 (1H, d, J=8.6 Hz, aromatic), 7.71 (1H, d, J=1.9 Hz, aromatic), 8.13 (1H, s, CH).

Compound 36-B: [N-(3,4-Dichlorobenzyl)aminooxy]-acetic acid tert-butyl ester

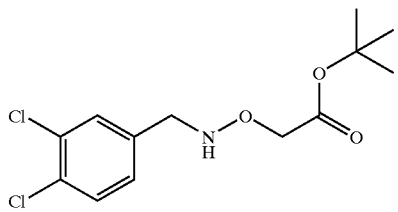

Reduction of (3,4-dichlorobenzylideneaminooxy)-acetic acid tert-butyl ester as described in the preparation of compound 3-B gave the title hydroxylamine as a clear oil (50% yield). $^1$HNMR 400 MHz (C$_6$D$_6$) δ (ppm): 1.4 (9H, s, t-Bu), 3.6 (2H, broad s, NCH$_2$), 4.1 (2H, s, OCH$_2$), 6.35 (1H, broad, NH), 6.75 (1H, dd, J=2.0 Hz and J=8.1 Hz, aromatic), 7.07 (1H, d, J=8.1 Hz, aromatic), 7.24 (H, d, J=2.0 Hz, aromatic).

Compound 36: {(3,4-Dichlorobenzyl)-[2-(2,2-dimethyl-5-oxo-[1,3]-dioxolan-4-ylidene)-acetyl]-aminooxy}-acetic acid tert-butyl ester

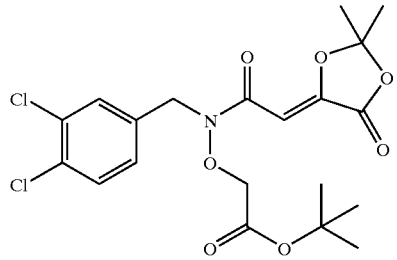

Reaction of (2,2-dimethyl-5-oxo-[1,3]dioxolan-4-ylidene)-acetyl chloride with [N-(3,4-dichlorobenzyl) aminooxy]-acetic acid tert-butyl ester as described in the preparation of compound 1-A gave the title amide as white crystals (49% yield): mp 127–129° C. (ethyl acetate-hexane). $^1$HNMR 400 MHz (CDCl$_3$) δ (ppm): 1.51 (9H, s, t-Bu), 1.78 (6H, s, CH$_3$), 4.38 (2H, s, CH$_2$), 4.90 (2H, s, CH$_2$), 6.49 (1H, s, CH), 7.28 (1H, dd, J=2.5 Hz and J=8.0 Hz, aromatic), 7.41 (1H, d, J=8.0 Hz, aromatic), 7.53 (1H, d, J=2.5 Hz, aromatic). Anal. calcd for C$_{20}$H$_{23}$Cl$_2$NO$_7$: C, 52.19; H, 5.04; N, 3.04. Found: C, 52.25; H, 5.11; N, 2.93.

EXAMPLE 37

Compound 37-A: 4-Fluorobenzaldehyde O-(2-chloroethyl)-oxime

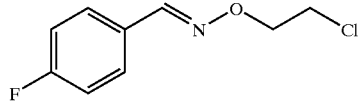

A suspension of sodium hydride (10.0 mmol, 0.40 g of a 60% suspension in mineral oil) in dry tetrahydrofuran (20 ml) was treated at 25° C. with 1-bromo-2-chloroethane (2 ml, 23.8 mmol) followed by a solution of 4-fluorobenzaldehyde oxime (1.39 g, 10.0 mmol) in tetrahydrofuran (20 ml) added dropwise over 10 min. The resulting mixture was then heated under reflux for 16 h. The cooled mixture was diluted with ethyl acetate, washed with brine and dried over anhydrous sodium sulphate. Evaporation of the solvent under reduced pressure and chromatography of the residue on silica gel (elution hexane-ethyl acetate, 8:2) gave 0.80 g (40% yield) of the title oxime as a clear oil. $^1$HNMR 400 MHz (CDCl$_3$) δ (ppm): 3.81 (2H, t, J=6.0 Hz, CH$_2$), 4.4 (2H, t, J=6.0 Hz, CH$_2$), 7.10 (2H, m, aromatics), 7.60 (2H, m, aromatics), 8.13 (1H, s, CH).

Compound 37-B: O-(2-Chloroethyl)-N-(4-fluorobenzyl)-hydroxylamine

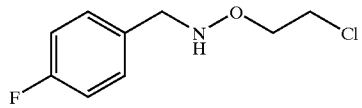

Reduction of 4-fluorobenzaldehyde O-(2-chloroethyl)-oxime as described in the preparation of compound 3-B gave the title hydroxylamine as a clear oil (65% yield) after chromatography on silica gel (elution hexane-ethyl acetate, 7:3). $^1$HNMR 400 MHz (C$_6$D$_6$) δ (ppm): 3.31 (2H, t, J=6.0 Hz, CH$_2$), 3.61 (2H, t, J=6.0 Hz, CH$_2$), 3.65 (2H, s, NCH$_2$), 5.14 (1H, broad s, NH), 6.87 (2H, m, aromatics), 6.98 (2H, m, aromatics). The hydrochloride salt was obtained as a white solid. Anal. calcd for C$_9$H$_{11}$ClFNO—HCl: C, 53.08; H, 5.44; N, 6.88. Found: C, 53.17; H, 5.31; N, 7.07.

Compound 37-C: O-(2-Dimethylamino-ethyl)-N-(4-fluorobenzyl)-hydroxylamine

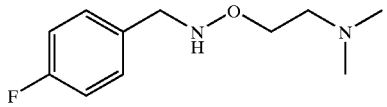

A solution of O-(2-chloroethyl)-N-(4-fluorobenzyl)-hydroxylamine (0.327 g, 1.6 mmol) in acetonitrile (2 ml) was treated with a solution of dimethylamine (16 mmol, 8 ml of a 2 M solution in tetrahydrofuran). Sodium iodide (0.06 g) was then added and the resulting mixture was sealed and heated at 55° C. for 16 h. The cooled mixture was diluted with ethyl acetate, washed with saturated sodium bicarbonate, brine and dried over anhydrous sodium sulphate. Evaporation of the solvent under reduced pressure yielded 0.310 g (91% yield) of the crude title hydroxylamine as a light brown oil which was used as such for the next step. $^1$HNMR 400 MHz (C$_6$D$_6$) δ (ppm): 2.19 (6H, s, NCH$_3$), 2.47 (2H, t, J=6.1 Hz, CH$_2$), 3.82 (2H, s, NCH$_2$), 3.84 (2H, t, J=6.1 Hz, CH$_2$), 6.9 (2H, m, aromatics), 7.11 (2H, m, aromatics).

Compound 37-D: N-(2-Dimethylamino-ethoxy)-2-(2,2-dimethyl-5-oxo-[1,3]dioxolan-4-ylidene)-N-(4-fluoro-benzyl)-acetamide

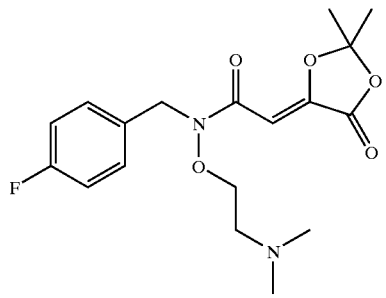

Reaction of (2,2-dimethyl-5-oxo-[1,3]dioxolan-4-ylidene)-acetyl chloride with O-(2-dimethylamino-ethyl)-N-(4-fluorobenzyl)-hydroxylamine as described in the preparation of compound 1-A gave the title amide as white crystals (30% yield): mp 95–96° C. (ether-hexane). $^1$HNMR 400 MHz (DMSO-d$_6$) δ (ppm): 1.70 (6H, s, CH$_3$), 2.16 (6H, s, NCH$_3$), 2.44 (2H, t, J=5.3 Hz, CH$_2$), 3.97 (2H, t, J=5.3 Hz, CH$_2$), 4.79 (2H, s, NCH$_2$), 6.52 (1H, s, CH), 7.18 (2H, m, aromatics), 7.34 (2H, m, aromatics). Anal. calcd for C$_{18}$H$_{23}$FN$_2$O$_5$: C, 59.00; H, 6.32; N, 7.64. Found: C, 58.73; H, 6.13; N, 7.40.

Compound 37: 3-[(2-Dimethylamino-ethoxy)-(4-fluorobenzyl)-carbamoyl]-2-hydroxy-acrylic acid

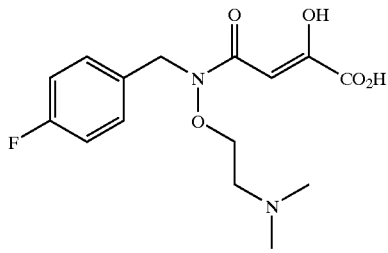

Saponification of N-(2-dimethylamino-ethoxy-2-(2,2-dimethyl-5-oxo-[1,3]-dioxolan-4-ylidene)-N-(4-fluorobenzyl)-acetamide as described in the preparation of compound 1 gave the title material as a white powder after adjusting to pH 5 (1 N HCl), chromatography on reversed phase silica gel (Waters, C-18, 125 A) and freeze drying (68% yield). $^1$HNMR 400 MHz (DMSO-d$_6$) δ (ppm): mainly keto form 2.73 (6H, s, NCH$_3$), 3.22 (2H, broad s, CH$_2$), 3.72 (2H, broad s, CH$_2$), 4.18 (2H, broad s, OCH$_2$), 4.81 (2H, s, NCH$_2$), 7.17 (2H, m, aromatics), 7.38 (2H, m, aromatics). HRMS (MAB N$_2$) calculated for C$_{15}$H$_{19}$FN$_2$O$_5$ [M$^+$]: 326.127800: found: 326.127864. Anal. calcd for C$_{15}$H$_{19}$FN$_2$O$_5$—H$_2$O: C, 52.32; H, 6.15; N, 8.14. Found: C, 52.80; H, 5.79; N, 8.02.

EXAMPLE 38

Compound 38-A: [[2-(2,2-dimethyl-5-oxo-[1,3]dioxolan-4-ylidene)-acetyl]-(4-fluoro-benzyl)-aminooxy]-acetyl chloride

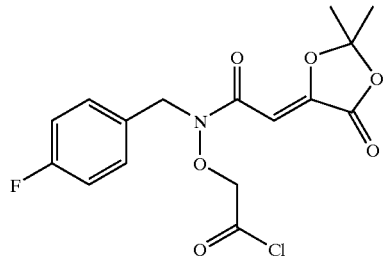

Compound 38-A was prepared from compound 22-A using the procedure described in the preparation of compound 22-B.

Method for the Preparation of Compounds 38–61

Amine (0.165 mmol), VI-A in Scheme VI, was combined with 2-(2-pyridyl)ethyl functionalized silica gel (0.38 mmol equivalents) in 1 mL of 1,2-dichloroethane at 5° C. To this was added [[2-(2,2-dimethyl-5-oxo-[1,3]dioxolan-4-ylidene)-acetyl]-(4-fluoro-benzyl)-aminooxy]-acetyl chloride (0.165 mmol) dissolved in 1 mL of 1,2-dichloroethane. After 1 hour at 25° C. the reaction mixture was filtered and purified on a Shimadzu automated preparative HPLC system (Waters XTerra™ C-8, 5μ, 19×100 mm, solvent A: Water 5 mM NH$_4$OAC; Solvent B: Acetonitrile).

The collected compounds were analysed using the following LC/MS conditions.

| | |
|---|---|
| Column: | X Terra 5μ C-8, 4.6 × 30 mm |
| Solvent: | Solvent A: 10% CH₃CN-90% H₂O, 5 mM NH₄Oac |
| | Solvent B: 90% CH₃CN-10% H₂O, 5 mM NH₄Oac |
| Gradient: | 100% solvent A/0% solvent B to 0% solvent A/100% solvent B |
| Gradient time: | 2 minutes, hold time 1 minute. |
| Flow rate: | 4 ml/min. |

-continued

Detector wavelength 220 nm.

Compound retention times (RT) are recorded in the table below. Spectrometry (MS) data were determined with a Micromass ZMD Platform TSQ 7000 LC/MS in positive electrospray mode. Results are reported in the table below.

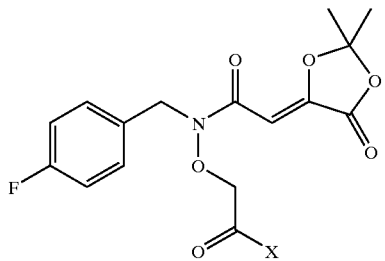

| Compound | X | RT | Formula | MS |
|---|---|---|---|---|
| 38 | morpholine | 1.34 | $C_{20}H_{23}FN_2O_7$ | 423 |
| 39 | N(CH₃)-propyl-iminodibenzyl | 1.95 | $C_{34}H_{36}FN_3O_6$ | 602 |
| 40 | 4-(pyrimidin-2-yl)piperazin-1-yl | 1.53 | $C_{24}H_{26}FN_5O_6$ | 500 |
| 41 | NH-CH(CH₃)-phenyl | 1.69 | $C_{24}H_{25}FN_2O_6$ | 457 |
| 42 | NH-CH₂-(4-fluorophenyl) | 1.68 | $C_{23}H_{22}F_2N_2O_6$ | 461 |

-continued
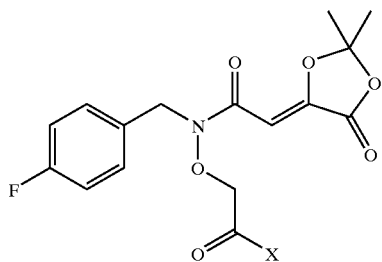
| Compound | X | RT | Formula | MS |
|---|---|---|---|---|
| 43 | 4-Cl-C6H4-CH2-NH- | 1.75 | $C_{23}H_{22}ClFN_2O_6$ | 477 |
| 44 | 4-CH3O-C6H4-CH2-NH- | 1.64 | $C_{24}H_{25}FN_2O_7$ | 473 |
| 45 | 4-CH3-C6H4-CH2-NH- | 1.71 | $C_{24}H_{25}FN_2O_6$ | 457 |
| 46 | 4-F3C-C6H4-CH2-NH- | 1.79 | $C_{24}H_{22}F_4N_2O_6$ | 511 |
| 47 | 4-F-C6H4-CH(CH3)-NH- | 1.72 | $C_{24}H_{24}F_2N_2O_6$ | 475 |
| 48 | (4-Cl-C6H4)2CH-CH2CH2CH2-N(CH3)- | 2.08 | $C_{33}H_{33}Cl_2FN_2O_6$ | 643 |

-continued
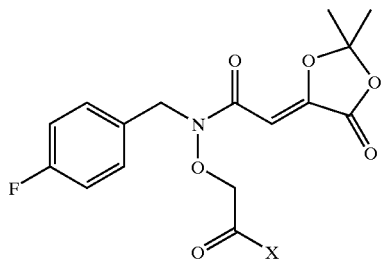
| Compound | X | RT | Formula | MS |
|---|---|---|---|---|
| 49 | N-benzyl-N-butyl | 1.87 | $C_{27}H_{31}FN_2O_6$ | 499 |
| 50 | N-(cyclopropylmethyl)-N-propyl | 1.72 | $C_{23}H_{29}FN_2O_6$ | 449 |
| 51 | 2,6-dimethylmorpholino | 1.53 | $C_{22}H_{27}FN_2O_7$ | 451 |
| 52 | N-methyl-N-(2,2-dimethoxyethyl) | 1.48 | $C_{21}H_{27}FN_2O_8$ | 455 |
| 53 | N,N-diisobutyl | 1.81 | $C_{24}H_{33}FN_2O_6$ | 465 |
| 54 | N,N-dihexyl | 2.08 | $C_{28}H_{41}FN_2O_6$ | 521 |
| 55 | N,N-dicyclohexyl | 1.98 | $C_{28}H_{37}FN_2O_6$ | 517 |

-continued

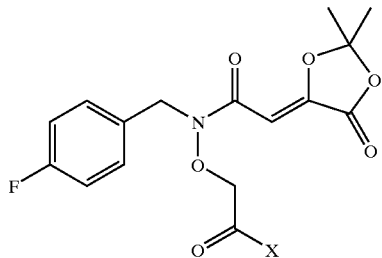

| Compound | X | RT | Formula | MS |
|---|---|---|---|---|
| 56 | ethyl (N-methyl)glycinate group | 1.53 | $C_{21}H_{25}FN_2O_8$ | 453 |
| 57 | (pyridin-4-ylmethyl)(ethyl)amino | 1.47 | $C_{24}H_{26}FN_3O_6$ | 472 |
| 58 | bis(2-methoxyethyl)amino | 1.49 | $C_{22}H_{29}FN_2O_8$ | 469 |
| 59 | 4-acetyl-1,4-diazepan-1-yl | 1.31 | $C_{23}H_{28}FN_3O_7$ | 478 |
| 60 | ethylamino | 1.43 | $C_{18}H_{21}FN_2O_6$ | 381 |
| 61 | isobutylamino | 1.59 | $C_{20}H_{25}FN_2O_6$ | 409 |

EXAMPLE 39

Method for the Preparation of Compounds 62–79

Compounds 38–61 (0.05 mmol) were each dissolved in 2 mL of 1:1 THF/H$_2$O and treated with 0.15 mL of 1M LiOH (in water) at 5° C. for 1.5 hours. The reactions were quenched with 0.25 mL of 1M HCl. After evaporation of solvent the compounds were individually purified by filtration through a Varian Bond Elute C-18 cartridge (Varian Inc. Palo Alto Calif.) using H$_2$O followed by 1:1-H$_2$O/acetonitrile to elute to product. Spectrometry (MS) data were determined with a Micromass ZMD Platform TSQ 7000 LC/MS in negative electrospray mode.

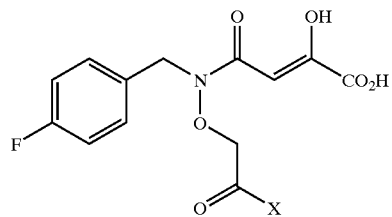
| Compound | X | Formula | MS |
|---|---|---|---|
| 62 | morpholin-4-yl | C$_{17}$H$_{19}$FN$_2$O$_7$ | 381 |
| 63 | N-methyl-N-[3-(10,11-dihydro-5H-dibenzo[b,f]azepin-5-yl)propyl]amino | C$_{31}$H$_{32}$FN$_3$O$_6$ | 560 |
| 64 | (1-phenylethyl)amino | C$_{21}$H$_{21}$FN$_2$O$_6$ | 415 |
| 65 | (4-fluorobenzyl)amino | C$_{20}$H$_{18}$F$_2$N$_2$O$_6$ | 419 |
| 66 | (4-chlorobenzyl)amino | C$_{20}$H$_{18}$ClFN$_2$O$_6$ | 435 |
| 67 | (4-methoxybenzyl)amino | C$_{21}$H$_{21}$FN$_2$O$_7$ | 431 |
| 68 | (4-methylbenzyl)amino | C$_{21}$H$_{21}$FN$_2$O$_6$ | 415 |

-continued
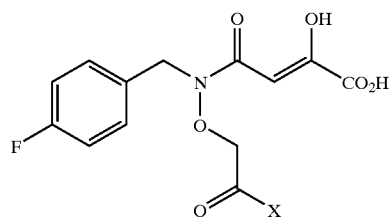
| Compound | X | Formula | MS |
|---|---|---|---|
| 69 | 4-(trifluoromethyl)benzyl-NH- | C₂₁H₁₈F₄N₂O₆ | 469 |
| 70 | 1-(4-fluorophenyl)ethyl-NH- | C₂₁H₂₀F₂N₂O₆ | 433 |
| 71 | N-methyl-N-[4,4-bis(4-chlorophenyl)butyl]-, with additional Cl | C₃₀H₂₉Cl₂FN₂O₆ | 601 |
| 72 | N-benzyl-N-butyl- | C₂₄H₂₇FN₂O₆ | 457 |
| 73 | N-(cyclopropylmethyl)-N-propyl- | C₂₀H₂₅FN₂O₆ | 407 |
| 74 | N,N-diisobutyl- | C₂₁H₂₉FN₂O₆ | 423 |

-continued

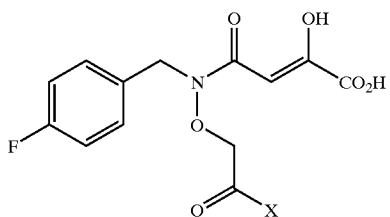

| Compound | X | Formula | MS |
|---|---|---|---|
| 75 | (dihexylamino) | $C_{25}H_{37}FN_2O_6$ | 479 |
| 76 | (dicyclohexylamino) | $C_{25}H_{33}FN_2O_6$ | 475 |
| 77 | (4-acetyl-1,4-diazepan-1-yl) | $C_{20}H_{24}FN_3O_7$ | 436 |
| 78 | (ethylamino) | $C_{15}H_{17}FN_2O_6$ | 339 |
| 79 | (isobutylamino) | $C_{17}H_{21}FN_2O_6$ | 367 |

EXAMPLE 40

HIV-Integrase Inhibition Activity

The table below shows the percent inhibition of HIV-integrase in the presence of 50 $\mu$M compounds 1–24 and 62–79. For each reaction, 5 pmole of biotin labled substrate DNA was bound to 100 ug of Streptavidin coated PVT SPA beads (Amersham Pharmacia Biotech). 0.26 ng of recombinant integrase was incubated with the beads for 90 min at 37° C. Unbound enzyme was removed by washing the complex followed by addition of inhibitors and 0.1 fmol of P33 labeled target DNA. Reaction was stopped by adding EDTA to a final concentration of 10 mM. Samples were counted in TopCountNXT (Packard) and the CPM was used as a measure of integration. Reaction condition was as described in A. Engelman and R. Craigie, J. Virol. 69, 5908–5911 (1995). The sequences of substrate and target DNA were described in Nucleic Acid Research 22, 1121–1122 (1994). Compounds of this invention tested in this assay have $IC_{50}$'s of approximately 0.01 to 50 $\mu$M

| Compound | % inhibition at 50 $\mu$M |
|---|---|
| 1 | 99 |
| 2 | 99.9 |
| 3 | 99.9 |
| 4 | 99.9 |
| 5 | 99.9 |
| 6 | 99.9 |
| 7 | 99.9 |
| 8 | 99.9 |
| 9 | 99.9 |
| 10 | 99.9 |
| 11 | 99.9 |
| 12 | 99.9 |
| 13 | 99.9 |
| 14 | 99.9 |
| 15 | 99.0 |
| 16 | 99.0 |
| 17 | 99.9 |
| 18 | 96.0 |

-continued

| Compound | % inhibition at 50 μM |
|---|---|
| 19 | 99.9 |
| 20 | 99.9 |
| 21 | 99.9 |
| 22 | 99.9 |
| 23 | 65.0 |
| 24 | 99.9 |
| 62 | >99% |
| 63 | >99% |
| 64 | >99% |
| 65 | >99% |
| 66 | >99% |
| 67 | >99% |
| 68 | >99% |
| 69 | >99% |
| 70 | >99% |
| 71 | >99% |
| 72 | >99% |
| 73 | >99% |
| 74 | >99% |
| 75 | >99% |
| 76 | >99% |
| 77 | >99% |
| 78 | >99% |
| 79 | >99% |

Inhibition of HIV Replication

Cell culture assays were preformed using a single cycle, recombinant HIV virus expressing Renella luciferase. Antiviral activity was evaluated by measuring the production of luciferase in the infected cells 5 days post-infection. Susceptibility of the virus to compounds was determined by incubation in the presence of the serially-diluted compound. The 50% effective concentration ($EC_{50}$) was calculated by using the exponential form of the median effect equation where $(Fa)=1/[1+(ED_{50}/\text{drug conc.})^m]$. Compounds of this invention tested in this assay have $EC_{50}$'s of approximately 0.02 to 50 μM. The table below shows the percent viral inhbition at a compound concentration of 1.6 μM for a set representative compounds.

| Compound | % Inhibition @ 1.6 uM |
|---|---|
| 3 | 96 |
| 4 | 90 |
| 5 | 96 |
| 15 | 33 |
| 31 | 47 |
| 3-C | 96 |
| 4-B | 87 |
| 5-B | 94 |

EXAMPLE 41

Hydrolysis of Prodrugs Under Physiological Conditions

As shown in Scheme VII, compounds of Formula VII-A wherein $R^1$ and $R^2$ are as defined for Formula I, are hydrolyzed at pH 7 (37° C.) to yield the corresponding 2-hydroxy acrylic, VII-B, and are thus useful as prodrugs.

Scheme VII

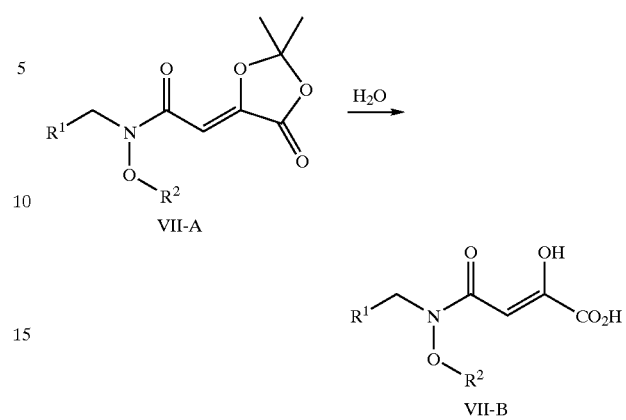

In an experiment to measure the hydrolysis of compounds such as VII-A, compound 3-C was added to 25 mM phosphate buffer (pH 7) at a concentration of 0.03 mg/mL. The reaction was incubated at 37° C. for a period of 24 hours. Interval time points are analyzed by HPLC, identifying both the compound 3-C and compound 3, the parent acid. Results are shown in the table.

| Hydrolysis of compound 3-C at pH 7 (37° C.) | | |
|---|---|---|
| Time (h) | Compound 3-C (mg/mL) | Compound 3 (mg/mL) |
| 0 | 0.026 | 0.001 |
| 0.5 | 0.022 | 0.008 |
| 1 | 0.017 | 0.012 |
| 1.5 | 0.013 | 0.014 |
| 2 | 0.010 | 0.016 |
| 4 | 0.003 | 0.021 |
| 6 | 0.001 | 0.022 |

We claim:
1. A compound of formula I

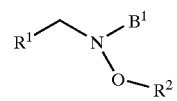

wherein
$R^1$ is
-aryl,
—$C_1$–$C_6$ alkyl-aryl,
—$C_1$–$C_6$ alkyl-S(O)$_n$-aryl, or
—$C_1$–$C_5$ alkyl-O-aryl;
and wherein $R^1$ is unsubstituted or independently substituted with 1–3 $R^3$;
Each $R^3$ is independently selected from
—H,
-halo,
—CN,
—$C_1$–$C_6$ alkyl,
—$C_3$–$C_6$ cycloalkyl,
—$OR^4$,
—$C_1$–$C_{10}$ alkyl-O—$R^4$, —$CO_2R^5$,
—$C_1$–$C_{10}$ alkyl-$CO_2R^5$,
—$N(R^6)(R^7)$,
—$C_1$–$C_{10}$ alkyl-$N(R^6)(R^7)$,
—$CON(R^6)(R^7)$,
—$C_1$–$C_{10}$ alkyl-$CON(R^6)(R^7)$,
—$S(O)_nR^8$,
—$C_1$–$C_{10}$ alkyl-$S(O)_nR^8$,
—$S(O)_nN(R^9)(R^{10})$,
—$C_1$–$C_{10}$ alkyl-$S(O)_nN(R^9)(R^{10})$,
-aryl,
—O-aryl,
-heteroaryl,
—O-heteroaryl,
—$C_1$–$C_6$ alkyl-aryl,
—$C_1$–$C_6$ alkyl-heteroaryl,
—C(O)-heterocyclic radical,
—$C_1$–$C_{10}$ alkyl-C(O)-heterocyclic radical, or
—$C_1$–$C_6$ haloakyl;
$R^2$ is
—H,
—$C_1$–$C_{10}$ alkyl,
—$C_3$–$C_6$ cycloakyl,
—$C_1$–$C_{10}$ haloalkyl,
-aryl,
-heteroaryl,
—$C_1$–$C_6$ alkyl-aryl,
—$C_1$–$C_5$ alkyl-O-aryl,
—$C_1$–$C_6$ alkyl-heteroaryl,
—$C_1$–$C_5$ alkyl-O-heteroaryl,
—$C_1$–$C_6$ alkyl-$OR^4$,
—$C_1$–$C_{10}$ alkyl-$CO_2R^5$,
—$C_1$–$C_{10}$ alkyl-$N(R^6)(R^7)$,
—$C_1$–$C_{10}$ alkyl-$CON(R^6)(R^7)$,
—$C_1$–$C_{10}$ alkyl-$S(O)_nR^8$,
—$C_1$–$C_{10}$ alkyl-$S(O)_nN(R^9)(R^{10})$, or
—$C_1$–$C_{10}$ alkyl-C(O)-heterocyclic radical;
Each $R^4$ is independently selected from
—H,
—$C_1$–$C_6$ alkyl,
—$C_3$–$C_6$ cycloalkyl,
—$C_1$–$C_9$ alkyl-$CO_2R^5$,
—$C_1$–$C_9$ alkyl-$N(R^6)(R^7)$,
—$C_1$–$C_9$ alkyl-$CON(R^6)(R^7)$,
—$C_1$–$C_9$ alkyl-$S(O)_nR^8$, or
—$C_1$–$C_9$ alkyl-$S(O)_nN(R^9)(R^{10})$;
Each $R^5$ is independently selected from
—H,
—$C_1$–$C_6$ alkyl,
—$C_3$–$C_6$ cycloalkyl, or
—$C_1$–$C_6$ alkyl-aryl;
Each $R^6$ is independently selected from
—H;
—$C_1$–$C_6$ alkyl,
-aryl,
-heteroaryl,
—$C_1$–$C_6$ alkyl-aryl,
—$C_1$–$C_6$ alkyl-heteroaryl,
—C(O)—$C_1$–$C_6$ alkyl,
—C(O)-aryl,
—C(O)—$C_1$–$C_6$ alkyl-aryl,
—C(O)-heteroaryl,
—C(O)—$C_1$–$C_6$ alkyl-heteroaryl,
—$C(NH)NH_2$,
—$S(O)_n$—$R^8$, or
—$C_1$–$C_6$ alkyl-$CO_2R^5$;
Each $R^7$ is independently selected from
—H,
—$C_1$–$C_6$ alkyl,
-aryl, or
-heteroaryl;
Each $R^8$ is independently selected from
—$C_1$–$C_6$ alkyl,
-aryl, or
-heteroaryl;
Each $R^9$ is independently selected from
—H,
—$C_1$–$C_6$ alkyl,
—$C_1$–$C_6$ alkyl-aryl,
—$C_1$–$C_6$ alkyl-heteroaryl,
—C(O)—$C_1$–$C_6$ alkyl,
—C(O)-aryl,
—C(O)—$C_1$–$C_6$ alkyl-aryl,
—C(O)—$C_1$–$C_6$ alkyl-heteroaryl,
-aryl, or
-heteroaryl;
Each $R^{10}$ is independently selected from
—H,
—$C_1$–$C_6$ alkyl,
—$C_1$–$C_6$ alkyl-aryl,
—$C_1$–$C_6$ alkyl-heteroaryl,
-aryl, or
-heteroaryl;
$R^{11}$ is
—H,
-aryl,
-heteroaryl,
—$C_1$–$C_6$ alkyl-heteroaryl,
—$C_3$–$C_6$ cycloalkyl,
—$C_1$–$C_6$ alkyl,
—$C_1$–$C_6$ alkyl-aryl,
—$C_1$–$C_6$ alkyl-$CO_2R^5$, or
—$C_1$–$C_6$ alkyl-$N(R^6)(R^7)$;
$R^{12}$ is
—H,
—$C_1$–$C_6$ alkyl,
-aryl, or
-heteroaryl;
$R^{13}$ is
—H,
—$C_1$–$C_6$ alkyl,
-aryl, or -heteroaryl;
and $R^{12}$ and $R^{13}$ taken together may form a cyclic alkyl ketal;
$B^1$ is selected from the group consisting of

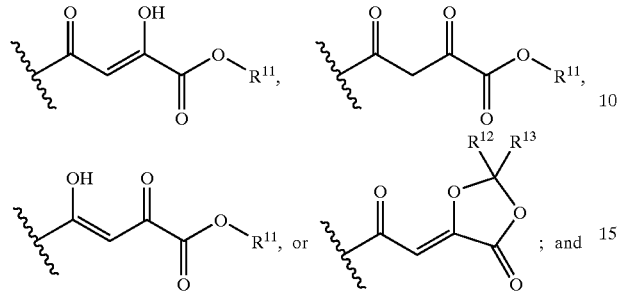

n is 0, 1 or 2;
or a pharmaceutically acceptable salt or solvate thereof.

2. A compound of claim 1 wherein
$R^1$ is
-phenyl or —$C_1$–$C_2$ alkyl-phenyl wherein the phenyl is unsubstituted or independently substituted with 1–3 $R^3$;
Each $R^3$ is independently selected from
—H,
-halo,
—CN,
—$C_1$–$C_6$ alkyl,
—$OC_1$–$C_6$ alkyl,
—$CO_2R^5$,
—$N(R^6)(R^7)$,
—$CON(R^6)(R^7)$,
trifluoromethyl;
$R^2$ is
—$C_1$–$C_6$ alkyl,
—$CH_2$-phenyl,
—$CH_2$–$CO_2R^5$,
—$C_1$–$C_2$-alkyl-$N(R^6)(R^7)$,
—$CH_2$—$CON(R^6)(R^7)$,
—$CH_2$—C(O)-heterocyclic radical;
$R^{11}$ is $R^5$;
$R^{12}$ and $R^{13}$ are $C_1$–$C_6$ alkyl or can be taken together may form a cyclic alkyl ketal;
$B^1$ is selected from the group consisting of

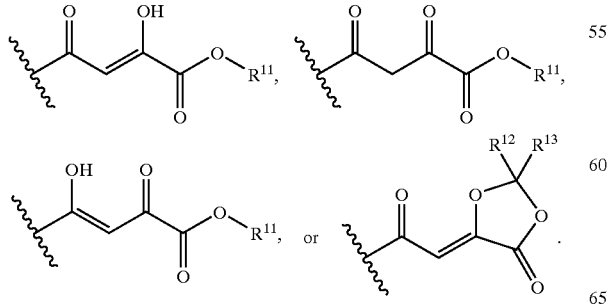

3. A compound of claim 1
wherein R' is

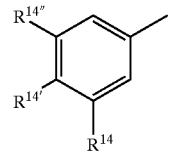

in which $R^{14}$, $R^{14'}$ and $R^{14''}$ are each independently selected from cyano, hydrogen or halo;
$R^2$ is $C_1$–$C_2$ alkyl or —$CH_2C(O)N(CH_2)_2$;
and B' is

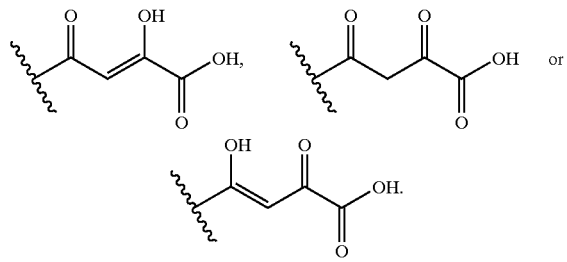

4. A compound of claim 3 selected from the group consisting of:
   3-[(4-Fluoro-benzyl)methoxy-carbamoyl]-2-hydroxy-acrylic acid;
   3-[(3,4-Difluoro-benzyl)-methoxy-carbamoyl]-2-hydroxy-acrylic acid;
   3-[(3-Bromo-4-fluoro-benzyl)-methoxy-carbamoyl]-2-hydroxy-acrylic acid;
   3-[(3-Cyano-4-fluoro-benzyl)-methoxy-carbamoyl]-2-hydroxy-acrylic acid;
   3-[(4-Fluoro-3-methyl-benzyl)-methoxy-carbamoyl]-2-hydroxy-acrylic acid;
   3-[Ethoxy-(4-fluoro-benzyl)-carbamoyl]-2-hydroxy-acrylic acid.

5. A compound of the formula

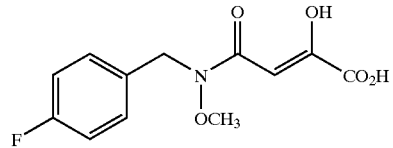

or a pharmaceutically acceptable salt or solvate thereof.

6. A compound of the formula

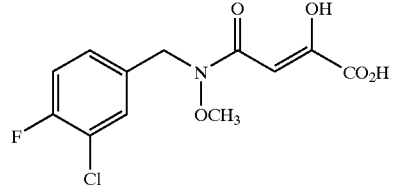

or a pharmaceutically acceptable salt or solvate thereof.

7. A compound of the formula

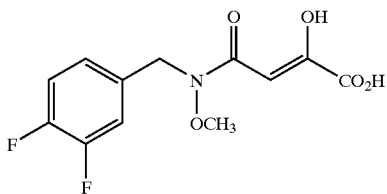

or a pharmaceutically acceptable salt or solvate thereof.

8. A compound of the formula

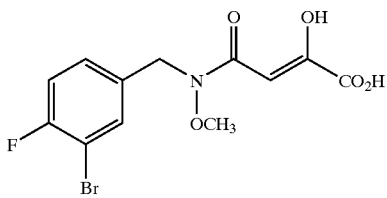

or a pharmaceutically acceptable salt or solvate thereof.

9. A compound of the formula

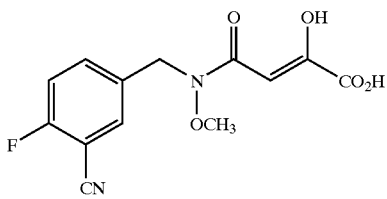

or a pharmaceutically acceptable salt or solvate thereof.

10. A compound of the formula

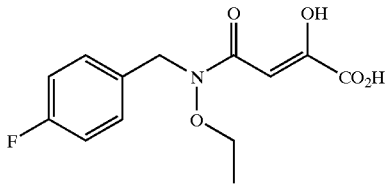

or a pharmaceutically acceptable salt or solvate thereof.

11. A compound of the formula

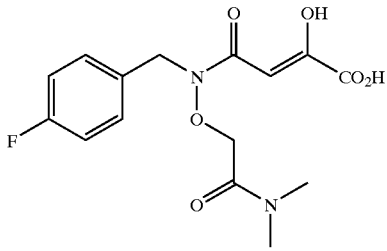

or a pharmaceutically acceptable salt or solvate thereof.

12. A compound of claim 1 wherein $R^1$ is

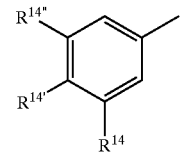

in which $R^{14}$, $R^{14\prime}$ and $R^{14\prime\prime}$ are each independently selected from cyano, hydrogen or halo;

$R^8$ is $C_1$–$C_2$ alkyl or —$CH_2C(O)N(CH_3)_2$;

and $B^1$ is

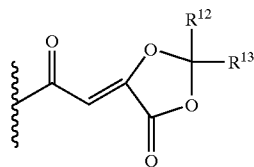

in which $R^{12}$ and $R^{13}$ are each independently $C_1$–$C_8$ alkyl or taken together form a cyclic alkyl ketal.

13. A compound of claim 12 wherein $R^{12}$ and $R^{13}$ are methyl.

14. A compound of claim 13 selected from the group consisting of:

2-(2,2-Dimethyl-5-oxo-[1,3]dioxolan-4-ylidene)-N-(4-fluoro-benzyl)-N-methoxy-acetamide;

N-(3,4-Difluoro-benzyl)-2-(2,2-dimethyl-5-oxo-[1,3]dioxolan-4-ylidene)-N-methoxy-acetamide;

N-(3-Bromo-4-fluoro-benzyl)-2-(2,2-dimethyl-5-oxo-[1,3]dioxolan-4-ylidene)-N-methoxy-acetamide;

N-(3-Cyano-4-fluoro-benzyl)-2-(2,2-dimethyl-5-oxo-[1,3]dioxolan-4-ylidene)-N-methoxy-acetamide;

2-(2,2-Dimethyl-5-oxo-[1,3]dioxolan-4-ylidene)-N-(4-Fluoro-3-methyl-benzyl)-N-methoxy-acetamide;

2-(2,2-Dimethyl-5-oxo-[1,3]dioxolan-4-ylidene)-N-ethoxy-N-(4-fluoro-benzyl)-acetamide.

15. A compound of the formula

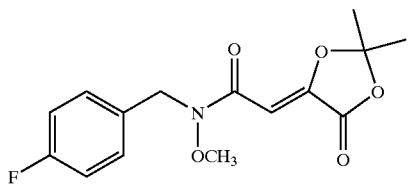

or a pharmaceutically acceptable salt or solvate thereof.

16. A composition useful for treating HIV infections comprising a therapeutic amount of a compound of claim 1 and a pharmaceutically acceptable carrier.

17. A pharmaceutical composition of claim 16, further comprising a therapeutically effective amount of one or more other HIV treatment agents selected from (a) an HIV protease inhibitor, (b) a nucleoside reverse transcriptase inhibitor, (c) a non-nucleoside reverse transcriptase inhibitor, (d) an HIV-entry inhibitor, (e) an immunomodulator, or a combination thereof.

18. A method of inhibiting HIV integrase which comprises administering to a mammal in need of such treatment a therapeutically effective amount of a compound of claim 1, or a pharmaceutically acceptable salt or solvate thereof.

19. A method for treating an HIV infection in a patient in need thereof, comprising the administration to such patient of a therapeutically effective amount of a compound of claim 1, or a pharmaceutically acceptable salt or solvate thereof.

* * * * *